US006451769B1

(12) United States Patent
Huebner et al.

(10) Patent No.: US 6,451,769 B1
(45) Date of Patent: Sep. 17, 2002

(54) COMPOSITIONS AND METHODS FOR ADMINISTERING BORRELIA DNA

(75) Inventors: Robert C. Huebner, Stroudsburg, PA (US); Jon A. Norman, San Diego, CA (US); Xiaowu Liang, La Jolla, CA (US); Kristin R. Carner, San Diego, CA (US); Alan G. Barbour; Catherine J. Luke, both of Irvine, CA (US)

(73) Assignees: Pasteur Merieux Serums et Vaccins, Lyons (FR); Vical, Inc., San Diego, CA (US); The University of Texas System, Austin, TX (US)

( * ) Notice: Subject to any disclaimer, the term of this patent is extended or adjusted under 35 U.S.C. 154(b) by 0 days.

(21) Appl. No.: 09/173,053

(22) Filed: Oct. 15, 1998

Related U.S. Application Data

(63) Continuation-in-part of application No. 08/663,998, filed on Jun. 14, 1996, now Pat. No. 5,846,946.

(51) Int. Cl.$^7$ .............................................. A61K 31/70
(52) U.S. Cl. ...................... 514/44; 435/91.4; 435/91.41; 435/320.1; 435/455
(58) Field of Search ............................ 435/320.1, 91.4, 435/91.41, 69.1, 325, 455; 514/44; 536/23.1

(56) References Cited

U.S. PATENT DOCUMENTS

| | | | |
|---|---|---|---|
| 5,122,458 A | | 6/1992 | Post et al. |
| 5,558,993 A | | 9/1996 | Champion et al. |
| 5,571,718 A | | 11/1996 | Dunn et al. |
| 5,620,896 A | * | 4/1997 | Herrmann et al. ........ 435/320.1 |
| 5,688,512 A | | 11/1997 | Bergstrom et al. |
| 5,736,524 A | * | 4/1998 | Content et al. ................ 514/44 |
| 5,846,946 A | * | 12/1998 | Huebner et al. ............... 514/44 |
| 5,942,236 A | * | 8/1999 | Lobet et al. ............. 424/234.1 |
| 5,981,505 A | * | 11/1999 | Weiner et al. ................. 514/44 |
| 6,090,586 A | * | 7/2000 | Bergstrom et al. ......... 435/69.3 |

FOREIGN PATENT DOCUMENTS

| | | | |
|---|---|---|---|
| EP | 0 346 316 A2 | | 12/1989 |
| WO | WO 94/16737 | * | 8/1994 |
| WO | WO 94/25596 | * | 11/1994 |
| WO | WO 95/14781 | * | 6/1995 |

OTHER PUBLICATIONS

Ngo et al., Computational Complexity Protein Structure Prediction and the Levinthal Paradox, 1994, Burkhauser Boston, vol. 14, pp. 492–495.*
McCluskie et al., Route and Method of Delivery of DNA Vaccine Influence Immune Response in Mice and Non–Human Primates, 1999, Molecular Medicine, vol. 5, pp. 287–300.*
Cryz et al., Vaccine Delivery Systems, pp. 667–688, 1996.*
Masuzawa et al., Microbiol. Immunolo., 40, 8:539–545, 1996.*
Fikrig et al., J. Exp. Med., vol. 181, pp. 215–221, 1995.*
Davis, M.G. et al., "Transfer and Expression of Plasmids Containing Human Cytomegalovirus Immediate–Early Gene 1 Promoter–Enhancer Sequences in Eukaryotic and Prokaryotic Cells" Biotechnology and Applied Biochemistry, 1998 vol. 1, No. 1, pp. 6–12.
Fikrig, E. et al., "Vaccination Against Lyme Disease Caused by Diverse *Borellia burgdorferi*" Journal of Experimental Medicine, 1995 vol. 183, pp. 215–221.
Luke, C.J. et al., "An OspA–Based DNA Vaccine Protects Mice Against Infection With *Borrelia burgdoreri*" Journal of Infectious Disease, 1997 vol. 175, No. 1, pp. 91–97.
Sadziene, A. et al., "Experimental Immunization against Lyme Borreliosis with recombinant Osp Proteins: An Overview"0 Infection, 1996, vol. 24, No. 2, pp. 195–202.
Simon, M.M. et al., "Protective Immunization with Plasmid DNA Containing the Outer Surface Lipoprotein A Gene of *Borrelia burgdorferi* is Independent of an Eukaryotic Promoter" European Journal of Immunology, 1996, vol. 26, pp. 2831–2840.
Probert et al., Infection and Immunity, pp. 1920–1926, May 1994.
Preac–Mursic, Infection 20, vol. 6, pp. 40/342–47/349, 1992.
Rauer et al., Journal of Clinical Microbiology, pp. 857–861, Apr. 1998.
Jauris–Heipke et al., Journal of Clinical Microbiology, pp. 1860–1866; Jul. 1995.
Padula et al., Infection and Immunity, pp. 5097–5105, Dec. 1993.
*Robinson et al., Seminars in Immunology, vol. 9, pp. 271–283, 1997.
*Barbour, Lyme Disease, the cause, the cure, the controversy. The Johns Hopkins University Press, pp. 240 and 241, 1997.
*Probert et al., Infection and Immunity, vol. 62(5): 1920–6, May 9, 1998.

(List continued on next page.)

Primary Examiner—Dave T. Nguyen
(74) Attorney, Agent, or Firm—Frommer Lawrence & Haug LLP; William S. Frommer; Thomas J. Kowalski

(57) ABSTRACT

Disclosed is a vaccine against Lyme Disease or its causative agent *Borrelia burgdorferi* (sensu stricto or sensu lato) containing a plasmid a DNA encoding a promoter for driving expression in a mammalian cell, DNA encoding a leader peptide for facilitating secretion/release of a prokaryotic protein sequence from a mammalian cell, a DNA encoding Borrelia OspA or OspB, and a DNA encoding a terminator. Disclosed too is an immunogenic composition against Lyme Disease or its causative agent *Borrelia burgdorferi* (sensu stricto or sensu lato) containing a plasmid comprising a DNA encoding a promoter for driving expression in a mammalian cell, DNA encoding a leader peptide for facilitating secretion/release of a prokaryotic protein sequence from a mammalian cell, a DNA encoding a Borrelia OspC, and a DNA encoding a terminator. And, methods for making and using such vaccines and the immunogenic composition are also disclosed.

12 Claims, 48 Drawing Sheets

OTHER PUBLICATIONS

*Bockenstedt et al., J. Innumology, 1993, 151(2):900–906, May 9, 1998.
*Schaibel et al., Vaccine 1993, vol. 11(10):1049–54, May 9, 1998.
*Montgomery et al., J. of Exp. Med. 1996, 183, 1:261–69.
*Fikrig et al.Infection and Immunity, Feb. 1992, vol. 60, No. 2:657–661.
*Rappuoli et al., Vaccine 1996, vol. 14, No. 7:691–716.
*Eisenbraun et al., DNA and Cell Biology 1996, vol. 2, No. 3:168–175.
*Mendoza–Vega et al., Applied Microb. Biotech., 1996 Jan., vol. 44(5):624–8.
*Katsumi et al., Hum. Gene. Ther. 1994, 5:1335–1339.
*Pardoll et al., Immunity 1995, 3(2):165–9.
*Robert Whalen, Emerging Infectious Diseases 1996, vol. 2, No. 3:168–75.

* cited by examiner

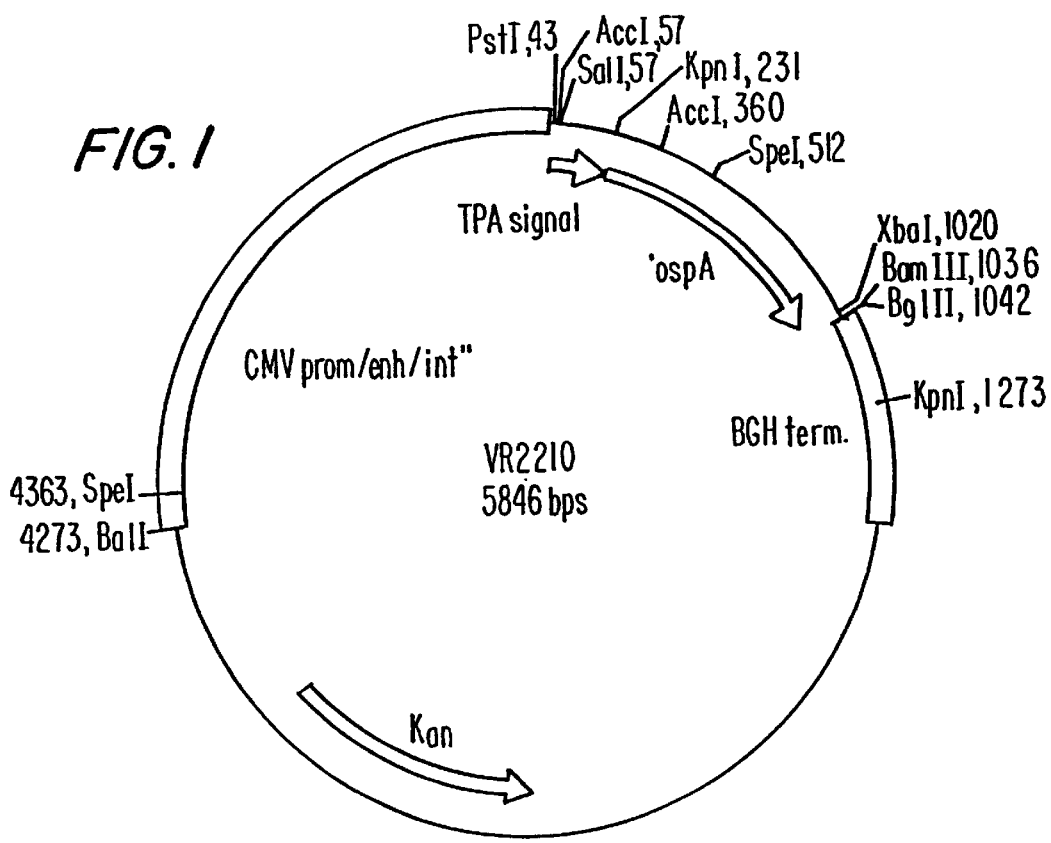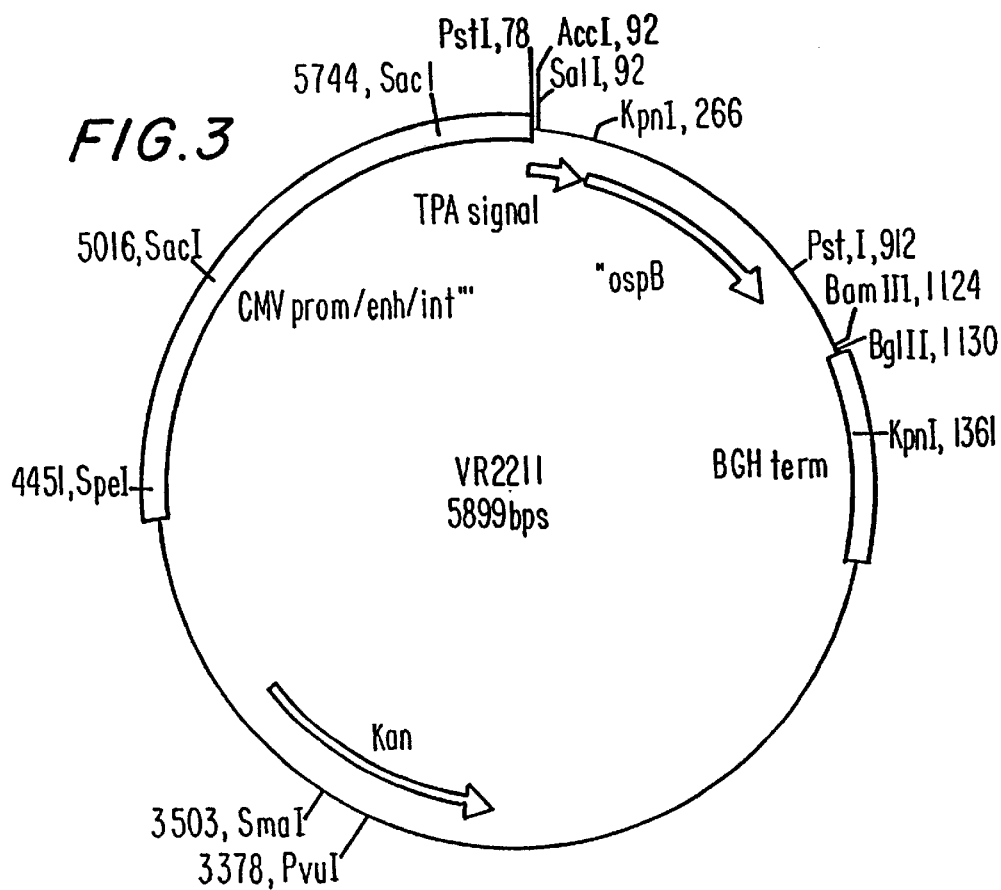

FIG. 2A

```
GTCACCGTCGTCGACCAGAGCTGAGATCCTACAGGAGTCCAGGGCTGGAGAGAGAAACCTCTGC
GAGGAAAGGGAAGGAGAGCAAGCCGTGAATTTAAGGACGTGTGAAGCAATCATGGATGCAAT
GAAGAGAGGGCTCTGCTGTGTGCTGTGAGCAGTGCGTTCGTTCGTTCGCCCAGCGGTAC
FWD C|GTAAGCAAATGTTAGC|AGCCTTGACGAGAAAAACAGCGTTTCAGTAGATTTGCCTGGTGA
AATGAAAGTTCTTGTAAGCAAAGAAAAAACAAGACGCAAGTACGATCTAATTGCAACAG
TAGACAAGCTTGAGCTTAAAGGAACTTCTGATAAAACAATGGATCTGGAGTACTTGAAGGCG
TAAAAGTGACAAAAGTAAAATAAAATAACAATTTCTGACGATCTAGGTCAAACCACACTTG
AAGTTTCAAAGAAGATGCAAAAACACTAGTATCAAAAAAAGTAACTTCCAAGACAAGTCA
TCAACAGAGAAAATTCAATGAAGTATCTGAAAATAAAGTAATAAACAAGAGCAGA
CGGAACCAGACTTGAATACAAGCTAACTGCTGAAAACAACATTAAAGCTAAAGAGGTTT
TAAAAGGCTATGTTCTTGAAGCAAAATATTTCAAAAAACTGGGAAGTTCAGTTGAACTAATGACA
GAACTGTACTTTAAGCAGTGCTACTAAAAAACTGCAGCTTGGAATTCAAAGAAGAACACAATAAGAA
CTGACAGTAGTGTGCTACTAAAAAACTAAAAGACCTTGTTTACAAAGAAGAACACAATTACAGTAC
TTACTGTAAACAGTAAAACTAAAAACTAAATGGCACCAAATTTGAAATTACAAAACTTGAT
AACAATAACGACTCAAATGGC|ICTTAAGTAACGCTCTT|AAGTGAGAATTTCTAGACCAGGGATCCAGATCTGC
REV GAA|ATTAAAACGC|CTCTTAAGTAAGGAGAATTTCTAGACCAGGGATCCAGATCTGC
TGTGCCTTCAGTTGCCAGCCATCTGTGTTGTTGCCCCTCCCCCGTTGACCCTGGAAG
GTGCCACTCCCACTGTCCTTTCCTAATAAATGAGGAAATTGCATTGCTGAGTAGGTG
TCATTCTATTCTGGGGGTGGGGTCGGTGATGTCAGGGAGGATTGGGAAGACAATA
GCAGGCATGCTGGGGATGCGGTCTATGGGCCACACATCCCTCTGTGACACCCTGTCCACG
CCTCCTGGGCCAGAAGCAGGCACACTCATAGCACACTCAGGAGGGCTCCGCCTTCAATCCC
GGTTCTTAGTTCCAGGGCTAAAGAAGTACTTGGAGGGTCTCTCCCTCCCCCATCAGCCCCCT
ACCCGCTAAAGTACTTGGAGGGTCTCTCCCTCCCCATCAGCCCACCAAACCTAGCCT
```

```
TTATTCATATCAGGATTATCAATACCATATTTTGAAAAAGCCGTTTCTGTAATGAAGGAGAA
AACTCACCGAGGCAGTTCCATAGGATGCAAGATCCTGGTATGCGATTCTGGTCTGCGACTCGT
CCAACATCAATACAACCTATTAATTTCCCCTCGTCAAAAATAAGGTTATCAAGTGAGAAATCA
CCATGAGTGACGACTGAATCCGGTGAGAATGGCAAAAGCTTATGCATTTCTTCCAGACTTGT
TCAACAGGCCAGCCATTACGCTCGTCATCAAAATCACTCGCATCAACCAAACCGTTATTCATTC
GTGATTGCGCCTGAGCGAGACGAAATACGCGATCGTGTTAAAAGGACAATTACAAACAGGA
ATCGAATGCAACCGGCGCAGGAACACTGCCAGCGCATCAACAATATTTCACTGAATCAGGA
TATTCTCTAATACCTGGAATGCTGTTTCCCGGGATCGCAGTGGTGAGTAACCATGCATCAT
CAGGAGTACGGATAAAAATGCTTGATGGTCGGCATAAATTCCGTCAGCCAGTTTAGTC
TGACCATCTCATCGTAACATCATTGGCAACGCTACCTTTGCCATGTTTCAGAAACAACTCTGG
CGCATCGGGCTTCCCATACAATACAGCATCAATCAATGTTGGAATTAATCGCGGCTCGACCTGATTGTCCCGACCTTATCGCGAGCC
CATTATACCCATATAAATCAGCATCCATGTTGGAATTAATCGCGGCTCTGAGCAAGACGTTT
CCCGTTGAATATGGCTCATAACACACCCTGTATTACTGTTTATGTAAGCAGACAGTTTATTGT
TCATGATGATATATTTTATCTGTGCAATGTAACATCAGAGATTTTGAGACACAACGTGGCTT
TCCCCCCCCCCATTATTGAAGCATTTATCAGGGTTATTGTCTCATGAGCGGATACATATTTG
AATGTATTTAGAAAAATAAACAAATAGGGGTTCCGCGCACATTTCCCCGAAAAGTGCCACCTG
ACGTCTAAGAAACCATTATTATCATGACATTAACCTATAAAAATAGGCGTATCACGAGGCCCT
TTCGTCTCGCGCGTTTCGGTGATGACGGTGAAAACCTCTGACACGCATGCTCCCGGAGACGG
TCACAGCTTGTCTGTAAGCGGATGCCGGGAGCAGACAAGCCCGTCAGGGGCGCGTCAGCGGGT
GTTGGGCGGGTCGTGTCGGGTGGCTTAACTATGCGGCATCAGAGATTGTACTGAGAGTGCAC
CATATGCGGTGTGAAATACCGCACAGATGCGTAAGGAGAAAATACCGCATCAGGATTGGCTATT
GGCCATTCGCCATTCGCCATTCGCCATCTGGTATCCATATCATATGTACATTTATATTGGCTCTCATGTCCAACATT
ACCGCCATACGTGTGACATGTTGACATTGATTATTAATAGTATTATTAATCAATTACGGGGTCATTAGTT
CATAGCCCATATATGAGTTCCGCGTTACACTTACGGTAAATGCCCGCCCTGGCTGACCG
```

FIG. 2D

```
CCCAACGACCCCCGCCCATTGACGTCAATAATGACGTATGTTCCCATAGTAACGCCAATAGGG
ACTTTCCATTGACGTCAATGGGTGGAGTATTTACGGTAAACTGCCCACTTGGCAGTACATCAA
GTGTATCATATGCCAAGTACGCCCCCTATTGACGTCAATGACGGTAAATGGCCCGCCTGGCAT
TATGCCCAGTACATGACCTTATGGGACTTTCCTACTTGGCAGTACATCTACGTATTAGTCATCG
CTATTACCATGGTGATGCGGTTTTGGCAGTACATCAATGGGCGTGGATAGCGGTTTGACTCAC
GGGGATTTCCAAGTCTCCACCCCATTGACGTCAATGGGAGTTTGTTTTGGCACCAAAATCAAC
GGGACTTTCCAAAATGTCGTAACAACTCCGCCCCATTGACGCAAATGGGCGGTAGGCGTGTAC
GGTGGGAGGTCTATATAAGCAGAGCTCGTTTAGTGAACCGTCAGATCGCCTGGAGACGCCATC
CACGCTGTTTTGACCTCAGAAGACACCGGGACCGATCCAGCCTCCAGCCTATCCGGAAACGGT
GCATTGGAACGCGGATTCCCCGTGCCAAGAGTGACGTAAGTACCGCCTATAGAGTCTATAGGC
CCACCCCCTTGGCTTCTTATGCATGTCTATACTGTTTTGCGGTCTATACACCCCCGCTTC
CTCATGTTATAGTGGTATATAGCTTACATTACTACTAATCCATAATGGCCATTATTGACCAC
TCCCTATTGGTGACGATATTTCCATTATTACATCGTTCCTTCAGAGACTGACACGGACTCTGTATTTTACAGGAT
GGGGTCTCATTTATTATTACAAATTCACATATACACAACACCACCGTCGGGTACGTGTTCCGCAGTTT
TTATTAAACATAACGTGGATCTCCACGCGAATCTCGGGTAGTGTTCCGGACATGGGCTCTTC
TCCGGTAGCGCGGAGCTTCTACATCCGAGCCCTGCTCCTCCAGCGACTCATGGTCGC
TCGCAGCTCCTCTGCCGCTAACAGTGGGAGGCCAGACTTAGGCACAGCACGATGCCCACCACCA
CCAGTGTGCCGCACAAGGCGTGCGGTAGGGTATGTGTCTGAAAATGAGCTCGGGGAGCGG
GCTTGCACCGCTGACGCATTTGGAAGACTAAGGCAGCAGAAGATGCAGGCAGCTG
AGTGTGTTCTGATAAGAGTCAGAGGTAACTCCCGTTGCCGGCTGGGCTGTTAACGGTGGAGGG
CAGTGTAGTCTGAGCAGTACTCGTTGCGCCGCCACCAGACATAATAGCTGACAGAC
TAACAGACTGTTCCTTCCATGGGTCTTTCTGCA
```

FIG. 4A

FWD CTGTGCACAAAAGGTGCTGAGTCAATTGCTCAAAAAGAGAAAATGATCTAAACCTTGAAGA
CTCAGTAAAAATCACATCAAAACGCTAAACAAGACCTTCCTGCGGTGACAGAAGACTCAGT
GTCTTTGTTAATGGTAATAAAATTTTGTAAGCAAGAAAAATAGCTCCGGCAAATATGA
TTAAGAGCAACAATTGATCAGGTTGAACTTAAAGGAACTTCCGATAAACAGTTTCTGG
AACCCTTGAAGGTTCAAAGCCTGACAAGAGAGTAAAGTAAAAATTAACAGTTTCTGCTGATTTAAA
CACAGTAACCTTAGAAGCATTTGATGCCAGCAACCAAAAAATTTCAAGTAAAGTTACTAAAAA
ACAGGGGTCAATAACAGAGAAACTCTCAAAGCTAATAAACAGATCAAAGAAATTAACAA
GATCAAACGGAACTACACTGAATACTCACAATAAGCAGATGCTGACAATGCTACAAAAGCA
GTAGAAACTCTAAAAATAGCATTAAGCTGAAGGAAGTCTTGTAGTCGGAAAAACAACAGT
GAAATTAAAGAAGAAGGTACTGTACTCTAAACAGCAAAAAACTAAAGATTGGTGTTCTTAACGAAAGTAAAAG
TCTTTTGAATGACACTGCTGACAGCAAAAAACAACACTGGAAGGATCAGCAAGTGAAATTAAA
CTTTAACAATTAGTGCTAACAACAATACAACGCTTAAAATAAGCTTTAATATATAGCCTTCTGTGCCTTCTA

REV AATCTTTCAGAGCTTAAAAACGCTTTATATATAGCCTTCTGTGCCTTCTA
GTTGCCAGCCATCTGTTGCCCCCGTGTTGACCCTGGAAGGTGCCACTCC
CACTGTCCTTCCTTCTAATGAGAAATTGCATTGTCTGAGTAGGTGTCATTCTATT
CTGGGGGTGGGGCAGCACAGCAAGGGAGGATTGGGAAGACAATAGCAGGCATG
CTGGGGATGGGGGGCTCTATGGGTACCCAGGTGCTGAAGAATTGACCCGGTTCCTCCTGGG
CCAGAAGAAGCAGGCACACCCTTCTGTGACACACCCCTGTCTCCAGCCCCTGGTTCTTAGT
TCCAGCCCCACTCATAGGACACTCAGGAGGGCTCCGCCTTCAATCCCACCCGCTAA
AGTACTTGGAGCGCTTCTCCCTCATCAGCCACCAAACCTAGCCTCCAAGAGT
GGGAAGAAATTAAAGCAAGATAGGCTATTAAGTGCAGAGGAGAAAATGCCTCCAACATG
TGAGGAAGTAATGAGAGAATCATAGAATTTCTCGCTTCCTCGCTCACTGACTCGCTGCGCT
CGGTCGTCGTTCGGCTGCTCGGGCGCGAGCGCGGTAATACGGTTATCCACAG

FIG. 4B

```
AATCAGGGGATAACGGCAGGAAGAACATGTGAGCAAAAGGCCAGCAACCG
TAAAAGGCCGCGTTGCTGGCGTTTTTCCATAGGCTCCGCCCCCCTGACGAGCATCACAAAAA
TCGACGCTCAAGTCAGAGGTGGCGAAACCCGACAGGACTATAAAGATACCAGGCGTTTCCCC
TGGAAGCTCCCTCGTGCGCTCTCCTGTTCCGACCCTGCCGCTTACCGGATACCTGTCCGCTTT
CTCCCTTCGGGAAGCGTGGCGCTTTCTCAATGCTCACGCTGTAGGTATCTCAGTTCGGTGTAGG
TCGTTCGCTCCAAGCTGGGCTGTGTGCACGAACCCCCCGTTCAGCCCGACCGCTGCGCCTTATC
CGGTAACTATCGTCTTGAGTCCAACCCGGTAAGACAGACGACTTATCGCCACTGGCAGCAGCCAC
TGGTAACAGGATTAGCAGAGCGAGGTATGTAGGCGGTGCTACAGAGTTCTTGAAGCCAGTGGCC
TAACTACGGCTACACTAGAAGGACAGTATTTGGTATCTGCGCTCTGCTGAAGCCAGTTACCTTC
GGAAAAAGAGTTGGTAGCTCTTGATCCGGCAAACAACCACCGCTGGTAGCGGTGGTTTTTT
GTTTGCAAGCAGCAGATTACGCGCAGAAAAAAAGGATCTCAAGAAGATCCTTTGATCTTTTCT
ACGGGGTCTGACGCTCAGTGGAACGAAAACTCACGTTAAGGGATTTTGGTCATGAGATTATCA
AAAGGATCTTCACCTAGATCCTTTTAAATTAAAAATGAAGTTTTAAATCAATCTAAAGTATA
TATGAGTAAACTTGGTCTGACAGTTACCAATGCTTAATCAGTGAGGCACCTATCTCAGCGATCT
GTCTATTTCGTTCATCCATAGTTGCCTGACTCCCCGTCGTGTAGATAACTACGATACGGGAGG
GCTTACCATCTGGCCCCAGTGCTGCAATGATACCGCGAGACCCACGCTCACCGGCTCCAGATT
TATCAGCAATAAACCAGCCAGCCGGAAGGGCCGAGCGCAGAAGTGGTCCTGCAACTTTATCCGC
CTCCATCCAGTCTATTAATTGTTGCCGGGAAGCTAGAGTAAGTAGTTCGCCAGTTAATAGTTTGC
GCAACGTTGTTGCCATTGCTACAGGCATCGTGGTGTCACGCTCGTCGTTTGGTATGGCTTCATT
CAGCTCCGGTTCCCAACGATCAAGGCGAGTTACATGATCCCCCATGTTGTGCAAAAAAGCGGT
TAGCTCCTTCGGTCCTCCGATCGTTGTCAGAAGTAAGTTGGCCGCAGTGTTATCACTCATGGT
TATGGCAGCACTGCATAATTCTCTTACTGTCATGCCATCCGTAAGATGCTTTTCTGTGACTGGT
GAGTACTCAACCAAGTCATTCTGAGAATAGTGTATGCGGCGACCGAGTTGCTCTTGCCCGGCG
TCAATACGGGATAATACCGCGCCACATAGCAGAACTTTAAAAGTGCTCATCATTGGAAAACGT
TCTTCGGGGCGAAAACTCTCAAGGATCTTACCGCTGTTGAGATCCAGTTCGATGTAACCCACT
CGTGCACCCAACTGATCTTCAGCATCTTTTACTTTCACCAGCGTTTCTGGGTGAGCAAAAACAG
GAAGGCAAAATGCCGCAAAAAAGGGAATAAGGGCGACACGGAAATGTTGAATACTCATACTCT
TCCTTTTTCAATATTATTGAAGCATTTATCAGGGTTATTGTCTCATGAGCGGATACATATTTG
AATGTATTTAGAAAAATAAACAAATAGGGGTTCCGCGCACATTTCCCCGAAAAGTGCCACCTG
ACGTCTAAGAAACCATTATTATCATGACATTAACCTATAAAAATAGGCGTATCACGAGGCCCT
TTCGTCTTCAAGAATTCGATATCAAGCTTATCGATACCGTCGACCTCGAGGGGGGGCCCGGT
ACCCAATTCGCCCTATAGTGAGTCGTATTACAATTCACTGGCCGTCGTTTTACAACGTCGTGA
CTGGGAAAACCCTGGCGTTACCCAACTTAATCGCCTTGCAGCACATCCCCCTTTCGCCAGCTG
GCGTAATAGCGAAGAGGCCCGCACCGATCGCCCTTCCCAACAGTTGCGCAGCCTGAATGGCGA
ATGGCGCCTGATGCGGTATTTTCTCCTTACGCATCTGTGCGGTATTTCACACCGCATATGGTG
CACTCTCAGTACAATCTGCTCTGATGCCGCATAGTTAAGCCAGCCCCGACACCCGCCAACACC
CGCTGACGCGCCCTGACGGGCTTGTCTGCTCCCGGCATCCGCTTACAGACAAGCTGTGACCG
TCTCCGGGAGCTGCATGTGTCAGAGGTTTTCACCGTCATCACCGAAACGCGCGAGGCAGCTGC
GGTAAAGCTCATCAGCGTGGTCGTGAAGCGATTCACAGATGTCTGCCTGTTCATCCGCGTCCA
GCTCGTTGAGTTTCTCCAGAAGCGTTAATGTCTGGCTTCTGATAAAGCGGGCCATGTTAAGGG
CGGTTTTTTCCTGTTTGGTCACTGATGCCTCCGTGTAAGGGGGATTTCTGTTCATGGGGGTAA
```

FIG. 4C

```
CCATTACGCTCGTCATCATCAAAATCACTCGCATCAACCAAACCGTTATTCATTCGTGATTGCGCCT
GAGCGAGACGAAATACGCGATGCTGTGTTAAAAGGACAATTACAAACAGGAATCGAATGCAAC
CGGCGCAGGAACACTGCCAGCGCATCAACAACATATTTCACCTGAATCAGGATATTCTCTAAT
ACCTGGAATGCTGTTTCCCGGGATCGCAGTGGTGAGTAACCATGCATCATCAGGAGTACGG
ATAAAATGCTTGATGGTCGGAAGAGGCATAAATTCCGTCAGCAGTTTAGTCTGACCATCTCA
TCTGTAACATCATTGGCAACGCTACCTTTGCCATGTTTCAGAAACAACTCTGGGCGCATCGGGCT
TCCCATACAATCGATAGATTGTCGCACCTGATTATCGCGACATTATCGCGAGCCCATTTATACCC
ATATAAATCAGCATCCATGTTGGAATTAATCGCGGCCTCGAGCAAGACGTTTCCCGTTGAAT
ATGGCTCATAACACCCCTGTATTACTGTTTATGTAAGCAGACAGTTTATTGTTCATGATGAT
ATATTTTATCTGTGCAATGTAACATCAGAGATTTGAGACACAACGTGGCTTTCCCCCCCC
CCCATTATTGAAGCATTATCAGGGTTATTGTCTCATGAGTATACATATTTGAAATGTATTTA
GAAAAATAAACAAATAGGGGTTCCCGCACATTTCCCCGAAAAGTGCCACCTGACGTCTAAG
AAACCATTATTATCATGACATTAACCTCTGACACATGGCGTATCACGAGGCCCTTTCGTCTCGC
GCGTTTCGGTGATGACGGATGCCGGGAGCAGACAAGCCGTCAGGCGCGTCAGAGCGGTCACAGCTTG
TCTGTAAGCGGATGGCTTAACTATGCCGGGAAGTGCGTTACTGAGAGTGCACCATATGCGGT
GTCGGGGATGGCGTGGCTGGCCCGGACACAGATGCGTAAGGAGAAAATACATCAGGCTCACAGCTTG
GTGAAATACCGCACAGATGCGTAAGGAGAAAATACATTTATAGTCAATTACGGTCAACAGCCATGCA
TACGTTGTATCCATAATCATAATGTACATTATAATAGTAATAACTTACGGTAAATGGCCCGCCTGGTC
TGACATTGATTATTGACTAGTTACATAAACTTACGGTAAATGGCCCGCCTGACGCCCAACGACC
ATATGGAGTTCCGCGTTACATAACTTACGGTATGTTCCCATAGTAACGCCAATAGGGACTTTCCATTG
CCCGCCCATTGACGTCAATAATGACGTATGTTCCCATAGTAACGCCAATAGGGACTTTCCATTG
```

```
ACGTCAATGGGTGGAGTATTTACGGTAAAACTGCCACTTGGCAGTACATCAAGTGTATCATAT
GCCAAGTACGCCCCCTATTGACGTCAATGACGGTAAATGGCCCGCCTGGCATTATGCCCAGTA
CATGACCTTATGGGACTTTCCTACTTGGCAGTACATCTACGTATTAGTCATCGCTATTACCATG
GTGATGCGGTTTTGGCAGTACATCAATGGGCGTGGATAGCGGTTTGACTCACGGGGATTTCCA
AGTCTCCACCCCATTGACGTCAATGGGAGTTTGTTTTGGCACCAAAATCAACGGGACTTTCCA
AAATGTCGTAACAACTCCGCCCCATTGACGCAAATGGGCGGTAGGCGTGTACGGTGGGAGGTC
TATATAAGCAGAGCTCGTTTAGTGAACCGTCAGATCGCCTGGAGACGCCATCCACGCTGTTTT
GACCTCCATAGAAGACAGGGACCCGGAAATCCAGCAGCCGGGAAACGGTGCATTGGAAC
GCGGATTCCCCGTGCCAAGAGTGACGTAAGTACCGCCTAATAGAGTCTATAGGCCACCCCCTT
GGCTTCTTATGCATGCTATACTGTTTTTGGCTTGGGTCTATACACCCCGCTTCCTCATGTTAT
AGGTGATGGTATAGCCTATAGTGTGGGTTATTGACCATTATTGACCACTCCCTATTG
GTGACGATACTTTCCATTACTAATCCATAAACATGCTCTTGCCACAACTCTCTTATTGGCTAT
ATGCCAATACACTGTCCTTCAGAGACTGACACGACCACCAGTCGGTACGTGTCCGAATCTCAT
TTATTATTACAAATTCACATATATACAACACCACCCCAGTGCCCAGTTTTTATTAAACA
TAACGTGGGATCTCCACGCGAATCTCCAGCCTTCCGAATCTCCAGCCTCATGGCTCTCTCCGGTAGC
GGCGGAGCTTCTACATCCGAGCCCCTGGGCCTAGGGCCCAGCACGATGCCCACCACCAGTGTGC
CCTTGCTCCTAACAGTGCCTGTGGCGTAGGGTAGGGTGTCTGAAATGAGCTGCAGGAGCGGCTTGCACC
CGCACAAGGCTTCTACATCCGAGCCTGTGGCGTAGGTACCTCGGAGCGGGCTTGCACC
GCTGACGCATTTGGAAGACTTAAGGCAGGTAACTCTGCCTGTGTTAACGGTGGAGGGCAGTAGT
GTTCTGATAAGAGTCAGAGTCAAGAGGTAACATAATAGCTGACAGATAACAGACT
CTGAGCAGTACTCGTGTGCTGAGTCTTTCTGCCGAAGAAACCTCTGCGAGATCCTACAGGAGT
GTCCTTTCATGGGTCTTTTCTGCCAGTCCTGCGACCAGTCGTCGTGAGGAAGCAAGCCGTGAATTAAGGAA
CCAGGGCTGGAGAGAAAACCTCATGGATGCAATCATGAAGAGAGGGTCTGTGCTGTGGA
GCTGTGTGAAGCAATCATGAAGAGAGGGTCTGTGCTGTGTGGA
CGCTGTGTGAAGCAATCATGAAGAGAGGGTCTGTGCTGTGTGGA
GCAGTCTTCGTTTCGCCCCAGCGGGTAC
```

```
GATCCNNNNNNNNNNNNNNNNAAGCTTAATTAGAACCAAACTTAATTAAAACCA
AACTTAATTGAAGTTATTATCATTTTATTTCAATTTCTATTTGTTATTTGTTAATCTTAT
AATATAATTATACTTGTATTAAGTTATAATTATAAAGGAGAATATATTATGAAAAATAT
TTATTGGGAAATAGGTCTAATATATTAGCCTTAATAATGTAAGCAAAATGTTAGCAGCCTTGAC
GAGAAAAACAGCGTTCAGTAGATTTGCCTGGTGAAATGAAAGTTCTGTAAGCAAAGAAAA
AAACAAGACGGCAAGTACGATCTAATGCAACAGTAGACAAGCTTAAGGAACTT
CTGATAAAAACAATGGATACTTGGAGTACTTGAAGCGTAAAAGCTGACAAAGTAAAA
TT.AACAATTTCTGACGATCTAGTTCAAACCACACTTGAAGTTTTCAAAGAAGATGGCAAAACA
CTAGTATCAAAAAAAAGTAACTTCCAAAGACAAGTCATCAACAGAGAAAAATTCAATGAAAA
AGGTGAAGTATCTGAAAAAATAATAACAAGACAGATTTAAAAGGTTCTATGTTCTTGAAGGAACTC
TAAACTGCTGAAAAAACAACATTGGTGAACTTAATGACACTGACAGTAGTGCTACTAAAAAAT
CAAAATCTGGGGAAGTTCAGGCACTTCAACTTAAACAGTAAACATTACTGTAAACAATAAAAACTAAAG
CTGCAGCTTGGAATTCAGGAAACACAAAATTACAACATACACAATGGAACAATACGACTCAAATGGCACCAAAT
ACCTTGTGTTTACAAAAGAACAGTTGAAATTACAAACTTGATGAAATTAAAACGCTTAAATAAGGA
TAGAGGGGTCAGCAGTTGAAATTACAAACTTGATGAAATTAGAATAGGATGTGCACAAAA
GAATTATGAGATTATTAATAGGATTTGCTTTAGCGTTAATAGGATGTGCACAAAA
GGTGCTGAGTCNNNNNNNGTTGGGAATTCGTAATCACAACATACGAGCCGGAAGCATAAAGTGTAAAGCCTGGG
TTGTTATCCGCTCACACATCCACACAACATCAGCCGGAAGCATAAGCCTTCACTGCCCGCTTCCAGTCGGA
TGCCTAATGAGTGAGCTAACTCACATTAATGAATCGGCCAACGCGCGGGAGAGGGCGGTTTGCGTATT
AACCTGTCGTGCCAGCTGCATTAATGAATCGGCCAACGCGCGGGGAGAGGGCGGTTTGCGTATT
GGGCGCTCTTCCGCTTCCTCGCTCACTGACTCGCTGCGCTCGGTCGTTCGGGCTGCGGCGAGCGG
```

FIG. 5B

```
TATCAGCTCACTCAAAGGCGGTAATACGGTTATCCACAGAATCAGGGGATAACGCAGGAAAG
AACATGTGAGCAAAAGGCCAGCAAAAGGCCAGGAACCGTAAAAAGGCCGCGTTGCTGGCGTT
TTTCCATAGGCTCCGCCCCCCTGACGAGCATCACAAAAATCGACGCTCAAGTCAGAGGTGGCG
AAACCCGACAGGACTATAAAGATACCAGGCGTTTCCCCCTGGAAGCTCCCTCGTGCGCTCTC
TGTTCCGACCCTGCCGCTTACCGGATACCTGTCCGCCTTTCTCCCTTCGGGAAGCGTGGCGCTT
TCTCATAGCTCACGCTGTAGGTATCTCAGTTCGGTGTAGGTCGTTCGCTCCAAGCTGGGCTGTG
TGCACGAACCCCCCGTTCAGCCCGACCGCTGCGCCTTATCCGGTAACTATCGTCTTGAGTCCAA
CCCGGTAAGACACGACTTATCGCCACTGGCAGCAGCCACTGGTAACAGGATTAGCAGAGCGA
GGTATGTAGGCGGTGCTACAGAGTTCTTGAAGTGGTGGCCTAACTACGGCTACACTAGAAGGA
CAGTATTTGGTATCTGCGCTCTGCTGAAGCCAGTTACCTTCGGAAAAAGAGTTGGTAGCTCTTG
ATCCGGCAAACAAACCACCGCTGGTAGCGGTGGTTTTTTTGTTTGCAAGCAGCAGATTACGCG
CAGAAAAAAAGGATCTCAAGAAGATCCTTTGATCTTTTCTACGGGGTCTGACGCTCAGTGGAA
CGAAAACTCACGTTAAGGGATTTTGGTCATGAGATTATCAAAAGGATCTTCACCTAGATCCT
TTTAAATTAAAAATGAAGTTTTAAATCAATCTAAAGTATATATGAGTAAACTTGGTCTGACAG
TTACCAATGCTTAATCAGTGAGGCACCTATCTCAGCGATCTGTCTATTTCGTTCATCCATAGTT
GCCTGACTCCCCGTCGTGTAGATAACTACGATACGGGAGGGCTTACCATCTGGCCCCAGTGCT
GCAATGATACCGCGAGACCCACGCTCACCGGCTCCAGATTTATCAGCAATAAACCAGCCAGCC
GGAAGGGCCGAGCGCAGAAGTGGTCCTGCAACTTTATCCGCCTCCATCCAGTCTATTAATTGT
TGCCGGGAAGCTAGAGTAAGTAGTTCGCCAGTTAATAGTTTGCGCAACGTTGTTGCCATTGCT
ACAGGCATCGTGGTGTCACGCTCGTCGTTTGGTATGGCTTCATTCAGCTCCGGTTCCCAACGAT
CAAGGCGAGTTACATGATCCCCCATGTTGTGCAAAAAAGCGGTTAGCTCCTTCGGTCCTCCGA
TCGTTGTCAGAAGTAAGTTGGCCGCAGTGTTATCACTCATGGTTATGGCAGCACTGCATAATTC
TCTTACTGTCATGCCATCCGTAAGATGCTTTTCTGTGACTGGTGAGTACTCAACCAAGTCATTC
TGAGAATAGTGTATGCGGCGACCGAGTTGCTCTTGCCCGGCGTCAATACGGGATAATACCGCG
```

FIG.5C

```
CCACATAGCAGAACTTAAAGTGCTCATCATTGGAAAACGTTCTTCGGGGCGAAAACTCTCA
AGGATCTTACCGCTGTTGAGATCCAGTTCGATGTAACCACTCGTGCACCAACTGATCTTCAG
CATCTTTTACTTTCACCAGCGTTTCTGGGTGAGCAAAAACAGGAAGGCAAAATGCCGCAAAAA
AGGGAATAAGGGCGACACGGAAATGTTGAATACTCATACTCTCCTTTTCAATATTATTGAA
GCATTATCAGGGTTATTGTCTCATGAGCGGATACATATTTGAATGTATTTAGAAAATAAAC
AAATAGGGGTTCCGCGCACATTTCCCGAAAAGTGCCACCTGACGTCTAAGAAACCATTATTA
TCATGACATTAACCTATAAAAATAGGCGTATCACGAGGCCCTTTCGTCTCGCGTTTCGGTGA
TGACGGTGAAAACCTCTGACACATGCAGCTCCCGGAGACGGTCACAGCTTGTCTGTAAGCGGA
TGCCGGGAGCAGACAAGCCCGTCAGGGCGTCAGGGTGTTGGGGGGTGTCGGGGCTGGC
TAACTATGCGGCATCAGAGCAGATTGTACTGAGAGTGCACCATATGCGGTGTGAAATACCGC
ACAGATGCGTAAGGAGAGAAAATACCGCATTCAGCCGCCATTCGCCAGCTGGCGCAACTGTT
GGGAAGGGCGATCGGTGCGGGCCTCTTCGCTATTACGCCAGCTGGCGAAAGGGGGATGTGCT
GCAAGGCGATTAAGTTGGGTAACGCCAGGGTTTTCCCAGTCACGACGTTGTAAAACGACGGCC
AGTGCCAAGCTTGGCTGCAGGTCGACGCTCTCCCTTATGCGACTCCTGCATTAGGAAGCAGCC
CAGTAGTAGGTTGAGGCCGTTGAGCCACCCGGCCTGCAAGGAATGTGCATGCAAGGAGATGG
CGCCCAACAGTCCCCCGCGCCACCGCGCCCATATACCGCGAAACAAGCGCTCATGA
GCCCGAAGTGGCGAGCCCGATCTTCCCCATCGGTGATGTCGGCGATATAGGCGCCAGCAACCG
CACCTGTGGCGCCGGTGATGCCGGCCACGATGCGTCCGGCGTAGAG
```

FIG. 6A

```
AATTCAGGCACTTCAACTTTAACAATTACTGTAAACAGTAAAAAACTAAAGACCTGTGTTT
ACAAAGAAAACAATTACAGTACAACAATACGACTCAAATGGCACCAAATTAGAGGGGTC
AGCAGTTGAAATTACAAACTGATGAAAAACGCTTAAAATAAGGAGAATTTATGA
GATTATTAATAGGATTTAGCGTTTAGCTTAATAGGATGTGCACAAAAGGTGCTGAGT
CAATTGGTTCTCAAAAGAAAATCTAAACCTTGAAGACTCTAGTAAAAATCACATCAAA
ACGCTAAACAAGACCTTCCTGCGGTGACAGAAGACTCAGTGTCTTTGTTTAATGGTAATAAAA
TTTTGTAAGCAAAAGAAAATAGCTCCGGCAAATATGATTAAGAGCAACAATTGATCAGG
TTGAACTTAAGGAACTTCCGATAAAAACAATGGTTTCTGAACCCTTGAAGGTTCAAGCCTG
ACAAGAGTAAAGTAAAATTAACAGTTTCTGTGATTTAAACACAGTAACCTTAGAAGCATTTG
ATGCCAGCAACCAAAAATTCAAGTAACTAAAAATTAACAAAGGGTCAATAACAGAGGAA
ACTCTCAAGCTAATAAACAGATAAATTTAGACTCAAAAGCTACAAAGGACTACACTTGA
ATACTCACAAATAACAGATGCTGACAATGTCTACACAAGCAGTAGAAACTCTAAAAATAGCA
TAAGCTTGAAGGAAGTCTTGTAGTCGGAAAAAGATGAAATTAAAGAAGGTACTGTT
ACTCTAAAAAGAAGAGAAATTGAAAAGTAAATGGGAAGACAGTAAAAGTCTTTTGAATGACACTGCAGG
TCTAACAAAAAAACAGGTAAATTGGTGTTCTTAACAGTACACTTAACAATTAGTGCTGACA
GCAAAAAACTAAAGACCAGCTGGAACCAGCTAGAAGGATCAGCAAGTGAAATTAAAATCTTCAGCTAAAAAC
CAGCTGGAACCAGCTAGAAGGATCAGCAAGTGAAATTAAAATCTTCAGCTAAAAAC
GCTTTAAAATATATAAGTAAACCCCTACAAGGCATCAGTGTAGGAAGCTAGGAAGAAGNNNNNN
NGGCCNNNNNNGTTGGGATCCGGTCGGGAAAAATTGTTATCCGCTAATCATGGTCATA
GCTGTTCCTGTGTAAGCCTGGGGCCTAATGAGTGAGCTAACTCACATTAATGAATCGAGCCGGAAGCAT
AAGTGTAAGCCTGGGAAACCTGTCGTGCCAGCTGCATTAATGAATCGGCCAACGCGCGGG
GCCCGCTTTCCAGTCGGGAAACCTGTCGTGCCAGCTGCATTAATGAATCGGCCAACGCGCGGG
GAGAGGCGGTTTGCGTATTGGGCGCTCTTCCGCTTCCTCGCTCACTGACTCGCTGCGCTCGGTC
```

FIG. 6B

```
GTTCGGCTGCGGCGAGCGGTATCAGCTCACTCAAAGGCGGTAATACGGTTATCCACAGAATCA
GGGATAACGCAGGAAAGAACATGTGAGCAAAAGGCCAGCAAAAGGCCAGGAACCGTAAAA
AGGCCGCGTTGCTGGCGTTTTTCCATAGGCTCCGCCCCCCTGACGAGCATCACAAAAATCGAC
GCTCAAGTCAGAGGTGGCGAAACCCGACAGGACTATAAAGATACCAGGCGTTTCCCCCTGGA
AGCTCCCTCGTGCGCTCTCCTGTTCCGACCCTGCCGCTTACCGGATACCTGTCCGCCTTTCTCCC
TTCGGGAAGCGTGGCGCTTTCTCATAGCTCACGCTGTAGGTATCTCAGTTCGGTGTAGGTCGTT
CGCTCCAAGCTGGGCTGTGTGCACGAACCCCCCGTTCAGCCCGACCGCTGCGCCTTATCCGGT
AACTATCGTCTTGAGTCCAACCCGGTAAGACACGACTTATCGCCACTGGCAGCAGCCACTGGT
AACAGGATTAGCAGAGCGAGGTATGTAGGCGGTGCTACAGAGTTCTTGAAGTGGTGGCCTAA
CTACGGCTACACTAGAAGGACAGTATTTGGTATCTGCGCTCTGCTGAAGCCAGTTACCTTCGG
AAAAAGAGTTGGTAGCTCTTGATCCGGCAAACAAACCACCGCTGGTAGCGGTGGTTTTTTTGT
TTGCAAGCAGCAGATTACGCGCAGAAAAAAAGGATCTCAAGAAGATCCTTTGATCTTTTCTAC
GGGGTCTGACGCTCAGTGGAACGAAAACTCACGTTAAGGGATTTTGGTCATGAGATTATCAAA
AAGGATCTTCACCTAGATCCTTTTAAATTAAAAATGAAGTTTTAAATCAATCTAAAGTATATAT
GAGTAAACTTGGTCTGACAGTTACCAATGCTTAATCAGTGAGGCACCTATCTCAGCGATCTGT
CTATTTCGTTCATCCATAGTTGCCTGACTCCCCGTCGTGTAGATAACTACGATACGGGAGGGCT
TACCATCTGGCCCCAGTGCTGCAATGATACCGCGAGACCCACGCTCACCGGCTCCAGATTTAT
CAGCAATAAACCAGCCAGCCGGAAGGGCCGAGCGCAGAAGTGGTCCTGCAACTTTATCCGCCT
CCATCCAGTCTATTAATTGTTGCCGGGAAGCTAGAGTAAGTAGTTCGCCAGTTAATAGTTTGCG
CAACGTTGTTGCCATTGCTACAGGCATCGTGGTGTCACGCTCGTCGTTTGGTATGGCTTCATTC
AGCTCCGGTTCCCAACGATCAAGGCGAGTTACATGATCCCCCATGTTGTGCAAAAAAGCGGTT
AGCTCCTTCGGTCCTCCGATCGTTGTCAGAAGTAAGTTGGCCGCAGTGTTATCACTCATGGTTA
TGGCAGCACTGCATAATTCTCTTACTGTCATGCCATCCGTAAGATGCTTTTCTGTGACTGGTGA
```

FIG. 6C

GTACTCAACCAAGTCATTCTGAGAATAGTGTATGCGGCGACCGAGTTGCTCTTGCCCGGCGTC
AATACGGGATAATACCGCGCCACATAGCAGAACTTTAAAGTGCTCATCATTGGAAAACGTTC
TTCGGGGCGAAACTCTCAAGGATCTCAAGGATCTTACCGCTGTTGAGATCCAGTTCGATGTAACCCACTCG
TGCACCCAACTGATCTTCAGCATCTTTTACTTTCACCAGCGTTTCTGGGTGAGCAAAACAGGA
AGGCAAAATGCCGCAAAAAAGGGAATAAGGGCGACACGGAAATGTTGAATACTCATACTCTT
CCTTTTCAATATATTATTGAAGCATTTATCAGGGTTATTGTCTCATGAGCGGATACATATTGAA
TGTATTTAGAAAAATAACAAATAGGGGTTCCGCGCACATTTCCCGAAAAGTGCCACCTGAC
GTCTAAGAAACCATTATTATCGACATTAAACCTCTGACACATGCAGCTCCCGGAGACGGTC
CGTCTCGCGCGTTTGCGTTTCGGTGATGAAAACCTCTGACACATGCAGCTCCCGGAGACGGTC
ACAGGCTTGTCTGTAAGCGGATGCCGGGAGCAGACAAGCCCGTCAGGCGTCAGGCGGGTGT
TGGCGGGGTGTGTCGGGGCTTAACTATGCGGCATCAGAGCAGATTGTACTGAGAGTGCACCA
TATGCGGTGTGAAATACCGCACAGATGCGTAAGGCCATCAGGCGCCATTCGC
CATTCAGGCTGCAACTGTGGGAAGGGCGATCGGTGCCTCTTCGCTATTACGCCAGC
TGGCGAAAGGGGGATGTGCTGCAAGGCGATTAAGTTGGGTAACGCCAGGGTTTTCCCAGTCAC
GACGTTGTAAAACGACGGCCAGTG

```
                40                    50
SerValAspLeuProGlyGluMetLysValLeuValSerLysGluLysAsnLysAspGly
TCAGTAGATTTCCCTGGTGAAATGAAGTTCTGTAAGGAAAAAACAAGGACGGC
                                                    100

60                    70
LysTyrAspLeuIleAlaThrValAspLysLeuLeuGluLeuLysGlyThrSerAspLysAsn
AAGTACGATCTAATTGCAACAGTAGACAAGCTTGAGCTTAAAGGAACTTCTGATAAAAAC
                                                    160

80                    90
AsnGlySerGlyValIleLeuGluGlyValLysAlaAspLysSerLysValLysLeuThrIle
AATGGATCTGGAGTAATTCTTGAAGGTGTAAAAGCTGACAAAAGTAAAGTAAAATTAACAATT
                                                    420

100                   110
SerAspLeuGluGlyGlnThrThrLeuGluValPheLysGluAspGlyLysThrLeuVal
TCTGACGATCTAGAGGTCAAACCACACTTGAAGTTTCAAGAAGATGGCAAACACTAGTA
                                                    480
```

FIG. 7B

```
                    120                                              130
SerLysLysValThrSerLysAspLysSerSerThrGluGluLysPheAsnGluLysGly
TCAAAAAAGTAACTTCCAAGACAAGTCATCAACAGAAGAAAATTCAATGAAAAAGGT          360

140                                              150
GluValSerGluLysGlyLysIleIleIleThrArgAlaAspGlyTrpArgLeuGluIleTyrThrGlyIle
GAAGTATCTGAAAAATATAACAAGAGCAGATGGCAGACTTGAATACACAGGAATT           600

160                                              170
LysSerAspGlySerGlyLysAlaLysLeuLysGlyValLeuGluGlyTyrValLeuGluGlyThr
AAAAGCGATCTCGAAAAGCTAAAGAGGTTTTAAAGGCTATGTTCTTGAAGGAACT           660

180                                              190
LeuThrAlaGluLysThrLeuValValLysGluGlyThrValIleLeuSerLysAsn
CTAACTGCTGAAAAAACATTGGTTGTTAAGGAAGGTACTGTTACTTTAAGCAAAAT           720
```

```
                                                                      210
IleSerLysSerGlyGluValSerValGluLeuAsnAspThrAspSerSerAlaAlaThr
ATTTCAAAATCTGGGGAAGTTTCAGTTGAACTTAATGACACTGACAGTTCTGCTACT
        200                                                          730

230
LysLysThrAlaAlaTrpAsnSerGlyThrSerThrLeuThrIleThrValAsnSerLys
AAAAAACTTGCAGCTTGGAATTCAGGCACTTCAACTTTAACAATTACTGTAAACAGTAAA
        220                                                          840

250
LysThrLysAspLeuValPheThrLysGluAsnThrIleThrValGlnGlnTyrAspSer
AAAACTAAAGACCTTGTTTTACAAAGAAAACACAATTACAGTACAACAATACGACTCA
        240                                                          900

270
AsnGlyThrLysLeuGluGlySerAlaValGluIleIleThrLysLeuLysGluIleLysAsn
AATGGCACCAAATTAGAGGGGTCAGCAGTTGAAATTATTACAAAACTTGAATTAAAAAAC
        260                                                          965
───────►
 Kpn I
```

OspB----->
                   1                              MetArgLeuLeuLeuIleGlyPheAlaAlaLeuLeuAlaLeu
AlaLeuLys---                                                                              10
GCTTTAAAATAAGGAGATTTAATGAGATTATTAATAGGATTTGCTGCTTTAGCGTTACTTTA
                  RBS                                                              1020
                  Xba I
         ↓                  20                                30
         IleGlyCysAlaGlnLysGlyAlaGluSerIleGlyGlySerGlnLysGluAsnAspLeuAsn
ATAGGATGTGCACAAAAAGGTGCTGAGTCAATTGGTGGTTCTCAAAAAGAAAATGATCTAAAC
                                                                                   1080
                      40                               50
         LeuGluAspSerSerLysSerHisGlnAsnAlaLysGlnAsnAspLeuProAlaValThr
CTTGAAGACTCTAGTAAAAGCATCACATCAAACGCTAAACAAAACGATCTTCCGGCTGTGACA
                                                                                   1140
                         60                               70
         GluAspSerValSerLeuPheAsnGlyAsnLysIlePheValSerLysGluLysAsnSer
GAAGACTCAGTTTCTTTGTTTAATGGTAATAAAATTTTTGTTAGCAAAGAAAAAAATAGC
                                                                                   1200

FIG. 7E

```
                           80                                              90
SerGlyLysTyrAspLeuArgAlaThrIleAspGlnValGluLeuLysGlyThrGlySerAsp
TCCGGAAATATGATTAAGACCAATCAATTGATTCAGGTTGAACTTAAGGACTTCCGAT
                                                                        1260

100                                             110
LysAsnAsnGlySerGlyThrLeuGluGluGlySerLysProAspLysSerLysValLysLeu
AAAACAATGGTTCTGGAACCCTTGAAGGTTCAAAGCCTGACAAGAGTAAAGTAAAATTA
                                                                        1320

120                                             130
ThrValSerAlaAspLeuLeuAsnThrValThrLeuGluLeuAlaPheAspAlaSerAsnGlnLys
ACAGTTTCTGCTGATTTGCTGAACACAGTAACCTTAGAACTTGATGCATCCAACCAAAAA
                                                                        1380

140                                             150
IleSerSerLysLysLysValThrLysLysGlyGlnGlySerIleThrGluThrLeuLysAlaAsn
ATTTCAAGTAAGAAGAAAGTTACTAAAAACAGGGGTCAATAACAGAGGAACTCTCAAGCTAAT
                                                                        1440
```

*FIG. 7F*

```
        160                           170
LysLeuAspSerLysLysLeuThrArgSerAsnGlyThrThrLeuGluThrSerGlnIle
AAATTAGACTCAAAGAAATTAACAAGATCAAACGGAACTACAACTTGAAACTTCACAAATA    1500

180                           190
ThrAspAlaAspAsnAlaThrLysAlaValGluThrLeuLysAsnSerIleLysLeuGlu
ACAGATGCTGACAATGCTACAAAAGCTAGAAACTCTAAAAAATCTAAAATTAAGATTAAGCTTGAA    1560

200                           210
GlySerLeuValAlaValGlyLysThrThrValGluIleLysGluGlyThrValThrLeuLys
GGAAGTCTTGTAGTCGGAAAAACAACAGTGGAAATTAAAGAAGGTACTGTTACTCTAAAA    1620

220                           230
ArgGluIleGluLysAspGlyLysValLysValPheLeuAsnAspThrAlaGlySerAsn
AGAGAAATTGAAAAGATGGAAAAGTAAAGTCTTTTTGAATGACACTGCAGGTTCTAAC    1680
```

*FIG. 7G*

```
                    240                          250
LysLysGlyLysTrpGluAspSerThrThrLeuThrIleSerAlaAspSerLys
AAAAAAGGTAAATGGGAAGACAGTACTACTTTAACAATTAGTGCTGACAAA      1740

260                          270
LysThrLysAspLeuValPheLeuIleThrAspGlyThrIleThrValGlnGlnTyrAsnThr
AAACTAAAGGATCTTGTCTTCTTAACAGATGGTACAATTACAGTACAACATACAACACA    1800

280                          290
AlaGlyThrSerLeuGluGlyLysSerAlaSerGluIleIleLysAsnLeuSerGluLeuLeuLysAsn
GCTGGAACCAGCCTAGAAGGATCAGCAAGTGAAATTATAAAATCTTTCAGAGTTACTAAAAAC  1860

AlaLeuLys***
CCTTTAAAATAATATATTAGTAACCCCTACAAGGCATCAGCTAGTGTAGGAAG
                                    ←----
                    ----→
                   BamHI
```

3' IE Acceptor Site

```
                                    Pst    Sal1
1841  GTTCCTCTTTCCATGGGTCTCTTTCTGCAGTCACCCTCGTCGA
      CAAGGAAGGTACCCAGAGAAAGACGTCAGTGGGCAGCT

Pml1  Bcl1  EcoRV  Hot1  Xba1  BstHI  Nar1
1881  CACGTGTGATCAGATATCGCGGCCGCTCTAGACCAGGCGC
      GTGCACACTAGTCTATAGCGCCGGCGAGATCTGGTCCGCG

1921  CTGGATCCAGATCTGTGCCTTCTAGTTGCCAGCCATC
      GACCTAGGTCTAGACACGGAAGATCAACGGTCGGTAG

1961  TGTTGTTTGCCCTCCCCCCGTGCCCTTCCTTGACCCCTGGAA
      ACAACAAACGGGAGGGGGGCACGGGAAGGAACTGGGACCTT
2001  G  BamHI  Bgl2
```

VR1012 Sequence

```
CTCGCGCGTTTCGGTGATGACGGTGAAAACCTCTGACACATGCAGCTCCCGGA
GACGGTCACAGCTTGTCTGTAAGCGGATGCCGGGAGCAGACAAGCCCGTCAG
GGCGCGTCAGCGGGTGTTGGCGGGTGTCGGGGCTGGCTTAACTATGCGGCAT
CAGAGCAGATTGTACTGAGAGTGCACCATATGCGGTGTGAAATACCGCACAGA
TGCGTAAGGAGAAAATACCGCATCAGATTGGCTATTGGCCATTGCATACGTTGT
ATCCATATCATAATATGTACATTTATATTGGCTCATGTCCAACATTACCGCCATG
TTGACATTGATTATTGACTAGTTATTAATAGTAATCAATTACGGGGTCATTAGTT
CATAGCCCATATATGGAGTTCCGCGTTACATAACTTACGGTAAATGGCCCGCCT
GGCTGACCGCCCAACGACCCCCGCCCATTGACGTCAATAATGACGTATGTTCC
CATAGTAACGCCAATAGGGACTTTCCATTGACGTCAATGGGTGGAGTATTTACG
GTAAACTGCCCACTTGGCAGTACATCAAGTGTATCATATGCCAAGTACGCCCCC
TATTGACGTCAATGACGGTAAATGGCCCGCCTGGCATTATGCCCAGTACATGAC
CTTATGGGACTTTCCTACTTGGCAGTACATCTACGTATTAGTCATCGCTATTACC
ATGGTGATGCGGTTTTGGCAGTACATCAATGGGCGTGGATAGCGGTTTGACTC
ACGGGGATTTCCAAGTCTCCACCCCATTGACGTCAATGGGAGTTTGTTTTGGCA
CCAAAATCAACGGGACTTTCCAAAATGTCGTAACAACTCCGCCCCATTGACGCA
AATGGGCGGTAGGCGTGTACGGTGGGAGGTCTATATAAGCAGAGCTCGTTTAG
TGAACCGTCAGATCGCCTGGAGACGCCATCCACGCTGTTTTGACCTCCATAGAA
GACACCGGGACCGATCCAGCCTCCGCGGCCGGGAACGGTGCATTGGAACGCG
GATTCCCCGTGCCAAGAGTGACGTAAGTACCGCCTATAGAGTCTATAGGCCCA
CCCCCTTGGCTTCTTATGCATGCTATACTGTTTTTGGCTTGGGGTCTATACACCC
CCGCTTCCTCATGTTATAGGTGATGGTATAGCTTAGCCTATAGGTGTGGGTTAT
TGACCATTATTGACCACTCCCCTATTGGTGACGATACTTTCCATTACTAATCCAT
AACATGGCTCTTTGCCACAACTCTCTTTATTGGCTATATGCCAATACACTGTCCT
TCAGAGACTGACACGGACTCTGTATTTTTACAGGATGGGGTCTCATTTATTATTT
ACAAATTCACATATACAACACCACCGTCCCCAGTGCCCGCAGTTTTTATTAAACA
TAACGTGGGATCTCCACGCGAATCTCGGGTACGTGTTCCGGACATGGGCTCTT
CTCCGGTAGCGGCGGAGCTTCTACATCCGAGCCCTGCTCCCATGCCTCCAGCG
ACTCATGGTCGCTCGGCAGCTCCTTGCTCCTAACAGTGGAGGCCAGACTTAGG
CACAGCACGATGCCCACCACCACCAGTGTGCCGCACAAGGCCGTGGCGGTAG
GGTATGTGTCTGAAAATGAGCTCGGGGAGCGGGCTTGCACCGCTGACGCATTT
GGAAGACTTAAGGCAGCGGCAGAAGAAGATGCAGGCAGCTGAGTTGTTGTGT
TCTGATAAGAGTCAGAGGTAACTCCCGTTGCGGTGCTGTTAACGGTGGAGGGC
AGTGTAGTCTGAGCAGTACTCGTTGCTGCCGCGCGCGCCACCAGACATAATAG
CTGACAGACTAACAGACTGTTCCTTTCCATGGGTCTTTTCTGCAGTCACCGTCG
TCGACACGTGTGATCAGATATCGCGGCCGCTCTAGACCAGGCGCCTG
GATCCAGATCTGCTGTGCCTTCTAGTTGCCAGCCATCTGTTGTTTGCCCCTCC
CCCGTGCCTTCCTTGACCCTGGAAGGTGCCACTCCCACTGTCCTTTCCTAATAA
AATGAGGAAATTGCATCGCATTGTCTGAGTAGGTGTCATTCTATTCTGGGGGGT
GGGGTGGGGCAGCACAGCAAGGGGGAGGATTGGGAAGACAATAGCAGGCAT
GCTGGGGATGCGGTGGGCTCTATGGGTACCCAGGTGCTGAAGAATTGACCCG
GTTCCTCCTGGGCCAGAAAGAAGCAGGCACATCCCCTTCTCTGTGACACACCCT
GTCCACGCCCCTGGTTCTTAGTTCCAGCCCCACTCATAGGACACTCATAGCTCA
GGAGGGCTCCGCCTTCAATCCCACCCGCTAAAGTACTTGGAGCGGTCTCTCCC
TCCCTCATCAGCCCACCAAACCAAACCTAGCCTCCAAGAGTGGGAAGAAATTAA
AGCAAGATAGGCTATTAAGTGCAGAGGGAGAGAAAATGCCTCCAACATGTGAG
GAAGTAATGAGAGAAATCATAGAATTTCTTCCGCTTCCTCGCTCACTGACTCGC
TGCGCTCGGTCGTTCGGCTGCGGCGAGCGGTATCAGCTCACTCAAAGGCGGTA
ATACGGTTATCCACAGAATCAGGGGATAACGCAGGAAAGAACATGTGAGCAAA
AGGCCAGCAAAAGGCCAGGAACCGTAAAAAGGCCGCGTTGCTGGCGTTTTTCC
ATAGGCTCCGCCCCCCTGACGAGCATCACAAAAATCGACGCTCAAGTCAGAGG
```

FIG. IOA

```
TGGCGAAACCCGACAGGACTATAAAGATACCAGGCGTTTCCCCCTGGAAGCTC
CCTCGTGCGCTCTCCTGTTCCGACCCTGCCGCTTACCGGATACCTGTCCGCCTT
TCTCCCTTCGGGAAGCGTGGCGCTTTCTCAATGCTCACGCTGTAGGTATCTCAG
TTCGGTGTAGGTCGTTCGCTCCAAGCTGGGCTGTGTGCACGAACCCCCCGTTC
AGCCCGACCGCTGCGCCTTATCCGGTAACTATCGTCTTGAGTCCAACCCGGTAA
GACACGACTTATCGCCACTGGCAGCAGCCACTGGTAACAGGATTAGCAGAGCG
AGGTATGTAGGCGGTGCTACAGAGTTCTTGAAGTGGTGGCCTAACTACGGCTA
CACTAGAAGGACAGTATTTGGTATCTGCGCTCTGCTGAAGCCAGTTACCTTCGG
AAAAAGAGTTGGTAGCTCTTGATCCGGCAAACAAACCACCGCTGGTAGCGGTG
GTTTTTTTGTTTGCAAGCAGCAGATTACGCGCAGAAAAAAAGGATCTCAAGAAG
ATCCTTTGATCTTTTCTACGGGGTCTGACGCTCAGTGGAACGAAAACTCACGTT
AAGGGATTTTGGTCATGAGATTATCAAAAAGGATCTTCACCTAGATCCTTTTAAA
TTAAAAATGAAGTTTTAAATCAATCTAAAGTATATATGAGTAAACTTGGTCTGAC
AGTTACCAATGCTTAATCAGTGAGGCACCTATCTCAGCGATCTGTCTATTTCGTT
CATCCATAGTTGCCTGACTCCGGGGGGGGGGGCGCTGAGGTCTGCCTCGTG
AAGAAGGTGTTGCTGACTCATACCAGGCCTGAATCGCCCCATCATCCAGCCAG
AAAGTGAGGGAGCCACGGTTGATGAGAGCTTTGTTGTAGGTGGACCAGTTGGT
GATTTTGAACTTTTGCTTTGCCACGGAACGGTCTGCGTTGTCGGGAAGATGCGT
GATCTGATCCTTCAACTCAGCAAAAGTTCGATTTATTCAACAAAGCCGCCGTCC
CGTCAAGTCAGCGTAATGCTCTGCCAGTGTTACAACCAATTAACCAATTCTGAT
TAGAAAAACTCATCGAGCATCAAATGAAACTGCAATTTATTCATATCAGGATTAT
CAATACCATATTTTTGAAAAAGCCGTTTCTGTAATGAAGGAGAAAACTCACCGA
GGCAGTTCCATAGGATGGCAAGATCCTGGTATCGGTCTGCGATTCCGACTCGT
CCAACATCAATACAACCTATTAATTTCCCCTCGTCAAAAATAAGGTTATCAAGTG
AGAAATCACCATGAGTGACGACTGAATCCGGTGAGAATGGCAAAAGCTTATGC
ATTTCTTTCCAGACTTGTTCAACAGGCCAGCCATTACGCTCGTCATCAAAATCAC
TCGCATCAACCAAACCGTTATTCATTCGTGATTGCGCCTGAGCGAGACGAAATA
CGCGATCGCTGTTAAAAGGACAATTACAAACAGGAATCGAATGCAACCGGCGC
AGGAACACTGCCAGCGCATCAACAATATTTTCACCTGAATCAGGATATTCTTCT
AATACCTGGAATGCTGTTTTCCCGGGGATCGCAGTGGTGAGTAACCATGCATC
ATCAGGAGTACGGATAAAATGCTTGATGGTCGGAAGAGGCATAAATTCCGTCA
GCCAGTTTAGTCTGACCATCTCATCTGTAACATCATTGGCAACGCTACCTTTGCC
ATGTTTCAGAAACAACTCTGGCGCATCGGGCTTCCCATACAATCGATAGATTGT
CGCACCTGATTGCCCGACATTATCGCGAGCCCATTTATACCCATATAAATCAGC
ATCCATGTTGGAATTTAATCGCGGCCTCGAGCAAGACGTTTCCCGTTGAATATG
GCTCATAACACCCCTTGTATTACTGTTTATGTAAGCAGACAGTTTTATTGTTCAT
GATGATATATTTTTATCTTGTGCAATGTAACATCAGAGATTTTGAGACACAACGT
GGCTTTCCCCCCCCCCCATTATTGAAGCATTTATCAGGGTTATTGTCTCATGAG
CGGATACATATTTGAATGTATTTAGAAAAATAAACAAATAGGGGTTCCGCGCAC
ATTTCCCCGAAAAGTGCCACCTGACGTCTAAGAAACCATTATTATCATGACATTA
ACCTATAAAAATAGGCGTATCACGAGGCCCTTTCGTC
```

FIG. 10B nkCMVintBL Sequence

```
AAGCTTTTTTTGCAAAAGCCTAGGCCTCCAAAAAAGCCTCCTCACTACTTCTGG
AATAGCTCAGAGGCCGAGGCGGCCTCGGCCTCTGCATAAATAAAAAAAAT
TAGTCAGCCATGGGGCGGAGAATGGGCGGAACTGGGCGAAGTTAGGGGC
GGGATGGGCGGAGTGAATTATTGGCTATTGGCCATTGCATACGTTGTATCT
ATATCATAATATGTACATTTATATTGGCTCATGTCCAATATGACCGCCATGT
TGACATTGATTATTGACTAGTTATTAATAGTAATCAATTACGGGGTCATTAG
TTCATAGCCCATATATGGAGTTCCGCGTTACATAACTTACGGTAATTGGCC
CGCCTGCTGACCGCCCAACGACCCCCGCCCATTGACGTCAATAATGACGT
ATGTTCCCATAGTAACGCCAATAGGGACTTTCCATTGACGTCAATGGGTGG
AGTATTTACGGTAAACTGCCCACTTGGCAGTACATCAAGTGTATCATATGC
CAAGTCCGGCCCCCTATTGACGTCAATGACGGTAAATGGCCCGCCTGGCA
TTATGCCCAGTACATGACCTTACGGGACTTTGGTACTTGGCAGTACATCTA
CGTATTAGTCATCGCTATTACCATGGTGATGCGGTTTTGGCAGTACACCAA
TGGGCGTGGATAGCGGTTTGACTCACGGGGATTTCCAAGTCTCCACCCCA
TTGACGTCAATGGGAGTTTGTTTTGGCACCAAAATCAACGGGACTTTCCAA
AATGTCGTAATAACCCCGCCCCGTTGACGCAAATGGGCGGTAGGCGTGTA
CGGTGGGAGGTCTATATAAGCAGAGCTCGTTTAGTGAACCGTCAGATCGC
CTGGAGACGCCATCCACGCTGTTTTGACCTCCATAGAAGACACCGGGACC
GATCCAGCCTCCGCGGCCGGGAACGGTGCATTGGAACGCGGATTCCCCGT
GCCAAGAGTGACGTAAGTACCGCCTATAGACTCTATAGGCACACCCCTTTG
GCTCTTATGCATGCTATACTGTTTTTGGCTTGGGGCCTATACACCCCGCTC
CTTATGCTATAGGTGATGGTATAGCTTAGCCTATAGGTGTGGGTTATTGAC
CATTATTGACCACTCCCCTATTGGTGACGATACTTTCCATTACTAATCCATA
ACATGGCTCTTTGCCACAACTATCTCTATTGGCTATATGCCAATACTCTGTC
CTTCAGAGACTGACACGGACTCTGTATTTTTACAGGATGGGGTCCCATTTA
TTATTTACAAATTCACATATACAACAACGCCGTCCCCCGTGCCCGCAGTTTT
TATTAAACATAGCGTGGGATCTCCACGCGAATCTCGGGTACGTGTTCCGGA
CATGGGCTCTTCTCCGGTAGCGGCGGAGCTTCCACATCCGAGCCCTGGTC
CCATGCCTCCAGCGGCTCATGGTCGCTCGGCAGCTCCTTGCTCCTAACAGT
GGAGGCCAGACTTAGGCACAGCACAATGCCCACCACCACCAGTGTGCCGC
ACAAGGCCGTGGCGGTAGGGTATGTGTCTGAAAATGAGCTCGGAGATTGG
GCTCGCACCGTGACGCAGATGGAAGACTTAAGGCAGCGGCAGAAGAAGA
TGCAGGCAGCTGAGTTGTTGTATTCTGATAAGAGTCAGAGGTAACTCCCGT
TGCGGTTCTGTTAACGGTGGAGGGCAGTGTAGTCTGAGCAGTACTCGTTG
CTGCCGCGCGCGCCACCAGACATAATAGCTGACAGACTAACAGACTGTTC
CTTTCCATGGGTCTTTTCTGCAGTCACCGTCGTCGACCAGAGCTGAGATCC
TACAGGAGTCCAGGGCTGGAGAGAAAACCTCTGCGAGGAAAGGGAAGGA
GCAAGCCGTGAATTTAAGGGACGCTGTGAAGCAATCATGGATGCAATGAA
GAGAGGGCTCTGCTGTGTGCTGCTGCTGTGTGGAGCAGTCTTCGTTTCGC
CCAGCGCTAGAGGATCCAGATCTCTCGACATGGGCAAATATTATACGCAA
GGCGACAAGGTGCTGATGCCGCTGGCGATTCAGGTTCATCATGCCGTCTG
TGATGGCTTCCATGTCGGCAGAATGCTTAATGAATTACAACAGTACTGCGA
TGAGTGGCAGGGCGGGGCGTAATTTTTTTAAGGCAGTTATTGGTGCCCTTA
AACGCCTGGTGCTACGCCTGAATAAGTGATAATAAGCGGATGAATGGCAG
AAATTCGCCGGATCTTTGTGAAGGAACCTTACTTCTGTGGTGTGACATAAT
TGGACAAACTACCTACAGAGATTTAAAGCTCTAAGGTAAATATAAAATTTTT
AAGTGTATAATGTGTTAAACTACTGATTCTAATTGTTTGTGTATTTTAGATTC
CAACCTATGGAACTGATGAATGGGAGCAGTGGTGGAATGCCTTTAATGAG
GAAAACCTGTTTTGCTCAGAAGAAATGCCATCTAGTGATGATGAGGCTACT
GCTGACTCTCAACATTCTACTCCTCCAAAAAAGAAGAGAAAGGTAGAAGAC
```

FIG. 11A

```
CCCAAGGACTTTCCTTCAGAATTGCTAAGTTTTTTGAGTCATGCTGTGTTTA
GTAATAGAACTCTTGCTTGCTTTGCTATTTACACCACAAAGGAAAAAGCTG
CACTGCTATACAAGAAAATTATGGAAAAATATTCTGTAACCTTTATAAGTAG
GCATAACAGTTATAATCATAACATACTGTTTTTTCTTACTCCACACAGGCAT
AGAGTGTCTGCTATTAATAACTATGCTCAAAAATTGTGTACCTTTAGCTTTT
TAATTTGTAAAGGGGTTAATAAGGAATATTTGATGTATAGTGCCTTGACTA
GAGATCATAATCAGCCATACCACATTTGTAGAGGTTTTACTTGCTTTAAAAA
ACCTCCCACACCTCCCCCTGAACCTGAAACATAAAATGAATGCAATTGTTG
TTGTTAACTTGTTTATTGCAGCTTATAATGGTTACAAATAAAGCAATAGCAT
CACAAATTTCACAAATAAAGCATTTTTTTCACTGCATTCTAGTTGTGGTTTGT
CCAAACTCATCAATGTATCTTATCATGTCTGGATCGATCCCCGGGTACCGA
GCTCGAATTCGTAATCATGGTCATAGCTGTTTCCTGTGTGAAATTGTTATCC
GCTCACAATTCCACACAACATACGAGCCGGAAGCATAAAGTGTAAAGCCT
GGGGTGCCTAATGAGTGAGCTAACTCACATTAATTGCGTTGCGCTCACTGC
CCGCTTTCCAGTCGGGAAACCTGTCGTGCCAGCTGCATTAATGAATCGGCC
AACGCGCGGGGAGAGGCGGTTTGCGTATTGGGCGCTCTTCCGCTTCCTCG
CTCACTGACTCGCTGCGCTCGGTCGTTCGGCTGCGGCGAGCGGTATCAGC
TCACTCAAAGGCGGTAATACGGTTATCCACAGAATCAGGGGATAACGCAG
GAAAGAACATGTGAGCAAAAGGCCAGCAAAAGGCCAGGAACCGTAAAAA
GGCCGCGTTGCTGGCGTTTTTCCATAGGCTCCGCCCCCCTGACGAGCATC
ACAAAAATCGACGCTCAAGTCAGAGGTGGCGAAACCCGACAGGACTATAA
AGATACCAGGCGTTTCCCCCTGGAAGCTCCCTCGTGCGCTCTCCTGTTCCG
ACCCTGCCGCTTACCGGATACCTGTCCGCCTTTCTCCCTTCGGGAAGCGTG
GCGCTTTCTCATAGCTCACGCTGTAGGTATCTCAGTTCGGTGTAGGTCGTT
CGCTCCAAGCTGGGCTGTGTGCACGAACCCCCGTTCAGCCCGACCGCTG
CGCCTTATCCGGTAACTATCGTCTTGAGTCCAACCCGGTAAGACACGACTT
ATCGCCACTGGCAGCAGCCACTGGTAACAGGATTAGCAGAGCGAGGTATG
TAGGCGGTGCTACAGAGTTCTTGAAGTGGTGGCCTAACTACGGCTACACT
AGAAGGACAGTATTTGGTATCTGCGCTCTGCTGAAGCCAGTTACCTTCGGA
AAAAGAGTTGGTAGCTCTTGATCCGGCAAACAAACCACCGCTGGTAGCGG
TGGTTTTTTTGTTTGCAAGCAGCAGATTACGCGCAGAAAAAAAGGATCTCA
AGAAGATCCTTTGATCTTTTCTACGGGGTCTGACGCTCAGTGGAACGAAAA
CTCACGTTAAGGGATTTTGGTCATGAACAATAAAACTGTCTGCTTACATAAA
CAGTAATACAAGGGGTGTTATGAGCCATATTCAACGGGAAACGTCTTGCTC
GAGGCCGCGATTAAATTCCAACATGGATGCTGATTTATATGGGTATAAATG
GGCTCGCGATAATGTCGGGCAATCAGGTGCGACAATCTATCGATTGTATG
GGAAGCCCGATGCGCCAGAGTTGTTTCTGAAACATGGCAAAGGTAGCGTT
GCCAATGATGTTACAGATGAGATGGTCAGACTAAACTGGCTGACGGAATTT
ATGCCTCTTCCGACCATCAAGCATTTTATCCGTACTCCTGATGATGCATGGT
TACTCACCACTGCGATCCCCGGGAAAACAGCATTCCAGGTATTAGAAGAAT
ATCCTGATTCAGGTGAAAATATTGTTGATGCGCTGGCAGTGTTCCTGCGCC
GGTTGCATTCGATTCCTGTTTGTAATTGTCCTTTTAACAGCGATCGCGTATT
TCGTCTCGCTCAGGCGCAATCACGAATGAATAACGGTTTGGTTGATGCGA
GTGATTTTGATGACGAGCGTAATGGCTGGCCTGTTGAACAAGTCTGGAAA
GAAATGCATAAGCTTTTGCCATTCTCACCGGATTCAGTCGTCACTCATGGT
GATTTCTCACTTGATAACCTTATTTTTGACGAGGGGAAATTAATAGGTTGTA
TTGATGTTGGACGAGTCGGAATCGCAGACCGATACCAGGATCTTGCCATC
CTATGGAACTGCCTCGGTGAGTTTTCTCCTTCATTACAGAAACGGCTTTTTC
AAAAATATGGTATTGATAATCCTGATATGAATAAATTGCAGTTTCATTTGAT
GCTCGATGAGTTTTTCTAAGAATTCGCCATTCGCCATTCAGGCTGCGCAAC
TGTTGGGAAGGGCGATCGGTGCGGGCCTCTTCGCTATTACGCCAGCTGGC
GAAAGGGGGATGTGCTGCAAGGCGATTAAGTTGGGTAACGCCAGGGTTTT
CCCAGTCACGACGTTGTAAAACGACGGCCAGTGCC
```

```
     Pst1     Sal1
CTGCAGTCACCGTCGTCGACCAGAGCTGAGATCCTACAGGAGTCCAGGGCTGG

AGAGAAACCTCTGCGAGGAAAGGGAGGAAGCAAGCCGTGAATTAAGGGAC

Met Asp Ala Met Lys Arg Gly Leu Cys Cys Val Leu Leu
GCTGTGAAGCAATCATGGATGCAATGAAGAGAGGGCTCTGTGTGTGCTGCTG

Leu Cys Gly Ala Val Phe Val Ser Pro Ser Ala↓Arg  BamH1    Bgl2
CTGTGTGGAGCAGTCTTCGTTTCGCCCAGCGCTAGAGGATCCAGATCTCTCGA
```

Arrow indicates the presumed site of signal peptide cleavage.

FIG. 13

PCR PRIMERS:

FORWARD (SENSE) 5' GCCTTAGGTACCTGTAAGCAAAATGTTAGC 3'
                        —————————  ——————————————————
                         Kpn I site   OspA HOMOLOGOUS SEQUENCE REVERSE (NON-SENSE) 5' TAATAATCTAGAAAAATTCTCCTTACTTAAGAGGCGTTTTAAT 3'
                       ——————————                  ———————————————
                        Xba I                        Afl II    OspA HOME. SEQ.
                        Site                         Site

FIG. 14

PCR PRIMERS:

FORWARD (SENSE) 5' GCTTTT AGGTACCTGTGCACAAAAAGGTGCT 3'
　　　　　　　　　　　　　　‾‾‾‾‾‾‾‾ ‾‾‾‾‾‾‾‾‾‾‾‾‾‾‾‾‾‾‾‾
　　　　　　　　　　　　　　Kpn I Site　OspB HOMOLOGOUS SEQUENCE REVERSE (NON-SENSE) 5' AGGGGGGGGATCCCTATATATTATTTTTAAAGC 3'
　　　　　　　　　　　　　‾‾‾‾‾‾‾‾‾‾‾ ‾‾‾‾‾‾‾‾‾‾‾‾‾‾‾‾‾‾‾‾‾‾
　　　　　　　　　　　　　Bam HI site　OspB HOMOLOGOUS SEQUENCE

FIG. 15

```
                                                            Pst I        TPA 5' UNTRANSLATED
  1  TAGCTGACAG ACTAACAGAC TGTTCCTTTC CATGGTCTT  TTCGCAGTC ACCGTCGTCG
     ATCGACTGTC TGATTGTCTG ACAAGGAAAG GTACCCAGAA  AAGCGTCAG TGGCAGCAGC

TPA LEADER
 61  ACCAGAGCTG AGATCCTACA GGAGTCCAGG GCTGGAGAGA  AAACCTCTGC GAGGAAAGGG
     TGGTCTCGAC TCTAGGATGT CCTCAGGTCC CGACCTCTCT  TTTGGAGACG CTCCTTTCCC

START  ATGAAGAGAG
121  AAGGAGCAAG CCGTGAATTT GTGAAGCAAT CAGTCTTCGT  CATGAATGCA TACTTCTCTC
     TTCCTCGTTC GGCACTTAAA CACTTCGTTA GTCAGAAGCA  GTACTTACGT ATGAAGAGAG
                                                                  rospA
                                                        Kpn I  GGTACC GTA
181  GGCTCTGCTG TGTGCTGCTT CAGTCTTCGT TTCGCCCAGC  GGTACC CCATGGACAT
     CCGAGACGAC ACACGACGAA GTCAGAAGCA AAGCGGGTCG  CCATGGACAT GGACCACTTT
                                                    G  T  C  pos 17

241  AGCAAAATGT TAGCAGCCTT GACGAGAAA ACAGCGTTTC  AGTAGATTTG CCTGGTGAAA
     TCGTTTTACA ATCGTCGGAA CTGCTCTTT TGTCGCAAAG  TCATCTAAAC GGACCACTTT

301  TGAAAGTTCT TGTAAGCAAA GAAAAAACA AAGACGGCAA  GTACGATCTA ATTGCAACAG
     ACTTTCAAGA ACATTCGTTT CTTTTTTGT TTCTGCCGTT  CATGCTAGAT TAACGTTGTC

361  TAGACAAGCT TGAGCTTAAA GGAACTTCTG ATAAAAACAA  TGGATCTGGA GTACTTGAAG
     ATCGTTCGAA ACTCGAATTT CCTTGAAGAC TATTTTTGTT  ACCTAGACCT CATGAACTTC
```

FIG. 16

```
  1  GTACTCGTTG CATGAGCAAC CTGCCGCCGC GACGGCGCGC CGCCACCAGA GCGTGGTCT CATAATAGCT GTATTATCGA GACAGACTAA CTGTCTGATT CAGACTGTTC GTCTGACAAG
                                                  PstI          TPA 5' UNTRANSLATED
 61  CTTCCATGG  GTCTTTCTG  CAGTCACCGT AGCTGAGATC CTACAGGAGT
     GAAGGTACC  CAGAAAAGAC GTCAGTGGCA TCGACTCTAG GATGTCCTCA
                           START TPA LEADER
121  CCAGGGCTGG AGAGAAACC  TCTGCGAGGA AAGGGAAGGA GCAAGCCGTG AATTTAAGGG
     GGTCCCGACC TCTCTTTTGG AGACGCTCCT TTCCCTTCCT CGTTCGGCAC TTAAATTCCC
181  ACGCTGTGAA GCAATGATG  ATGCAATGAA GAGAGGGCTC TGCTGTGTGC TGCTGCTGTG
     TGCGACACTT CGTTAGTACC TACGTTACTT CTCTCCCGAG ACGACACACG ACGACGACAC
                         ↑              KpnI         osp B
241  TGGAGCAGTC TTCGTTTCGC CCAGCGGTAC CTGTGCACAA AAGGTGCTG  AGTCAATTGG
     ACCTCGTCAG AAGCAAAGCG GGTCGCCATG GACACGTGTT TTCCACGAC  TCAGTTAACC
                                       G    T    C  pos 16
301  TTCTCAAAA  GAAAATGATC TAAACCTTGA AGACTCTAGT AAAAAATCAC ATCAAAACGC
     AAGAGTTTTT CTTTTACTAG ATTTGGAACT TCTGAGATCA TTTTTTAGTG TAGTTTTGCG
361  TAAACAAGAC CTTCCTGCGG TGACAGAAGA CTCAGTGTCT CTCAGGAAGA TTGTTTAATG GTAATAAAAT
     ATTTGTTTCTGT CAACCACCCC ACTGTCTTCT GAGTCACAGA GAGTCACAGA AACAAATTAC CATTATTTTA
```

```
   1 TGGCCATTGC ATACGTTGTA TCCATATCAT AATATGTACA TTTATATTGG
  51 CTCATGTCCA ACATTACCGC CATGTTGACA TTGATTATTG ACTAGTTATT
 101 AATAGTAATC AATTACGGGG TCATTAGTTC ATAGCCCATA TATGGAGTTC
 151 CGCGTTACAT AACTTACGGT AAATGGCCCG CCTGGCTGAC CGCCCAACGA
 201 CCCCCGCCCA TTGACGTCAA TAATGACGTA TGTTCCCATA GTAACGCCAA
 251 TAGGGACTTT CCATTGACGT CAATGGGTGG AGTATTTACG GTAAACTGCC
 301 CACTTGGCAG TACATCAAGT GTATCATATG CCAAGTACGC CCCTATTGA
 351 CGTCAATGAC GGTAAATGGC CCGCCTGGCA TTATGCCCAG TACATGACCT
 401 TATGGGACTT TCCTACTTGG CAGTACATCT ACGTATTAGT CATCGCTATT
 451 ACCATGGTGA TGCGGTTTTG GCAGTACATC AATGGGCGTG GATAGCGGTT
 501 TGACTCACGG GGATTTCCAA GTCTCCACCC CATTGACGTC AATGGGAGTT
 551 TGTTTTGGCA CCAAAATCAA CGGGACTTTC CAAAATGTCG TAACAACTCC
 601 GCCCCATTGA CGCAAATGGG CGGTAGGCGT GTACGGTGGG AGGTCTATAT
 651 AAGCAGAGCT CGTTTAGTGA ACCGTCAGAT CGCCTGGAGA CGCCATCCAC
 701 GCTGTTTTGA CCTCCATAGA AGACACCGGG ACCGATCCAG CCTCCGCGGC
 751 CGGGAACGGT GCATTGGAAC GCGGATTCCC CGTGCCAAGA GTGACGTAAG
 801 TACCGCCTAT AGAGTCTATA GGCCCACCCC CTTGGCTTCT TATGCATGCT
 851 ATACTGTTTT TGGCTTGGGG TCTATACACC CCCGCTTCCT CATGTTATAG
 901 GTGATGGTAT AGCTTAGCCT ATAGGTGTGG GTTATTGACC ATTATTGACC
 951 ACTCCCCTAT TGGTGACGAT ACTTTCCATT ACTAATCCAT AACATGGCTC
1001 TTTGCCACAA CTCTCTTTAT TGGCTATATG CCAATACACT GTCCTTCAGA
1051 GACTGACACG GACTCTGTAT TTTTACAGGA TGGGGTCTCA TTTATTATTT
1101 ACAAATTCAC ATATACAACA CCACCGTCCC CAGTGCCCGC AGTTTTTATT
1151 AAACATAACG TGGGATCTCC ACGCGAATCT CGGGTACGTG TTCCGGACAT
1201 GGGCTCTTCT CCGGTAGCGG CGGAGCTTCT ACATCCGAGC CCTGCTCCCA
1251 TGCCTCCAGC GACTCATGGT CGCTCGGCAG CTCCTTGCTC CTAACAGTGG
1301 AGGCCAGACT TAGGCACAGC ACGATGCCCA CCACCACCAG TGTGCCGCAC
1351 AAGGCCGTGG CGGTAGGGTA TGTGTCTGAA AATGAGCTCG GGGAGCGGGC
1401 TTGCACCGCT GACGCATTTG GAAGACTTAA GGCAGCGGCA GAAGAAGATG
1451 CAGGCAGCTG AGTTGTTGTG TTCTGATAAG AGTCAGAGGT AACTCCCGTT
1501 GCGGTGCTGT TAACGGTGGA GGGCAGTGTA GTCTGAGCAG TACTCGTTGC
1551 TGCCGCGCGC GCCACCAGAC ATAATAGCTG ACAGACTAAC AGACTGTTCC
1601 TTTCCATGGG TCTTTTCTGC AGTCACCGTC GTCGACCAGA GCTGAGATCC
1651 TACAGGAGTC CAGGGCTGGA GAGAAAACCT CTGCGAGGAA AGGGAAGGAG
1701 CAAGCCGTGA ATTTAAGGGA CGCTGTGAAG CAATCATGGA TGCAATGAAG
1751 AGAGGGCTCT GCTGTGTGCT GCTGCTGTGT GGAGCAGTCT TCGTTTCGCC
1801 CAGCGGTACC TGTAATAATT CAGGGAAAGA TGGGAATACA TCTGCAAATT
1851 CTGCTGATGA GTCTGTTAAA GGGCCTAATC TTACAGAAAT AAGTAAAAAA
1901 ATTACGGATT CTAATGCGGT TTTACTTGCT GTGAAAGAGG TTGAAGCGTT
1951 GCTGTCATCT ATAGATGAAA TTGCTGCTAA AGCTATTGGT AAAAAAATAC
2001 ACCAAAATAA TGGTTTGGAT ACCGAAAATA ATCACAATGG ATCATTGTTA
2051 GCGGGAGCTT ATGCAATATC AACCCTAATA AAACAAAAAT TAGATGGATT
2101 GAAAAATGAA GGATTAAAGG AAAAAATTGA TGCGGCTAAG AAATGTTCTG
2151 AAACATTTAC TAATAAATTA AAGAAAAAC ACACAGATCT TGGTAAAGAA
2201 GGTGTTACTG ATGCTGATGC AAAAGAAGCG ATTTTAAAAA CAAATGGTAC
2251 TAAAACTAAA GGTGCTGAAG AACTTGGAAA ATTATTTGAA TCAGTAGAGG
2301 TCTTGTCAAA AGCAGCTAAA GAGATGCTTG CTAATTCAGT TAAAGAGCTT
2351 ACAAGCCCTG TTGTGGCAGA AAGTCCAAAA AAACCTTAAG GATCCAGATC
2401 TGCTGTGCCT TCTAGTTGCC AGCCATCTGT TGTTTGCCCC TCCCCCGTGC
2451 CTTCCTTGAC CCTGGAAGGT GCCACTCCCA CTGTCCTTTC CTAATAAAAT
2501 GAGGAAATTG CATCGCATTG TCTGAGTAGG TGTCATTCTA TTCTGGGGGG
2551 TGGGGTGGGG CAGCACAGCA AGGGGGAGGA TTGGGAAGAC AATAGCAGGC
2601 ATGCTGGGGA TGCGGTGGGC TCTATGGGGA CCCAGGTGCT GAAGAATTGA
2651 CCCGGTTCCT CCTGGGCCAG AAAGAAGCAG GCACATCCCC TTCTCTGTGA
2701 CACACCCTGT CCACGCCCCT GGTTCTTAGT TCCAGCCCCA CTCATAGGAC
```

```
2751 ACTCATAGCT CAGGAGGGCT CCGCCTTCAA TCCCACCCGC TAAAGTACTT
2801 GGAGCGGTCT CTCCCTCCCT CATCAGCCCA CCAAACCAAA CCTAGCCTCC
2851 AAGAGTGGGA AGAAATTAAA GCAAGATAGG CTATTAAGTG CAGAGGGAGA
2901 GAAAATGCCT CCAACATGTG AGGAAGTAAT GAGAGAAATC ATAGAATTTC
2951 TTCCGCTTCC TCGCTCACTG ACTCGCTGCG CTCGGTCGTT CGGCTGCGGC
3001 GAGCGGTATC AGCTCACTCA AAGGCGGTAA TACGGTTATC CACAGAATCA
3051 GGGGATAACG CAGGAAAGAA CATGTGAGCA AAAGGCCAGC AAAAGGCCAG
3101 GAACCGTAAA AAGGCCGCGT TGCTGGCGTT TTTCCATAGG CTCCGCCCCC
3151 CTGACGAGCA TCACAAAAAT CGACGCTCAA GTCAGAGGTG GCGAAACCCG
3201 ACAGGACTAT AAAGATACCA GGCGTTTCCC CCTGGAAGCT CCCTCGTGCG
3251 CTCTCCTGTT CCGACCCTGC CGCTTACCGG ATACCTGTCC GCCTTTCTCC
3301 CTTCGGGAAG CGTGGCGCTT TCTCAATGCT CACGCTGTAG GTATCTCAGT
3351 TCGGTGTAGG TCGTTCGCTC CAAGCTGGGC TGTGTGCACG AACCCCCCGT
3401 TCAGCCCGAC CGCTGCGCCT TATCCGGTAA CTATCGTCTT GAGTCCAACC
3451 CGGTAAGACA CGACTTATCG CCACTGGCAG CAGCCACTGG TAACAGGATT
3501 AGCAGAGCGA GGTATGTAGG CGGTGCTACA GAGTTCTTGA AGTGGTGGCC
3551 TAACTACGGC TACACTAGAA GGACAGTATT TGGTATCTGC GCTCTGCTGA
3601 AGCCAGTTAC CTTCGGAAAA AGAGTTGGTA GCTCTTGATC CGGCAAACAA
3651 ACCACCGCTG GTAGCGGTGG TTTTTTGTT TGCAAGCAGC AGATTACGCG
3701 CAGAAAAAAA GGATCTCAAG AAGATCCTTT GATCTTTTCT ACGGGGTCTG
3751 ACGCTCAGTG GAACGAAAAC TCACGTTAAG GGATTTTGGT CATGAGATTA
3801 TCAAAAGGA TCTTCACCTA GATCCTTTTA AATTAAAAAT GAAGTTTTAA
3851 ATCAATCTAA AGTATATATG AGTAAACTTG GTCTGACAGT TACCAATGCT
3901 TAATCAGTGA GGCACCTATC TCAGCGATCT GTCTATTTCG TTCATCCATA
3951 GTTGCCTGAC TCCGGGGGGG GGGGCGCTG AGGTCTGCCT CGTGAAGAAG
4001 GTGTTGCTGA CTCATACCAG GCCTGAATCG CCCCATCATC CAGCCAGAAA
4051 GTGAGGGAGC CACGGTTGAT GAGAGCTTTG TTGTAGGTGG ACCAGTTGGT
4101 GATTTTGAAC TTTTGCTTTG CCACGGAACG GTCTGCGTTG TCGGGAAGAT
4151 GCGTGATCTG ATCCTTCAAC TCAGCAAAAG TTCGATTTAT TCAACAAAGC
4201 CGCCGTCCCG TCAAGTCAGC GTAATGCTCT GCCAGTGTTA CAACCAATTA
4251 ACCAATTCTG ATTAGAAAAA CTCATCGAGC ATCAAATGAA ACTGCAATTT
4301 ATTCATATCA GGATTATCAA TACCATATTT TTGAAAAAGC CGTTTCTGTA
4351 ATGAAGGAGA AAACTCACCG AGGCAGTTCC ATAGGATGGC AAGATCCTGG
4401 TATCGGTCTG CGATTCCGAC TCGTCCAACA TCAATACAAC CTATTAATTT
4451 CCCCTCGTCA AAAATAAGGT TATCAAGTGA GAAATCACCA TGAGTGACGA
4501 CTGAATCCGG TGAGAATGGC AAAAGCTTAT GCATTTCTTT CCAGACTTGT
4551 TCAACAGGCC AGCCATTACG CTCGTCATCA AAATCACTCG CATCAACCAA
4601 ACCGTTATTC ATTCGTGATT GCGCCTGAGC GAGACGAAAT ACGCGATCGC
4651 TGTTAAAAGG ACAATTACAA ACAGGAATCG AATGCAACCG GCGCAGGAAC
4701 ACTGCCAGCG CATCAACAAT ATTTTCACCT GAATCAGGAT ATTCTTCTAA
4751 TACCTGGAAT GCTGTTTTCC CGGGGATCGC AGTGGTGAGT AACCATGCAT
4801 CATCAGGAGT ACGGATAAAA TGCTTGATGG TCGGAAGAGG CATAAATTCC
4851 GTCAGCCAGT TTAGTCTGAC CATCTCATCT GTAACATCAT TGGCAACGCT
4901 ACCTTTGCCA TGTTTCAGAA ACAACTCTGG CGCATCGGGC TTCCCATACA
4951 ATCGATAGAT TGTCGCACCT GATTGCCCGA CATTATCGCG AGCCCATTTA
5001 TACCCATATA AATCAGCATC CATGTTGGAA TTTAATCGCG GCCTAGAGCA
5051 AGACGTTTCC CGTTGAATAT GGCTCATAAC ACCCCTTGTA TTACTGTTTA
5101 TGTAAGCAGA CAGTTTTATT GTTCATGATG ATATATTTTT ATCTTGTGCA
5151 ATGTAACATC AGAGATTTTG AGACACAACG TGGCTTTCCC CCCCCCCCA
5201 TTATTGAAGC ATTTATCAGG GTTATTGTCT CATGAGCGGA TACATATTTG
5251 AATGTATTTA GAAAATAAA CAAATAGGGG TTCCGCGCAC ATTTCCCCGA
5301 AAAGTGCCAC CTGACGTCTA AGAAACCATT ATTATCATGA CATTAACCTA
5351 TAAAAATAGG CGTATCACGA GGCCCTTTCG TCTCGCGCGT TTCGGTGATG
5401 ACGGTGAAAA CCTCTGACAC ATGCAGCTCC CGGAGACGGT CACAGCTTGT
5451 CTGTAAGCGG ATGCCGGGAG CAGACAAGCC CGTCAGGGCG CGTCAGCGGG
5501 TGTTGGCGGG TGTCGGGGCT GGCTTAACTA TGCGGCATCA GAGCAGATTG
5551 TACTGAGAGT GCACCATATG CGGTGTGAAA TACCGCACAG ATGCGTAAGG
5601 AGAAAATACC GCATCAGATT GGCTAT
```

FIG 21B    FIG 21    FIG 21A
                     FIG 21B

```
   1 TGGCCATTGC ATACGTTGTA TCCATATCAT AATATGTACA TTTATATTGG
  51 CTCATGTCCA ACATTACCGC CATGTTGACA TTGATTATTG ACTAGTTATT
 101 AATAGTAATC AATTACGGGG TCATTAGTTC ATAGCCCATA TATGGAGTTC
 151 CGCGTTACAT AACTTACGGT AAATGGCCCG CCTGGCTGAC CGCCCAACGA
 201 CCCCCGCCCA TTGACGTCAA TAATGACGTA TGTTCCCATA GTAACGCCAA
 251 TAGGGACTTT CCATTGACGT CAATGGGTGG AGTATTTACG GTAAACTGCC
 301 CACTTGGCAG TACATCAAGT GTATCATATG CCAAGTACGC CCCTATTGA
 351 CGTCAATGAC GGTAAATGGC CCGCCTGGCA TTATGCCCAG TACATGACCT
 401 TATGGGACTT TCCTACTTGG CAGTACATCT ACGTATTAGT CATCGCTATT
 451 ACCATGGTGA TGCGGTTTTG GCAGTACATC AATGGGCGTG GATAGCGGTT
 501 TGACTCACGG GGATTTCCAA GTCTCCACCC CATTGACGTC AATGGGAGTT
 551 TGTTTTGGCA CCAAAATCAA CGGGACTTTC CAAAATGTCG TAACAACTCC
 601 GCCCCATTGA CGCAAATGGG CGGTAGGCGT GTACGGTGGG AGGTCTATAT
 651 AAGCAGAGCT CGTTTAGTGA ACCGTCAGAT CGCCTGGAGA CGCCATCCAC
 701 GCTGTTTTGA CCTCCATAGA AGACACCGGG ACCGATCCAG CCTCCGCGGC
 751 CGGGAACGGT GCATTGGAAC GCGGATTCCC CGTGCCAAGA GTGACGTAAG
 801 TACCGCCTAT AGAGTCTATA GGCCCACCCC CTTGGCTTCT TATGCATGCT
 851 ATACTGTTTT TGGCTTGGGG TCTATACACC CCGCTTCCT CATGTTATAG
 901 GTGATGGTAT AGCTTAGCCT ATAGGTGTGG GTTATTGACC ATTATTGACC
 951 ACTCCCCTAT TGGTGACGAT ACTTCCATT ACTAATCCAT AACATGGCTC
1001 TTTGCCACAA CTCTCTTTAT TGGCTATATG CCAATACACT GTCCTTCAGA
1051 GACTGACACG GACTCTGTAT TTTTACAGGA TGGGGTCTCA TTTATTATTT
1101 ACAAATTCAC ATATACAACA CCACCGTCCC CAGTGCCCGC AGTTTTTATT
1151 AAACATAACG TGGGATCTCC ACGCGAATCT CGGGTACGTG TTCCGGACAT
1201 GGGCTCTTCT CCGGTAGCGG CGGAGCTTCT ACATCCGAGC CCTGCTCCCA
1251 TGCCTCCAGC GACTCATGGT CGCTCGGCAG CTCCTTGCTC CTAACAGTGG
1301 AGGCCAGACT TAGGCACAGC ACGATGCCCA CCACCACCAG TGTGCCGCAC
1351 AAGGCCGTGG CGGTAGGGTA TGTGTCTGAA AATGAGCTCG GGGAGCGGGC
1401 TTGCACCGCT GACGCATTTG AAGACTTAA GGCAGCGGCA GAAGAAGATG
1451 CAGGCAGCTG AGTTGTTGTG TTCTGATAAG AGTCAGAGGT AACTCCCGTT
1501 GCGGTGCTGT TAACGGTGGA GGGCAGTGTA GTCTGAGCAG TACTCGTTGC
1551 TGCCGCGCGC GCCACCAGAC ATAATAGCTG ACAGACTAAC AGACTGTTCC
1601 TTTCCATGGG TCTTTTCTGC AGTCACCGTC GTCGACCAGA GCTGAGATCC
1651 TACAGGAGTC CAGGGCTGGA GAGAAAACCT CTGCGAGGAA AGGGAAGGAG
1701 CAAGCCGTGA ATTTAAGGGA CGCTGTGAAG CAATCATGGA TGCAATGAAG
1751 AGAGGGCTCT GCTGTGTGCT GCTGCTGTGT GGAGCAGTCT TCGTTTCGCC
1801 CAGCGGTACC TGTAATAATT CAGGGAAAGG TGGGGATTCT GCATCTACTA
1851 ATCCTGCTGA CGAGTCTGCG AAAGGGCCTA ATCTTACAGA AATAAGCAAA
1901 AAAATTACAG ATTCTAATGC ATTTGTACTT GCTGTTAAAG AAGTTGAGAC
1951 TTTGGTTTTA TCTATAGATG AACTTGCTAA GAAAGCTATA GGTCAAAAAA
2001 TAGACAATAA TAATGGTTTA GCTGCTTTAA ATAATCAGAA TGGATCGTTG
2051 TTAGCAGGAG CCTATGCAAT ATCAACCCTA ATAACAGAAA AATTGAGTAA
2101 ATTGAAAAAT TTAGAAGAAT TAAAGACAGA AATTGCAAAG CTAAGAAAT
2151 GTTCCGAAGA ATTTACTAAT AAACTAAAAA GTGGTCATGC AGATCTTGGC
2201 AAACAGGATG CTACCGATGA TCATGCAAAA GCAGCTATTT TAAAAACACA
2251 TGCAACTACC GATAAGGTG CTAAAGAATT TAAAGATTTA TTTGAATCAG
2301 TAGAAGGTTT GTTAAAAGCA GCTCAAGTAG CACTAACTAA TTCAGTTAAA
2351 GAACTTACAA GTCCTGTTGT AGCAGAAAGT CCAAAAAAAC CTTAAGGATC
2401 CAGATCTGCT GTGCCTTCTA GTTGCCAGCC ATCTGTTGTT TGCCCCTCCC
2451 CCGTGCCTTC CTTGACCCTG GAAGGTGCCA CTCCCACTGT CCTTTCCTAA
2501 TAAAATGAGG AAATTGCATC GCATTGTCTG AGTAGGTGTC ATTCTATTCT
2551 GGGGGGTGGG GTGGGGCAGC ACAGCAAGGG GGAGGATTGG GAAGACAATA
2601 GCAGGCATGC TGGGGATGCG GTGGGCTCTA TGGGACCCA GGTGCTGAAG
2651 AATTGACCCG GTTCCTCCTG GGCCAGAAAG AAGCAGGCAC ATCCCCTTCT
2701 CTGTGACACA CCCTGTCCAC GCCCCTGGTT CTTAGTTCCA GCCCCACTCA
```

```
2751 TAGGACACTC ATAGCTCAGG AGGGCTCCGC CTTCAATCCC ACCCGCTAAA
2801 GTACTTGGAG CGGTCTCTCC CTCCCTCATC AGCCCACCAA ACCAAACCTA
2851 GCCTCCAAGA GTGGGAAGAA ATTAAAGCAA GATAGGCTAT TAAGTGCAGA
2901 GGGAGAGAAA ATGCCTCCAA CATGTGAGGA AGTAATGAGA GAAATCATAG
2951 AATTTCTTCC GCTTCCTCGC TCACTGACTC GCTGCGCTCG GTCGTTCGGC
3001 TGCGGCGAGC GGTATCAGCT CACTCAAAGG CGGTAATACG GTTATCCACA
3051 GAATCAGGGG ATAACGCAGG AAAGAACATG TGAGCAAAAG GCCAGCAAAA
3101 GGCCAGGAAC CGTAAAAAGG CCGCGTTGCT GGCGTTTTTC CATAGGCTCC
3151 GCCCCCCTGA CGAGCATCAC AAAAATCGAC GCTCAAGTCA GAGGTGGCGA
3201 AACCCGACAG GACTATAAAG ATACCAGGCG TTTCCCCCTG GAAGCTCCCT
3251 CGTGCGCTCT CCTGTTCCGA CCCTGCCGCT TACCGGATAC CTGTCCGCCT
3301 TTCTCCCTTC GGGAAGCGTG GCGCTTTCTC AATGCTCACG CTGTAGGTAT
3351 CTCAGTTCGG TGTAGGTCGT TCGCTCCAAG CTGGGCTGTG TGCACGAACC
3401 CCCCGTTCAG CCCGACCGCT GCGCCTTATC CGGTAACTAT CGTCTTGAGT
3451 CCAACCCGGT AAGACACGAC TTATCGCCAC TGGCAGCAGC CACTGGTAAC
3501 AGGATTAGCA GAGCGAGGTA TGTAGGCGGT GCTACAGAGT TCTTGAAGTG
3551 GTGGCCTAAC TACGGCTACA CTAGAAGGAC AGTATTTGGT ATCTGCGCTC
3601 TGCTGAAGCC AGTTACCTTC GGAAAAAGAG TTGGTAGCTC TTGATCCGGC
3651 AAACAAACCA CCGCTGGTAG CGGTGGTTTT TTTGTTTGCA AGCAGCAGAT
3701 TACGCGCAGA AAAAAAGGAT CTCAAGAAGA TCCTTTGATC TTTTCTACGG
3751 GGTCTGACGC TCAGTGGAAC GAAAACTCAC GTTAAGGGAT TTTGGTCATG
3801 AGATTATCAA AAAGGATCTT CACCTAGATC CTTTTAAATT AAAAATGAAG
3851 TTTTAAATCA ATCTAAAGTA TATATGAGTA AACTTGGTCT GACAGTTACC
3901 AATGCTTAAT CAGTGAGGCA CCTATCTCAG CGATCTGTCT ATTTCGTTCA
3951 TCCATAGTTG CCTGACTCCG GGGGGGGGG GCGCTGAGGT CTGCCTCGTG
4001 AAGAAGGTGT TGCTGACTCA TACCAGGCCT GAATCGCCCC ATCATCCAGC
4051 CAGAAAGTGA GGGAGCCACG GTTGATGAGA GCTTTGTTGT AGGTGGACCA
4101 GTTGGTGATT TTGAACTTTT GCTTTGCCAC GGAACGGTCT GCGTTGTCGG
4151 GAAGATGCGT GATCTGATCC TTCAACTCAG CAAAAGTTCG ATTTATTCAA
4201 CAAAGCCGCC GTCCCGTCAA GTCAGCGTAA TGCTCTGCCA GTGTTACAAC
4251 CAATTAACCA ATTCTGATTA GAAAACTCA TCGAGCATCA AATGAAACTG
4301 CAATTTATTC ATATCAGGAT TATCAATACC ATATTTTTGA AAAAGCCGTT
4351 TCTGTAATGA AGGAGAAAAC TCACCGAGGC AGTTCCATAG GATGGCAAGA
4401 TCCTGGTATC GGTCTGCGAT TCCGACTCGT CCAACATCAA TACAACCTAT
4451 TAATTTCCCC TCGTCAAAAA TAAGGTTATC AAGTGAGAAA TCACCATGAG
4501 TGACGACTGA ATCCGGTGAG AATGGCAAAA GCTTATGCAT TTCTTTCCAG
4551 ACTTGTTCAA CAGGCCAGCC ATTACGCTCG TCATCAAAAT CACTCGCATC
4601 AACCAAACCG TTATTCATTC GTGATTGCGC CTGAGCGAGA CGAAATACGC
4651 GATCGCTGTT AAAAGGACAA TTACAAACAG GAATCGAATG CAACCGGCGC
4701 AGGAACACTG CCAGCGCATC AACAATATTT TCACCTGAAT CAGGATATTC
4751 TTCTAATACC TGGAATGCTG TTTTCCCGGG GATCGCAGTG GTGAGTAACC
4801 ATGCATCATC AGGAGTACGG ATAAAATGCT TGATGGTCGG AAGAGGCATA
4851 AATTCCGTCA GCCAGTTTAG TCTGACCATC TCATCTGTAA CATCATTGGC
4901 AACGCTACCT TTGCCATGTT TCAGAAACAA CTCTGGCGCA TCGGGCTTCC
4951 CATACAATCG ATAGATTGTC GCACCTGATT GCCCGACATT ATCGCGAGCC
5001 CATTTATACC CATATAAATC AGCATCCATG TTGGAATTTA ATCGCGGCCT
5051 AGAGCAAGAC GTTTCCCGTT GAATATGGCT CATAACACCC CTTGTATTAC
5101 TGTTTATGTA AGCAGACAGT TTTATTGTTC ATGATGATAT ATTTTTATCT
5151 TGTGCAATGT AACATCAGAG ATTTTGAGAC ACAACGTGGC TTTCCCCCCC
5201 CCCCCATTAT TGAAGCATTT ATCAGGGTTA TTGTCTCATG AGCGGATACA
5251 TATTTGAATG TATTTAGAAA AATAAACAAA TAGGGGTTCC GCGCACATTT
5301 CCCCGAAAAG TGCCACCTGA CGTCTAAGAA ACCATTATTA TCATGACATT
5351 AACCTATAAA AATAGGCGTA TCACGAGGCC CTTTCGTCTC GCGCGTTTCG
5401 GTGATGACGG TGAAAACCTC TGACACATGC AGCTCCCGGA GACGGTCACA
5451 GCTTGTCTGT AAGCGGATGC CGGGAGCAGA CAAGCCCGTC AGGGCGCGTC
5501 AGCGGGTGTT GGCGGGTGTC GGGGCTGGCT TAACTATGCG GCATCAGAGC
5551 AGATTGTACT GAGAGTGCAC CATATGCGGT GTGAAATACC GCACAGATGC
5601 GTAAGGAGAA AATACCGCAT CAGATTGGCT AT
```

```
   1 TCGCGCGTTT CGGTGATGAC GGTGAAAACC TCTGACACAT GCAGCTCCCG
  51 GAGACGGTCA CAGCTTGTCT GTAAGCGGAT GCCGGGAGCA GACAAGCCCG
 101 TCAGGGCGCG TCAGCGGGTG TTGGCGGGTG TCGGGGCTGG CTTAACTATG
 151 CGGCATCAGA GCAGATTGTA CTGAGAGTGC ACCATATGCG GTGTGAAATA
 201 CCGCACAGAT GCGTAAGGAG AAAATACCGC ATCAGATTGG CTATTGGCCA
 251 TTGCATACGT TGTATCCATA TCATAATATG TACATTTATA TTGGCTCATG
 301 TCCAACATTA CCGCCATGTT GACATTGATT ATTGACTAGT TATTAATAGT
 351 AATCAATTAC GGGGTCATTA GTTCATAGCC CATATATGGA GTTCCGCGTT
 401 ACATAACTTA CGGTAAATGG CCCGCCTGGC TGACCGCCCA ACGACCCCCG
 451 CCCATTGACG TCAATAATGA CGTATGTTCC CATAGTAACG CCAATAGGGA
 501 CTTTCCATTG ACGTCAATGG GTGGAGTATT TACGGTAAAC TGCCCACTTG
 551 GCAGTACATC AAGTGTATCA TATGCCAAGT ACGCCCCCTA TTGACGTCAA
 601 TGACGGTAAA TGGCCCGCCT GGCATTATGC CCAGTACATG ACCTTATGGG
 651 ACTTTCCTAC TTGGCAGTAC ATCTACGTAT TAGTCATCGC TATTACCATG
 701 GTGATGCGGT TTTGGCAGTA CATCAATGGG CGTGGATAGC GGTTTGACTC
 751 ACGGGGATTT CCAAGTCTCC ACCCCATTGA CGTCAATGGG AGTTTGTTTT
 801 GGCACCAAAA TCAACGGGAC TTTCCAAAAT GTCGTAACAA CTCCGCCCCA
 851 TTGACGCAAA TGGGCGGTAG GCGTGTACGG TGGGAGGTCT ATATAAGCAG
 901 AGCTCGTTTA GTGAACCGTC AGATCGCCTG GAGACGCCAT CCACGCTGTT
 951 TTGACCTCCA TAGAAGACAC CGGGACCGAT CCAGCCTCCG CGGCCGGGAA
1001 CGGTGCATTG GAACGCGGAT TCCCCGTGCC AAGAGTGACG TAAGTACCGC
1051 CTATAGACTC TATAGGCACA CCCCTTTGGC TCTTATGCAT GCTATACTGT
1101 TTTTGGCTTG GGGCCTATAC ACCCCGCTT CCTTATGCTA TAGGTGATGG
1151 TATAGCTTAG CCTATAGGTG TGGGTTATTG ACCATTATTG ACCACTCCCC
1201 TATTGGTGAC GATACTTTCC ATTACTAATC CATAACATGG CTCTTTGCCA
1251 CAACTATCTC TATTGGCTAT ATGCCAATAC TCTGTCCTTC AGAGACTGAC
1301 ACGGACTCTG TATTTTACA GGATGGGGTC CCATTTATTA TTTACAAATT
1351 CACATATACA ACAACGCCGT CCCCCGTGCC CGCAGTTTTT ATTAAACATA
1401 GCGTGGGATC TCCACGCGAA TCTCGGGTAC GTGTTCCGGA CATGGGCTCT
1451 TCTCCGGTAG CGGCGGAGCT TCCACATCCG AGCCCTGGTC CCATGCCTCC
1501 AGCGGCTCAT GGTCGCTCGG CAGCTCCTTG CTCCTAACAG TGGAGGCCAG
1551 ACTTAGGCAC AGCACAATGC CCACCACCAC CAGTGTGCCG CACAAGGCCG
1601 TGGCGGTAGG GTATGTGTCT GAAAATGAGC GTGGAGATTG GGCTCGCACG
1651 GCTGACGCAG ATGGAAGACT TAAGGCAGCG GCAGAAGAAG ATGCAGGCAG
1701 CTGAGTTGTT GTATTCTGAT AAGAGTCAGA GGTAACTCCC GTTGCGGTGC
1751 TGTTAACGGT GGAGGGCAGT GTAGTCTGAG CAGTACTCGT TGCTGCCGCG
1801 CGCGCCACCA GACATAATAG CTGACAGACT AACAGACTGT TCCTTTCCAT
1851 GGGTCTTTTC TGCAGTCACC GTCGTCGACC AGAGCTGAGA TCCTACAGGA
1901 GTCCAGGGCT GGAGAGAAAA CCTCTGCGAG GAAAGGGAAG GAGCAAGCCG
1951 TGAATTTAAG GGACGCTGTG AAGCAATCAT GGATGCAATG AAGAGAGGGC
2001 TCTGCTGTGT GCTGCTGCTG TGTGGAGCAG TCTTCGTTTC GCCCAGCGGT
2051 ACCGGATCCA GATCTGCTGT GCCTTCTAGT TGCCAGCCAT CTGTTGTTTG
2101 CCCCTCCCCC GTGCCTTCCT TGACCCTGGA AGGTGCCACT CCCACTGTCC
2151 TTTCCTAATA AAATGAGGAA ATTGCATCGC ATTGTCTGAG TAGGTGTCAT
2201 TCTATTCTGG GGGTGGGGT GGGGCAGCAC AGCAAGGGGG AGGATTGGGA
2251 AGACAATAGC AGGCATGCTG GGGATGCGGT GGGCTCTATG GGACCCAGG
2301 TGCTGAAGAA TTGACCCGGT TCCTCCTGGG CCAGAAAGAA GCAGGCACAT
2351 CCCCTTCTCT GTGACACACC CTGTCCACGC CCTGGTTCTA GTTCCAGC
2401 CCCACTCATA GGACACTCAT AGCTCAGGAG GCTCCGCCT TCAATCCCAC
2451 CCGCTAAAGT ACTTGGAGCG GTCTCTCCCT CCCTCATCAG CCCACCAAAC
2501 CAAACCTAGC CTCCAAGAGT GGGAAGAAAT TAAAGCAAGA TAGGCTATTA
2551 AGTGCAGAGG GAGAGAAAAT GCCTCCAACA TGTGAGGAAG TAATGAGAGA
2601 AATCATAGAA TTTCTTCCGC TTCCTCGCTC ACTGACTCGC TGCGCTCGGT
2651 CGTTCGGCTG CGGCGAGCGG TATCAGCTCA CTCAAAGGCG GTAATACGGT
2701 TATCCACAGA ATCAGGGGAT AACGCAGGAA AGAACATGTG AGCAAAAGGC
```

```
2751 CAGCAAAAGG CCAGGAACCG TAAAAAGGCC GCGTTGCTGG CGTTTTTCCA
2801 TAGGCTCCGC CCCCCTGACG AGCATCACAA AAATCGACGC TCAAGTCAGA
2851 GGTGGCGAAA CCCGACAGGA CTATAAAGAT ACCAGGCGTT TCCCCCTGGA
2901 AGCTCCCTCG TGCGCTCTCC TGTTCCGACC CTGCCGCTTA CCGGATACCT
2951 GTCCGCCTTT CTCCCTTCGG GAAGCGTGGC GCTTTCTCAA TGCTCACGCT
3001 GTAGGTATCT CAGTTCGGTG TAGGTCGTTC GCTCCAAGCT GGGCTGTGTG
3051 CACGAACCCC CCGTTCAGCC CGACCGCTGC GCCTTATCCG GTAACTATCG
3101 TCTTGAGTCC AACCCGGTAA GACACGACTT ATCGCCACTG GCAGCAGCCA
3151 CTGGTAACAG GATTAGCAGA GCGAGGTATG TAGGCGGTGC TACAGAGTTC
3201 TTGAAGTGGT GGCCTAACTA CGGCTACACT AGAAGGACAG TATTTGGTAT
3251 CTGCGCTCTG CTGAAGCCAG TTACCTTCGG AAAAAGAGTT GGTAGCTCTT
3301 GATCCGGCAA ACAAACCACC GCTGGTAGCG GTGGTTTTTT TGTTTGCAAG
3351 CAGCAGATTA CGCGCAGAAA AAAAGGATCT CAAGAAGATC CTTTGATCTT
3401 TTCTACGGGG TCTGACGCTC AGTGGAACGA AAACTCACGT TAAGGGATTT
3451 TGGTCATGAG ATTATCAAAA AGGATCTTCA CCTAGATCCT TTTAAATTAA
3501 AAATGAAGTT TTAAATCAAT CTAAAGTATA TATGAGTAAA CTTGGTCTGA
3551 CAGTTACCAA TGCTTAATCA GTGAGGCACC TATCTCAGCG ATCTGTCTAT
3601 TTCGTTCATC CATAGTTGCC TGACTCCGGG GGGGGGGGGC GCTGAGGTCT
3651 GCCTCGTGAA GAAGGTGTTG CTGACTCATA CCAGGCCTGA ATCGCCCCAT
3701 CATCCAGCCA GAAAGTGAGG GAGCCACGGT TGATGAGAGC TTTGTTGTAG
3751 GTGGACCAGT TGGTGATTTT GAACTTTTGC TTTGCCACGG AACGGTCTGC
3801 GTTGTCGGGA AGATGCGTGA TCTGATCCTT CAACTCAGCA AAAGTTCGAT
3851 TTATTCAACA AAGCCGCCGT CCCGTCAAGT CAGCGTAATG CTCTGCCAGT
3901 GTTACAACCA ATTAACCAAT TCTGATTAGA AAAACTCATC GAGCATCAAA
3951 TGAAACTGCA ATTTATTCAT ATCAGGATTA TCAATACCAT ATTTTTGAAA
4001 AAGCCGTTTC TGTAATGAAG GAGAAAACTC ACCGAGGCAG TTCCATAGGA
4051 TGGCAAGATC CTGGTATCGG TCTGCGATTC CGACTCGTCC AACATCAATA
4101 CAACCTATTA ATTTCCCCTC GTCAAAAATA AGGTTATCAA GTGAGAAATC
4151 ACCATGAGTG ACGACTGAAT CCGGTGAGAA TGGCAAAAGC TTATGCATTT
4201 CTTTCCAGAC TTGTTCAACA GGCCAGCCAT TACGCTCGTC ATCAAAATCA
4251 CTCGCATCAA CCAAACCGTT ATTCATTCGT GATTGCGCCT GAGCGAGACG
4301 AAATACGCGA TCGCTGTTAA AAGGACAATT ACAAACAGGA ATCGAATGCA
4351 ACCGGCGCAG GAACACTGCC AGCGCATCAA CAATATTTTC ACCTGAATCA
4401 GGATATTCTT CTAATACCTG GAATGCTGTT TTCCCGGGGA TCGCAGTGGT
4451 GAGTAACCAT GCATCATCAG GAGTACGGAT AAAATGCTTG ATGGTCGGAA
4501 GAGGCATAAA TTCCGTCAGC CAGTTTAGTC TGACCATCTC ATCTGTAACA
4551 TCATTGGCAA CGCTACCTTT GCCATGTTTC AGAAACAACT CTGGCGCATC
4601 GGGCTTCCCA TACAATCGAT AGATTGTCGC ACCTGATTGC CCGACATTAT
4651 CGCGAGCCCA TTTATACCCA TATAAATCAG CATCCATGTT GGAATTTAAT
4701 CGCGGCCTAG AGCAAGACGT TTCCCGTTGA ATATGGCTCA TAACACCCCT
4751 TGTATTACTG TTTATGTAAG CAGACAGTTT TATTGTTCAT GATGATATAT
4801 TTTTATCTTG TGCAATGTAA CATCAGAGAT TTTGAGACAC AACGTGGCTT
4851 TCCCCCCCCC CCCATTATTG AAGCATTTAT CAGGGTTATT GTCTCATGAG
4901 CGGATACATA TTTGAATGTA TTTAGAAAAA TAAACAAATA GGGGTTCCGC
4951 GCACATTTCC CCGAAAAGTG CCACCTGACG TCTAAGAAAC CATTATTATC
5001 ATGACATTAA CCTATAAAAA TAGGCGTATC ACGAGGCCCT TTCGTC
```

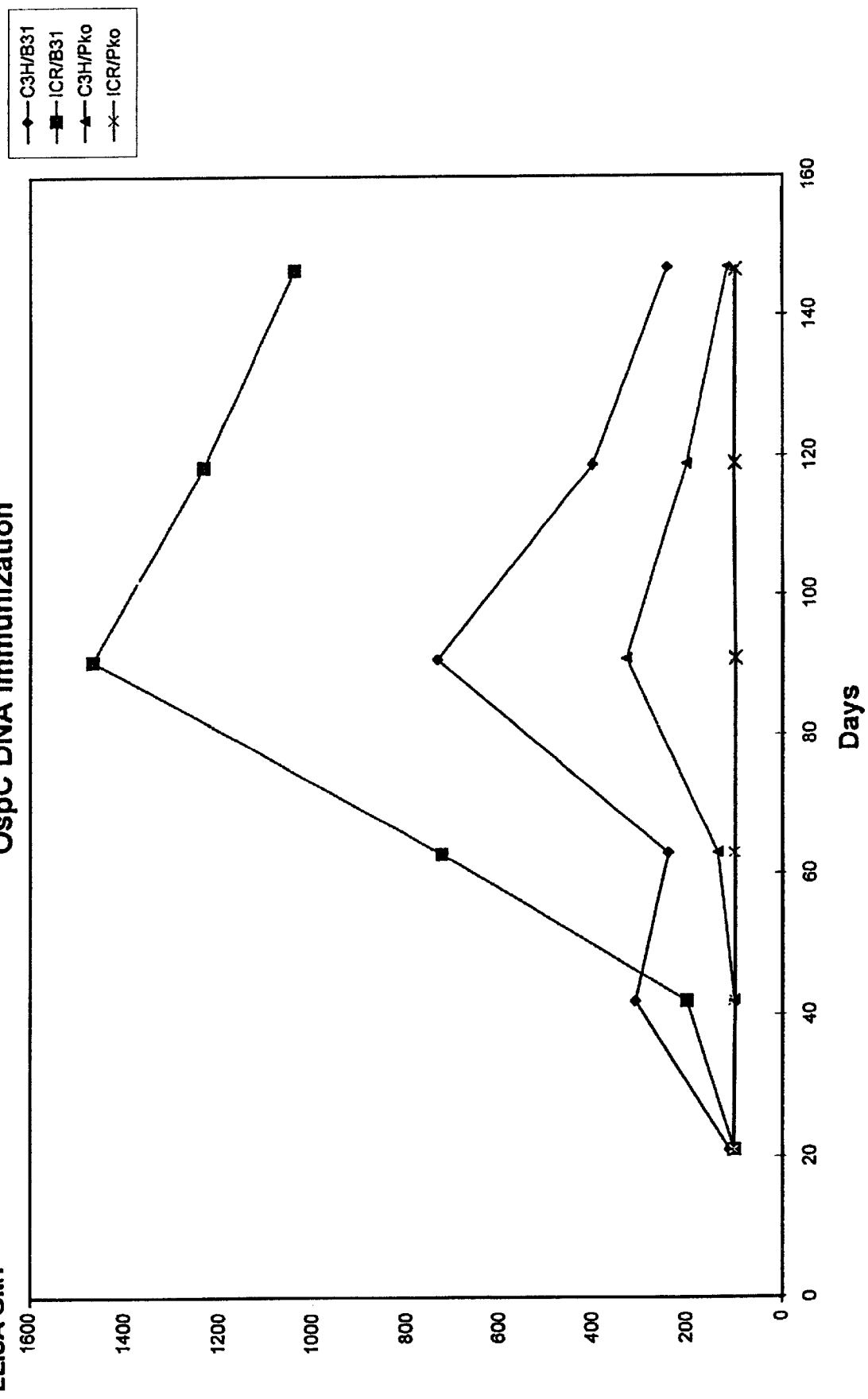
FIG. 27 OspC DNA Immunization

SEQUENCE LISTING

<160> NUMBER OF SEQ ID NOS: 18

<210> SEQ ID NO 1
<211> LENGTH: 5845
<212> TYPE: DNA
<213> ORGANISM: Borrelia burgdorferi

<400> SEQUENCE: 1

```
gtcaccgtcg tcgaccagag ctgagatcct acaggagtcc agggctggag agaaaacctc      60
tgcgaggaaa gggaaggagc aagccgtgaa tttaagggac gctgtgaagc aatcatggat     120
gcaatgaaga gagggctctg ctgtgtgctg ctgctgtgtg gagcagtctt cgtttcgccc     180
agcggtacct gtaagcaaaa tgttagcagc cttgacgaga aaacagcgt ttcagtagat      240 ttgcctggtg aaatgaaagt tcttgtaagc aaagaaaaaa acaaagacgg caagtacgat     300
ctaattgcaa cagtagacaa gcttgagctt aaaggaactt ctgataaaaa caatggatct     360
ggagtacttg aaggcgtaaa agctgacaaa agtaaagtaa aattaacaat ttctgacgat     420
ctaggtcaaa ccacacttga agttttcaaa gaagatggca aaacactagt atcaaaaaaa     480
gtaacttcca aagacaagtc atcaacagaa gaaaattca atgaaaaagg tgaagtatct     540
gaaaaaataa taacaagagc agacggaacc agacttgaat acacagaaat taaaagcgat     600
ggatctggaa aagctaaaga ggttttaaaa ggctatgttc ttgaaggaac tctaactgct     660
gaaaaaacaa cattggtggt taagaagga actgttactt aagcaaaaa tatttcaaaa     720 tctggggaag tttcagttga acttaatgac actgacagta gtgctgctac taaaaaaact     780
gcagcttgga attcaggcac ttcaactta acaattactg taaacagtaa aaaaactaaa     840
gaccttgtgt ttacaaaaga aaacacaatt acagtacaac aatacgactc aaatggcacc     900
```

-continued

```
aaattagagg ggtcagcagt tgaaattaca aaacttgatg aaattaaaaa cgctcttaag      960
taaggagaat tttctagacc aggcgcctgg atccagatct gctgtgcctt ctagttgcca     1020
gccatctgtt gtttgcccct cccccgtgcc ttccttgacc ctggaaggtg ccactcccac     1080
tgtcctttcc taataaaatg aggaaattgc atcgcattgt ctgagtaggt gtcattctat     1140
tctgggggt ggggtggggc agcacagcaa ggggaggat tgggaagaca atagcaggca       1200
tgctggggat gcggtgggct ctatgggtac ccaggtgctg aagaattgac ccggttcctc     1260
ctgggccaga agaagcagg cacatcccct tctctgtgac acaccctgtc cacgcccctg      1320
gttcttagtt ccagccccac tcataggaca ctcatagctc aggagggctc cgccttcaat    1380
cccacccgct aaagtacttg gagcggtctc tccctccctc atcagcccac caaaccaaac    1440
ctagcctcca agagtgggaa gaaattaaag caagataggc tattaagtgc agagggagag    1500
aaaatgcctc caacatgtga ggaagtaatg agagaaatca tagaatttct tccgcttcct    1560
cgctcactga ctcgctgcgc tcggtcgttc ggctgcggcg agcggtatca gctcactcaa    1620
aggcggtaat acgttatcc acagaatcag ggataacgc aggaaagaac atgtgagcaa     1680
aaggccagca aaaggccagg aaccgtaaaa aggccgcgtt gctggcgttt ttccataggc    1740
tccgcccccc tgacgagcat cacaaaaatc gacgctcaag tcagaggtgg cgaaacccga    1800
caggactata aagataccag gcgtttcccc ctggaagctc cctcgtgcgc tctcctgttc    1860
cgaccctgcc gcttaccgga tacctgtccg ccttcctccc ttcgggaagc gtggcgcttt    1920
ctcaatgctc acgctgtagg tatctcagtt cggtgtaggt cgttcgctcc aagctgggct    1980
gtgtgcacga accccccgtt cagcccgacc gctgcgcctt atccggtaac tatcgtcttg    2040
agtccaaccc ggtaagacac gacttatcgc cactggcagc agccactggt aacaggatta    2100
gcagagcgag gtatgtaggc ggtgctacag agttcttgaa gtggtggcct aactacggct    2160
acactagaag gacagtattt ggtatctgcg ctctgctgaa gccagttacc ttcggaaaaa    2220
gagttggtag ctcttgatcc ggcaaacaaa ccaccgctgg tagcggtggt ttttttgttt    2280
gcaagcagca gattacgcgc agaaaaaaag gatctcaaga agatcctttg atcttttcta    2340
cggggtctga cgctcagtgg aacgaaaact cacgttaagg gattttggtc atgagattat    2400
caaaaggat cttcacctag atccttttaa attaaaaatg aagttttaaa tcaatctaaa      2460
gtatatatga gtaaacttgg tctgacagtt accaatgctt aatcagtgag gcacctatct    2520
cagcgatctg tctatttcgt tcatccatag ttgcctgact ccggggggg gggcgctga     2580
ggtctgcctc gtgaagaagg tgttgctgac tcataccagg cctgaatcgc cccatcatcc    2640
agccagaaag tgagggagcc acggttgatg agagctttgt tgtaggtgga ccagttggtg    2700
atttgaactt ttgctttgcc acggaacggt ctgcgttgtc gggaagatgc gtgatctgat    2760
ccttcaactc agcaaaagtt cgatttattc aacaaagccg ccgtcccgtc aagtcagcgt    2820
aatgctctgc cagtgttaca accaattaac caattctgat tagaaaaact catcgagcat    2880
caaatgaaac tgcaatttat tcatatcagg attatcaata ccatattttt gaaaaagccg    2940
tttctgtaat gaaggagaaa actcaccgag gcagttccat aggatggcaa gatcctggta    3000
tcggtctgcg attccgactc gtccaacatc aatacaacct attaatttcc cctcgtcaaa    3060
aataaggtta tcaagtgaga atcaccatg agtgacgact gaatccggtg agaatggcaa    3120
aagcttatgc atttctttcc agacttgttc aacaggccag ccattacgct cgtcatcaaa    3180
atcactcgca tcaaccaaac cgttattcat tcgtgattgc gcctgagcga cgcgaaatac    3240
gcgatcgctg ttaaaaggac aattacaaac aggaatcgaa tgcaaccggc gcaggaacac    3300
```

```
tgccagcgca tcaacaatat tttcacctga atcaggatat tcttctaata cctggaatgc   3360
tgttttcccg gggatcgcag tggtgagtaa ccatgcatca tcaggagtac ggataaaatg   3420
cttgatggtc ggaagaggca taaattccgt cagccagttt agtctgacca tctcatctgt   3480
aacatcattg gcaacgctac ctttgccatg tttcagaaac aactctggcg catcgggctt   3540
cccatacaat cgatagattg tcgcacctga ttgcccgaca ttatcgcgag cccatttata   3600
cccatataaa tcagcatcca tgttggaatt taatcgcggc ctcgagcaag acgtttcccg   3660
ttgaatatgg ctcataacac cccttgtatt actgtttatg taagcagaca gttttattgt   3720
tcatgatgat atatttttat cttgtgcaat gtaacatcag agattttgag acacaacgtg   3780
gctttccccc cccccccatt attgaagcat ttatcagggt tattgtctca tgagcggata   3840
catatttgaa tgtatttaga aaataaaca aatagggggtt ccgcgcacat ttccccgaaa   3900
agtgccacct gacgtctaag aaaccattat tatcatgaca ttaacctata aaataggcg    3960 tatcacgagg ccctttcgtc tcgcgcgttt cggtgatgac ggtgaaaacc tctgacacat   4020
gcagctcccg gagacggtca cagcttgtct gtaagcggat gccggagca gacaagcccg    4080 tcagggcgcg tcagcgggtg ttggcgggtg tcggggctgg cttaactatg cggcatcaga   4140
gcagattgta ctgagagtgc accatatgcg gtgtgaaata ccgcacagat gcgtaaggag   4200
aaaataccgc atcagattgg ctattggcca ttgcatacgt tgtatccata tcataatatg   4260
tacatttata ttggctcatg tccaacatta ccgccatgtt gacattgatt attgactagt   4320
tattaatagt aatcaattac ggggtcatta gttcatagcc catatatgga gttccgcgtt   4380
acataactta cggtaaatgg cccgcctggc tgaccgccca acgacccccg cccattgacg   4440
tcaataatga cgtatgttcc catagtaacg ccaatagga ctttccattg acgtcaatgg    4500
gtggagtatt tacggtaaac tgcccacttg gcagtacatc aagtgtatca tatgccaagt   4560 acgccccta ttgacgtcaa tgacggtaaa tggcccgcct ggcattatgc ccagtacatg    4620
accttatggg actttcctac ttggcagtac atctacgtat tagtcatcgc tattaccatg   4680
gtgatgcggt tttggcagta catcaatggg cgtggatagc ggtttgactc acgggatttc   4740
ccaagtctcc accccattga cgtcaatggg agtttgtttt ggcaccaaaa tcaacgggac   4800
tttccaaaat gtcgtaacaa ctccgcccca ttgacgcaaa tgggcggtag gcgtgtacgg   4860
tgggaggtct atataagcag agctcgttta gtgaaccgtc agatcgcctg gagacgccat   4920
ccacgctgtt ttgacctcca tagaagacac cgggaccgat ccagcctccg cggccgggaa   4980
cggtgcattg gaacgcggat tccccgtgcc aagagtgacg taagtaccgc ctatagagtc   5040
tataggccca ccccttggc ttcttatgca tgctatactg ttttttggctt ggggtctata   5100 cacccccgct tcctcatgtt ataggtgatg gtatagctta gcctataggt gtgggttatt   5160
gaccattatt gaccactccc ctattggtga cgatactttc cattactaat ccataacatg   5220
gctctttgcc acaactctct ttattggcta tatgccaata cactgtcctt cagagactga   5280
cacggactct gtatttttac aggatgggt ctcatttatt atttacaaat tcacatatac    5340
aacaccaccg tccccagtgc ccgcagtttt tattaaacat aacgtgggat ctccacgcga   5400
atctcgggta cgtgttccgg acatgggctc ttctccggta gcgcggagc ttctacatcc    5460 gagccctgct cccatgcctc cagcgactca tggtcgctcg gcagctcctt gctcctaaca   5520
gtggaggcca gacttaggca cagcacgatg cccaccacca ccagtgtgcc gcacaaggcc   5580
gtggcggtag ggtatgtgtc tgaaaatgag ctcggggagc gggcttgcac cgctgacgca   5640
```

```
tttggaagac ttaaggcagc ggcagaagaa gatgcaggca gctgagttgt tgtgttctga    5700
taagagtcag aggtaactcc cgttgcggtg ctgttaacgg tggagggcag tgtagtctga    5760
gcagtactcg ttgctgccgc gcgcgccacc agacataata gctgacagac taacagactg    5820
ttcctttcca tgggtctttt ctgca                                          5845

<210> SEQ ID NO 2
<211> LENGTH: 5899
<212> TYPE: DNA
<213> ORGANISM: Borrelia burgdorferi

<400> SEQUENCE: 2
ctgtgcacaa aaaggtgctg agtcaattgg ttctcaaaaa gaaaatgatc taaaccttga      60
agactctagt aaaaaatcac atcaaaacgc taaacaagac cttcctgcgg tgacagaaga     120
ctcagtgtct ttgttttaatg gtaataaaat ttttgtaagc aaagaaaaaa atagctccgg    180
caaatatgat ttaagagcaa caattgatca ggttgaactt aaaggaactt ccgataaaaa     240
caatggttct ggaacccttg aaggttcaaa gcctgacaag agtaaagtaa aattaacagt     300
ttctgctgat ttaaacacag taaccttaga agcatttgat gccagcaacc aaaaaatttc     360
aagtaaagtt actaaaaaac aggggtcaat aacagaggaa actctcaaag ctaataaatt     420
agactcaaag aaattaacaa gatcaaacgg aactacactt gaatactcac aaataacaga     480
tgctgacaat gctacaaaag cagtagaaac tctaaaaaat agcattaagc ttgaaggaag     540
tcttgtagtc ggaaaaacaa cagtggaaat taagaaggt actgttactc taaaaagaga     600
aattgaaaaa gatggaaaag taaagtctct tttgaatgac actgcaggtt ctaacaaaaa     660
aacaggtaaa tgggaagaca gtactagcac tttaacaatt agtgctgaca gcaaaaaaac     720
taaagatttg gtgttcttaa cagatggtac aattacagta caacaataca acacagctgg     780
aaccagccta gaaggatcag caagtgaaat taaaaatctt tcagagctta aaaacgcttt     840
taaaataata tataggatcc agatctgctg tgccttctag ttgccagcca tctgttgttt     900
gccccctccc cgtgccttcc ttgacccctgg aaggtgccac tcccactgtc ctttcctaat     960
aaaatgagga aattgcatcg cattgtctga gtaggtgtca tctattctgg ggggtggggt    1020
ggggcagcac agcaagggg aggattggga agacaatagc aggcatgctg gggatgcggt     1080
gggctctatg ggtacccagg tgctgaagaa ttgacccggt tcctcctggg ccagaaagaa    1140
gcaggcacat ccccttctct gtgacacacc ctgtccacgc cctggttct tagttccagc     1200 cccactcata ggacactcat agctcaggag ggctccgcct tcaatcccac ccgctaaagt     1260
acttggagcg gtctctcccct ccctcatcag cccaccaaac caaacctagc ctccaagagt    1320
gggaagaaat taaagcaaga taggctatta agtgcagagg gagagaaaat gcctccaaca    1380
tgtgaggaag taatgagaga aatcatagaa tttcttccgc ttcctcgctc actgactcgc    1440
tgcgctcggt cgttcggctg cggcgagcgg tatcagctca ctcaaaggcg gtaatacggt    1500
tatccacaga atcaggggat aacgcaggaa agaacatgtg agcaaaaggc cagcaaaagg    1560
ccaggaaccg taaaaaggcc gcgttgctgg cgttttttcca taggctccgc cccctgacg    1620 agcatcacaa aaatcgacgc tcaagtcaga ggtggcgaaa cccgacagga ctataaagat    1680
accaggcgtt tcccctggaa gctccctcg tgcgctctcc tgttccgacc ctgccgctta    1740
ccggatacct gtccgccttt ctcccttcgg gaagcgtggc gctttctcaa tgctcacgct    1800
gtaggtatct cagttcggtg taggtcgttc gctccaagct gggctgtgtg cacgaacccc    1860
ccgttcagcc cgaccgctgc gccttatccg gtaactatcg tcttgagtcc aacccggtaa    1920
```

```
gacacgactt atcgccactg gcagcagcca ctggtaacag gattagcaga gcgaggtatg    1980
taggcggtgc tacagagttc ttgaagtggt ggcctaacta cggctacact agaaggacag    2040
tatttggtat ctgcgctctg ctgaagccag ttaccttcgg aaaaagagtt ggtagctctt    2100
gatccggcaa acaaaccacc gctggtagcg gtggttttt tgtttgcaag cagcagatta    2160
cgcgcagaaa aaaggatctc aagaagatcc tttgatcttt tctacgggg tctgacgctc    2220 agtggaacga aaactcacgt taagggattt tggtcatgag attatcaaaa aggatcttca    2280
cctagatcct tttaaattaa aaatgaagtt ttaaatcaat ctaaagtata tatgagtaaa    2340
cttggtctga cagttaccaa tgcttaatca gtgaggcacc tatctcagcg atctgtctat    2400
ttcgttcatc catagttgcc tgactccggg gggggggggc gctgaggtct gcctcgtgaa    2460
gaaggtgttg ctgactcata ccaggcctga atcgccccat catccagcca gaaagtgagg    2520
gagccacggt tgatgagagc tttgttgtag gtggaccagt tggtgatttt gaacttttgc    2580
tttgccacgg aacggtctgc gttgtcggga agatgcgtga tctgatcctt caactcagca    2640
aaagttcgat ttattcaaca aagccgccgt cccgtcaagt cagcgtaatg ctctgccagt    2700
gttacaacca attaaccaat tctgattaga aaaactcatc gagcatcaaa tgaaactgca    2760
atttattcat atcaggatta tcaataccat attttttgaaa aagccgtttc tgtaatgaag    2820
gagaaaactc accgaggcag ttccatagga tggcaagatc ctggtatcgg tctgcgattc    2880
cgactcgtcc aacatcaata caacctatta atttcccctc gtcaaaaata aggttatcaa    2940
gtgagaaatc accatgagtg acgactgaat ccggtgagaa tggcaaaagc ttatgcattt    3000
ctttccagac ttgttcaaca ggccagccat tacgctcgtc atcaaaatca ctcgcatcaa    3060
ccaaaccgtt attcattcgt gattgcgcct gagcgagacg aaatacgcga tcgctgttaa    3120
aaggacaatt acaaacagga atcgaatgca accggcgcag gaacactgcc agcgcatcaa    3180 caatatttc acctgaatca ggatattctt ctaatacctg gaatgctgtt ttcccgggga    3240
tcgcagtggt gagtaaccat gcatcatcag gagtacggat aaaatgcttg atggtcggaa    3300
gaggcataaa ttccgtcagc cagtttagtc tgaccatctc atctgtaaca tcattggcaa    3360
cgctaccttt gccatgtttc agaaacaact ctggcgcatc gggcttccca tacaatcgat    3420
agattgtcgc acctgattgc ccgacattat cgcgagccca tttataccca tataaatcag    3480
catccatgtt ggaatttaat cgcggcctcg agcaagacgt ttcccgttga atatggctca    3540
taacacccct tgtattactg tttatgtaag cagacagttt tattgttcat gatgatatat    3600
ttttatcttg tgcaatgtaa catcagagat tttgagacac aacgtggctt tcccccccc    3660 cccattattg aagcatttat cagggttatt gtctcatgag cggatacata tttgaatgta    3720
tttagaaaaa taaacaaata ggggttccgc gcacatttcc ccgaaaagtg ccacctgacg    3780
tctaagaaac cattattatc atgacattaa cctataaaaa taggcgtatc acgaggccct    3840
ttcgtctcgc gcgtttcggt gatgacggtg aaaacctctg acacatgcag ctcccggaga    3900
cggtcacagc ttgtctgtaa gcggatgccg ggagcagaca agcccgtcag ggcgcgtcag    3960
cgggtgttgg cgggtgtcgg ggctggctta actatgcggc atcagagcag attgtactga    4020
gagtgcacca tatgcggtgt gaaataccgc acagatgcgt aaggagaaaa taccgcatca    4080
gattggctat tggccattgc atacgttgta tccatatcat aatatgtaca tttatattgg    4140
ctcatgtcca acattaccgc catgttgaca ttgattattg actagttatt aatagtaatc    4200
aattacgggg tcattagttc atagcccata tatggagttc cgcgttacat aacttacggt    4260
```

```
aaatgcccg cctggctgac cgcccaacga cccccgccca ttgacgtcaa taatgacgta    4320
tgttcccata gtaacgccaa tagggacttt ccattgacgt caatgggtgg agtatttacg    4380
gtaaactgcc cacttggcag tacatcaagt gtatcatatg ccaagtacgc ccctattga     4440 cgtcaatgac ggtaaatggc ccgcctggca ttatgcccag tacatgacct tatgggactt    4500
tcctacttgg cagtacatct acgtattagt catcgctatt accatggtga tgcggttttg    4560
gcagtacatc aatgggcgtg atagcggtt tgactcacgg ggatttccaa gtctccaccc    4620
cattgacgtc aatgggagtt tgttttggca ccaaaatcaa cgggactttc caaaatgtcg    4680
taacaactcc gccccattga cgcaaatggg cggtaggcgt gtacggtggg aggtctatat    4740
aagcagagct cgtttagtga accgtcagat cgcctggaga cgccatccac gctgttttga    4800
cctccataga agacaccggg accgatccag cctccgcggc cgggaacggt gcattggaac    4860
gcggattccc cgtgccaaga gtgacgtaag taccgcctat agagtctata ggcccacccc    4920
cttggcttct tatgcatgct atactgtttt tggcttgggg tctatacacc cccgcttcct    4980
catgttatag gtgatggtat agcttagcct ataggtgtgg gttattgacc attattgacc    5040
actcccctat tggtgacgat actttccatt actaatccat aacatggctc tttgccacaa    5100
ctctctttat tggctatatg ccaatacact gtccttcaga gactgacacg gactctgtat    5160
ttttacagga tggggtctca tttattattt acaaattcac atatacaaca ccaccgtccc    5220
cagtgcccgc agtttttatt aaacataacg tgggatctcc acgcgaatct cgggtacgtg    5280
ttccggacat gggctcttct ccggtagcgg cggagcttct acatccgagc cctgctccca    5340
tgcctccagc gactcatggt cgctcggcag ctccttgctc ctaacagtgg aggccagact    5400
taggcacagc acgatgccca ccaccaccag tgtgccgcac aaggccgtgg cggtagggta    5460
tgtgtctgaa aatgagctcg gggagcgggc ttgcaccgct gacgcatttg aagacttaa     5520 ggcagcggca gaagaagatg caggcagctg agttgttgtg ttctgataag agtcagaggt    5580
aactcccgtt gcggtgctgt taacggtgga gggcagtgta gtctgagcag tactcgttgc    5640
tgccgcgcgc gccaccagac ataatagctg acagactaac agactgttcc tttccatggg    5700
tcttttctgc agtcaccgtc gtcgaccaga gctgagatcc tacaggagtc cagggctgga    5760
gagaaaacct ctgcgaggaa agggaaggag caagccgtga atttaaggga cgctgtgaag    5820
caatcatgga tgcaatgaag agagggctct gctgtgtgct gctgctgtgt ggagcagtct    5880
tcgtttcgcc cagcggtac                                                 5899
```

<210> SEQ ID NO 3
<211> LENGTH: 4016
<212> TYPE: DNA
<213> ORGANISM: Borrelia burgdorferi
<220> FEATURE:
<221> NAME/KEY: misc_feature
<222> LOCATION: (6)..(29)
<223> OTHER INFORMATION: N stands for A or G or C or T
<221> NAME/KEY: misc_feature
<222> LOCATION: (1078)..(1085)
<223> OTHER INFORMATION: N stands for A or G or C or T

<400> SEQUENCE: 3

```
gatccnnnnn nnnnnnnnnn nnnnnnnnna agcttaatta gaaccaaact taattaaaac    60
caaacttaat tgaagttatt atcattttat tttttttcaa ttttctattt gttattgtta    120
atcttataat ataattatac ttgtattaag ttatattaat ataaaaggag aatatattat    180
gaaaaaatat ttattgggaa taggtctaat attagcctta atagcatgta agcaaaatgt    240
```

-continued

```
tagcagcctt gacgagaaaa acagcgtttc agtagatttg cctggtgaaa tgaaagttct    300
tgtaagcaaa gaaaaaaaca aagacggcaa gtacgatcta attgcaacag tagacaagct    360
tgagcttaaa ggaacttctg ataaaaacaa tggatctgga gtacttgaag gcgtaaaagc    420
tgacaaaagt aaagtaaaat taacaatttc tgacgatcta ggtcaaacca cacttgaagt    480
tttcaaagaa gatggcaaaa cactagtatc aaaaaaagta acttccaaag acaagtcatc    540
aacagaagaa aaattcaatg aaaaaggtga agtatctgaa aaaataataa caagagcaga    600
cggaaccaga cttgaataca cagaaattaa aagcgatgga tctggaaaag ctaaagaggt    660
tttaaaaggc tatgttcttg aaggaactct aactgctgaa aaaacaacat tggtggttaa    720
agaaggaact gttactttaa gcaaaaatat ttcaaaatct ggggaagttt cagttgaact    780
taatgacact gacagtagtg ctgctactaa aaaaactgca gcttggaatt caggcacttc    840
aactttaaca attactgtaa acagtaaaaa actaaagac cttgtgttta caaaagaaaa    900
cacaattaca gtacaacaat acgactcaaa tggcaccaaa ttagagggt cagcagttga    960 aattacaaaa cttgatgaaa ttaaaaacgc tttaaaataa ggagaattta tgagattatt    1020
aataggattt gctttagcgt tagctttaat aggatgtgca caaaaaggtg ctgagtcnnn    1080
nnnnngttgg gaattcgtaa tcatggtcat agctgtttcc tgtgtgaaat tgttatccgc    1140
tcacaattcc acacaacata cgagccggaa gcataaagtg taaagcctgg ggtgcctaat    1200
gagtgagcta actcacatta ttgcgttgc gctcactgcc cgctttccag tcgggaaacc    1260
tgtcgtgcca gctgcattaa tgaatcggcc aacgcgcggg gagaggcggt ttgcgtattg    1320
ggcgctcttc cgcttcctcg ctcactgact cgctgcgctc ggtcgttcgg ctgcggcgag    1380
cggtatcagc tcactcaaag gcggtaatac ggttatccac agaatcaggg gataacgcag    1440
gaaagaacat gtgagcaaaa ggccagcaaa aggccaggaa ccgtaaaaag ccgcgttgc    1500 tggcgttttt ccataggctc cgcccccctg acgagcatca caaaaatcga cgctcaagtc    1560
agaggtggcg aaacccgaca ggactataaa gataccaggc gtttccccct ggaagctccc    1620
tcgtgcgctc tcctgttccg accctgccgc ttaccggata cctgtccgcc tttctccctt    1680
cgggaagcgt ggcgctttct catagctcac gctgtaggta tctcagttcg gtgtaggtcg    1740
ttcgctccaa gctgggctgt gtgcacgaac cccccgttca gcccgaccgc tgcgccttat    1800
ccggtaacta tcgtcttgag tccaacccgg taagacacga cttatcgcca ctggcagcag    1860
ccactggtaa caggattagc agagcgaggt atgtaggcgg tgctacagag ttcttgaagt    1920
ggtggcctaa ctacggctac actagaagga cagtatttgg tatctgcgct ctgctgaagc    1980
cagttacctt cggaaaaaga gttggtagct cttgatccgg caaacaaacc accgctggta    2040
gcggtggttt ttttgtttgc aagcagcaga ttacgcgcag aaaaaaagga tctcaagaag    2100
atcctttgat cttttctacg gggtctgacg ctcagtggaa cgaaaactca cgttaaggga    2160
ttttggtcat gagattatca aaaggatct tcacctagat ccttttaaat taaaaatgaa    2220
gttttaaatc aatctaaagt atatatgagt aaacttggtc tgacagttac caatgcttaa    2280
tcagtgaggc acctatctca gcgatctgtc tatttcgttc atccatagtt gcctgactcc    2340
ccgtcgtgta gataactacg atacgggagg gcttaccatc tggccccagt gctgcaatga    2400
taccgcgaga cccacgctca ccggctccag atttatcagc aataaaccag ccagccggaa    2460
gggccgagcg cagaagtggt cctgcaactt tatccgcctc catccagtct attaattgtt    2520
gccgggaagc tagagtaagt agttcgccag ttaatagttt cgcaacgtt gttgccattg    2580 ctacaggcat cgtggtgtca cgctcgtcgt ttggtatggc ttcattcagc tccggttccc    2640
```

-continued

```
aacgatcaag gcgagttaca tgatccccca tgttgtgcaa aaaagcggtt agctccttcg    2700
gtcctccgat cgttgtcaga agtaagttgg ccgcagtgtt atcactcatg gttatggcag    2760
cactgcataa ttctcttact gtcatgccat ccgtaagatg cttttctgtg actggtgagt    2820
actcaaccaa gtcattctga gaatagtgta tgcggcgacc gagttgctct tgcccggcgt    2880
caatacggga taataccgcg ccacatagca gaactttaaa agtgctcatc attggaaaac    2940
gttcttcggg gcgaaaactc tcaaggatct taccgctgtt gagatccagt tcgatgtaac    3000
ccactcgtgc acccaactga tcttcagcat cttttacttt caccagcgtt tctgggtgag    3060
caaaaacagg aaggcaaaat gccgcaaaaa agggaataag ggcgacacgg aaatgttgaa    3120
tactcatact cttcctttt caatattatt gaagcattta tcagggttat tgtctcatga     3180
gcggatacat atttgaatgt atttagaaaa ataaacaaat aggggttccg cgcacatttc    3240
cccgaaaagt gccacctgac gtctaagaaa ccattattat catgacatta acctataaaa    3300
ataggcgtat cacgaggccc tttcgtctcg cgcgtttcgg tgatgacggt gaaaacctct    3360
gacacatgca gctcccggag acggtcacag cttgtctgta gcggatgcc gggagcagac      3420 aagcccgtca gggcgcgtca gcgggtgttg gcgggtgtcg gggctggctt aactatgcgg    3480
catcagagca gattgtactg agagtgcacc atatgcggtg tgaaataccg cacagatgcg    3540
taaggagaaa ataccgcatc aggcgccatt cgccattcag gctgcgcaac tgttgggaag    3600
ggcgatcggt gcgggcctct tcgctattac gccagctggc gaaaggggga tgtgctgcaa    3660
ggcgattaag ttgggtaacg ccagggtttt cccagtcacg acgttgtaaa acgacggcca    3720
gtgccaagct tggctgcagg tcgacgctct cccttatgcg actcctgcat taggaagcag    3780
cccagtagta ggttgaggcc gttgagcacc gccgccgcaa ggaatggtgc atgcaaggag    3840
atggcgccca acagtccccc ggccacgggg cctgccacca tacccacgcc gaaacaagcg    3900
ctcatgagcc cgaagtggcg agcccgatct tccccatcgg tgatgtcggc gatataggcg    3960
ccagcaaccg cacctgtggc gccggtgatg ccggccacga tgcgtccggc gtagag       4016
```

<210> SEQ ID NO 4
<211> LENGTH: 3799
<212> TYPE: DNA
<213> ORGANISM: Borrelia burgdorferi
<220> FEATURE:
<221> NAME/KEY: misc_feature
<222> LOCATION: (1118)..(1125)
<223> OTHER INFORMATION: N stands for A or G or C or T
<221> NAME/KEY: misc_feature
<222> LOCATION: (1130)..(1137)
<223> OTHER INFORMATION: N stands for A or G or C or T

<400> SEQUENCE: 4

```
aattcaggca cttcaacttt aacaattact gtaaacagta aaaaaactaa agaccttgtg      60
tttacaaaag aaaacacaat tacagtacaa caatacgact caaatggcac caaattagag    120
gggtcagcag ttgaaattac aaaacttgat gaaattaaaa acgctttaaa ataaggagaa    180
tttatgagat tattaatagg atttgcttta gcgttagctt aataggatg tgcacaaaaa     240 ggtgctgagt caattggttc tcaaaaagaa aatgatctaa accttgaaga ctctagtaaa    300
aaatcacatc aaaacgctaa acaagacctt cctgcggtga cagaagactc agtgtctttg    360
tttaatggta taaaatttt tgtaagcaaa gaaaaaata gctccggcaa atatgattta     420
agagcaacaa ttgatcaggt tgaacttaaa ggaacttccg ataaaaacaa tggttctgga    480
acccttgaag gttcaaagcc tgacaagagt aaagtaaaat taacagtttc tgctgattta    540
```

-continued

```
aacacagtaa ccttagaagc atttgatgcc agcaaccaaa aaatttcaag taaagttact    600
aaaaaacagg ggtcaataac agaggaaact ctcaaagcta ataaattaga ctcaaagaaa    660
ttaacaagat caaacggaac tacacttgaa tactcacaaa taacagatgc tgacaatgct    720
acaaaagcag tagaaactct aaaaaatagc attaagcttg aaggaagtct tgtagtcgga    780
aaaacaacag tggaaattaa agaaggtact gttactctaa aaagagaaat tgaaaaagat    840
ggaaaagtaa aagtcttttt gaatgacact gcaggttcta acaaaaaaac aggtaaatgg    900
gaagacagta ctagcacttt aacaattagt gctgacagca aaaaaactaa agatttggtg    960
ttcttaacag atggtacaat tacagtacaa caatacaaca cagctggaac cagcctagaa   1020
ggatcagcaa gtgaaattaa aaatctttca gagcttaaaa acgctttaaa ataatatata   1080
agtaaacccc ctacaaggca tcagctagtg taggaagnnn nnnnnggccn nnnnnnngtt   1140
ggggatccgt cgacctgcag ccaagcttgg cgtaatcatg gtcatagctg tttcctgtgt   1200
gaaattgtta tccgctcaca attccacaca acatacgagc cggaagcata agtgtaaag   1260 cctggggtgc ctaatgagtg agctaactca cattaattgc gttgcgctca ctgcccgctt   1320
tccagtcggg aaacctgtcg tgccagctgc attaatgaat cggccaacgc gcggggagag   1380
gcggtttgcg tattgggcgc tcttccgctt cctcgctcac tgactcgctg cgctcggtcg   1440
ttcggctgcg gcgagcggta tcagctcact caaaggcggt aatacggtta ccacagaat   1500 cagggGataa cgcaggaaag aacatgtgag caaaaggcca gcaaaaggcc aggaaccgta   1560
aaaaggccgc gttgctggcg tttttccata ggctccgccc cctgacgag catcacaaaa   1620 atcgacgctc aagtcagagg tggcgaaacc cgacaggact ataaagatac caggcgtttc   1680
cccctggaag ctccctcgtg cgctctcctg ttccgaccct gccgcttacc ggatacctgt   1740
ccgcctttct cccttcggga agcgtggcgc tttctcatag ctcacgctgt aggtatctca   1800
gttcggtgta ggtcgttcgc tccaagctgg gctgtgtgca cgaaccccc gttcagcccg    1860 accgctgcgc cttatccggt aactatcgtc ttgagtccaa cccggtaaga cacgacttat   1920
cgccactggc agcagccact ggtaacagga ttagcagagc gaggtatgta ggcggtgcta   1980
cagagttctt gaagtggtgg cctaactacg gctacactag aaggacagta tttggtatct   2040
gcgctctgct gaagccagtt accttcggaa aaagagttgg tagctcttga tccggcaaac   2100
aaaccaccgc tggtagcggt ggtttttttg tttgcaagca gcagattacg cgcagaaaaa   2160
aaggatctca agaagatcct ttgatctttt ctacgggtc tgacgctcag tggaacgaaa   2220
actcacgtta agggattttg gtcatgagat tatcaaaaag gatcttcacc tagatccttt   2280
taaattaaaa atgaagtttt aaatcaatct aaagtatata tgagtaaact tggtctgaca   2340
gttaccaatg cttaatcagt gaggcaccta tctcagcgat ctgtctattt cgttcatcca   2400
tagttgcctg actccccgtc gtgtagataa ctacgatacg ggagggctta ccatctggcc   2460
ccagtgctgc aatgataccg cgagacccac gctcaccggc tccagattta tcagcaataa   2520
accagccagc cggaagggcc gagcgcagaa gtggtcctgc aactttatcc gcctccatcc   2580
agtctattaa ttgttgccgg gaagctagag taagtagttc gccagttaat agtttgcgca   2640
acgttgttgc cattgctaca ggcatcgtgg tgtcacgctc gtcgtttggt atggcttcat   2700
ttcagctccg gttcccaacg atcaaggcga gttacatgat cccccatgtt gtgcaaaaaa   2760
gcggttagct ccttcggtcc tccgatcgtt gtcagaagta agttggccgc agtgttatca   2820
ctcatggtta tggcagcact gcataattct cttactgtca tgccatccgt aagatgcttt   2880
```

-continued

```
tctgtgactg gtgagtactc aaccaagtca ttctgagaat agtgtatgcg gcgaccgagt        2940
tgctcttgcc cggcgtcaat acgggataat accgcgccac atagcagaac tttaaaagtg        3000
ctcatcattg gaaaacgttc ttcggggcga aaactctcaa ggatcttacc gctgttgaga        3060
tccagttcga tgtaacccac tcgtgcaccc aactgatctt cagcatcttt tactttcacc        3120
agcgtttctg ggtgagcaaa aacaggaagg caaaatgccg caaaaaaggg aataagggcg        3180
acacggaaat gttgaatact catactcttc cttttttcaat attattgaag catttatcag       3240
ggttattgtc tcatgagcgg atacatattt gaatgtattt agaaaaataa acaaataggg        3300
gttccgcgca catttccccg aaaagtgcca cctgacgtct aagaaaccat tattatcatg        3360
acattaacct ataaaaatag gcgtatcacg aggccctttc gtctcgcgcg tttcggtgat        3420
gacggtgaaa acctctgaca catgcagctc ccggagacgg tcacagcttg tctgtaagcg        3480
gatgccggga gcagacaagc ccgtcagggc gcgtcagcgg gtgttggcgg gtgtcggggc        3540
tggcttaact atgcggcatc agagcagatt gtactgagag tgcaccatat gcggtgtgaa        3600
ataccgcaca gatgcgtaag gagaaaatac cgcatcaggc gccattcgcc attcaggctg        3660
cgcaactgtt gggaagggcg atcggtgcgg gcctcttcgc tattacgcca gctggcgaaa        3720
gggggatgtg ctgcaaggcg attaagttgg gtaacgccag ggttttccca gtcacgacgt        3780
tgtaaaacga cggccagtg                                                     3799
```

<210> SEQ ID NO 5
<211> LENGTH: 1917
<212> TYPE: DNA
<213> ORGANISM: Borrelia burgdorferi

<400> SEQUENCE: 5

```
ctagcttaat tagaaccaaa cttaattaaa accaaactta attgaagtta ttatcatttt          60 atttttttc aattttctat tgttatttta ttaatcttat aatataatta tacttgtatt         120
aagttatatt aatataaaag gagaatatat tatgaaaaaa tatttattgg gaataggtct         180
aatattagcc ttaatagcat gtaagcaaaa tgttagcagc cttgacgaga aaacagcgt          240 ttcagtagat ttgcctggtg aaatgaaagt tcttgtaagc aaagaaaaaa acaaagacgg         300
caagtacgat ctaattgcaa cagtagacaa gcttgagctt aaaggaactt ctgataaaaa         360
caatggatct ggagtacttg aaggcgtaaa agctgacaaa agtaaagtaa aattaacaat         420
ttctgacgat ctaggtcaaa ccacacttga agttttcaaa aagatggca aaacactagt          480 atcaaaaaaa gtaacttcca agacaagtc atcaacagaa gaaaaattca atgaaaaagg         540
tgaagtatct gaaaaaataa taacaagagc agacggaacc agacttgaat acacagaaat         600
taaaagcgat ggatctggaa aagctaaaga ggttttaaaa ggctatgttc ttgaaggaac         660
tctaactgct gaaaaaacaa cattggtggt taaagaagga actgttactt taagcaaaaa         720
tatttcaaaa tctgggggaag tttcagttga acttaatgac actgacagta gtgctgctac         780
taaaaaaact gcagcttgga attcaggcac ttcaacttta acaattactg taaacagtaa         840
aaaaactaaa gaccttgtgt ttacaaaaga aaacacaatt acagtacaac aatacgactc         900
aaatggcacc aaattagagg ggtcagcagt tgaaattaca aaacttgatg aaattaaaaa         960
cgctttaaaa taaggagaat ttatgagatt attaatagga tttgctttag cgttagcttt        1020
aataggatgt gcacaaaaag gtgctgagtc aattggttct caaaaagaaa atgatctaaa        1080
ccttgaagac tctagtaaaa aatcacatca aaacgctaaa caagaccttc ctgcggtgac        1140
agaagactca gtgtctttgt ttaatggtaa taaaattttt gtaagcaaag aaaaaaatag        1200
```

-continued ctccggcaaa tatgatttaa gagcaacaat tgatcaggtt gaacttaaag gaacttccga 1260
taaaaacaat ggttctggaa cccttgaagg ttcaaagcct gacaagagta aagtaaaatt 1320
aacagtttct gctgatttaa acacagtaac cttagaagca tttgatgcca gcaaccaaaa 1380
aatttcaagt aaagttacta aaaaacaggg gtcaataaca gaggaaactc tcaaagctaa 1440
taaattagac tcaaagaaat taacaagatc aaacggaact acacttgaat actcacaaat 1500
aacagatgct gacaatgcta caaaagcagt agaaactcta aaaaatagca ttaagcttga 1560
aggaagtctt gtaggcggaa aaacaacagt ggaaattaaa gaaggtactg ttactctaaa 1620
aagagaaatt gaaaaagatg gaaaagtaaa agtctttttg aatgacactg caggttctaa 1680
caaaaaaaca ggtaaatagg aagacagtac tagcacttta acaattagtg ctgacagcac 1740
aaaaactaaa gatttggtgt tcttaacaga tggtacaatt acagtacaac aatacaacac 1800
agctggaacc agcctagaag gatcagcaag tgaaattaaa aatctttcag agcttaaaaa 1860
cgctttaaaa taatatataa gtaaaccccc ctacaaggca tcagctagtg taggaag 1917

<210> SEQ ID NO 6
<211> LENGTH: 320
<212> TYPE: DNA
<213> ORGANISM: Borrelia burgdorferi

<400> SEQUENCE: 6
gttcctttcc atgggtcttt tctgcagtca ccgtcgtcga caaggaaagg tacccagaaa 60
agacgtcagt ggcagcagct cacgtgtgat cagatatcgc ggccgctcta gaccaggcgc 120
gtgcacacta gtctatagcg ccgtcgagat ctggtccgcg ctggatccag atctgctgtg 180
ccttctagtt gccagccatc gacctaggtc tagacgacac ggaagatcaa cggtcggtag 240
tgttgtttgc cctcccccg tgccttcctt gaccctggaa acaacaaacg gggaggggc 300 acggaaggaa ctgggacctt 320

<210> SEQ ID NO 7
<211> LENGTH: 4915
<212> TYPE: DNA
<213> ORGANISM: Borrelia burgdorferi

<400> SEQUENCE: 7
ctcgcgcgtt tcggtgatga cggtgaaaac ctctgacaca tgcagctccc ggagacggtc 60
acagcttgtc tgtaagcgga tgccgggagc agacaagccc gtcagggcgc gtcagcgggt 120
gttggcgggt gtcggggctg gcttaactat gcggcatcag agcagattgt actgagagtg 180
caccatatgc ggtgtgaaat accgcacaga tgcgtaagga gaaaataccg catcagattg 240
gctattggcc attgcatacg ttgtatccat atcataatat gtacatttat attggctcat 300
gtccaacatt accgccatgt tgacattgat tattgactag ttattaatag taatcaatta 360
cggggtcatt agttcatagc ccatatatgg agttccgcgt tacataactt acggtaaatg 420
gcccgcctgg ctgaccgccc aacgaccccc gcccattgac gtcaataatg acgtatgttc 480
ccatagtaac gccaataggg actttccatt gacgtcaatg ggtggagtat ttacggtaaa 540
ctgcccactt ggcagtacat caagtgtatc atatgccaag tacgccccct attgacgtca 600
atgacggtaa atggcccgcc tggcattatg cccagtacat gaccttatgg gactttcct 660 acttggcagt acatctacgt attagtcatc gctattacca tggtgatgcg gttttggcag 720
tacatcaatg ggcgtggata gcggtttgac tcacggggat ttccaagtct ccaccccatt 780

-continued

| | |
|---|---|
| gacgtcaatg ggagtttgtt ttggcaccaa atcaacggg actttccaaa atgtcgtaac | 840 |
| aactccgccc cattgacgca aatgggcggt aggcgtgtac ggtgggaggt ctatataagc | 900 |
| agagctcgtt tagtgaaccg tcagatcgcc tggagacgcc atccacgctg ttttgacctc | 960 |
| catagaagac accgggaccg atccagcctc cgcggccggg aacggtgcat tggaacgcgg | 1020 |
| attccccgtg ccaagagtga cgtaagtacc gcctatagag tctataggcc caccccttg | 1080 |
| gcttatgcat gctatactgt ttttggcttg ggtctatac accccgctt cctcatgtta | 1140 |
| taggtgatgg tatagcttag cctataggtg tgggttattg accattattg accactcccc | 1200 |
| tattggtgac gatactttcc attactaatc cataacatgg ctctttgcca caactctctt | 1260 |
| tattggctat atgccaatac actgtccttc agagactgac acggactctg tattttaca | 1320 |
| ggatggggtc tcatttatta tttacaaatt cacatataca acaccaccgt ccccagtgcc | 1380 |
| cgcagttttt attaaacata acgtgggatc tccacgcgaa tctcgggtac gtgttccgga | 1440 |
| catgggctct tctccggtag cggcggagct tctacatccg agccctgctc ccatgcctcc | 1500 |
| agcgactcat ggtcgctcgg cagctccttg ctcctaacag tggaggccag acttaggcac | 1560 |
| agcacgatgc ccaccaccac cagtgtgccg cacaaggccg tggcggtagg gtatgtgtct | 1620 |
| gaaaatgagc tcggggagcg ggcttgcacc gctgacgcat ttggaagact taaggcagcg | 1680 |
| gcagaagaag atgcaggcag ctgagttgtt gtgttctgat aagagtcaga ggtaactccc | 1740 |
| gttgcggtgc tgttaacggt ggagggcagt gtagtctgag cagtactcgt tgctgccgcg | 1800 |
| cgcgccacca gacataatag ctgacagact aacagactgt tcctttccat gggtcttttc | 1860 |
| tgcagtcacc gtcgtcgaca cgtgtgatca gatatcgcgg ccgctctaga ccaggcgcct | 1920 |
| ggatccagat ctgctgtgcc ttctagttgc agccatctg ttgtttgccc ctcccccgtg | 1980 |
| ccttccttga ccctggaagg tgccactccc actgtccttt cctaataaaa tgaggaaatt | 2040 |
| gcatcgcatt gtctgagtag gtgtcattct attctggggg gtggggtggg gcagcacagc | 2100 |
| aaggggagg attgggaaga caatagcagg catgctgggg atgcggtggg ctctatgggt | 2160 |
| acccaggtgc tgaagaattg acccggttcc tcctgggcca gaaagaagca ggcacatccc | 2220 |
| cttctctgtg acacaccctg tccacgcccc tggttcttag ttccagcccc actcatagga | 2280 |
| cactcatagc tcaggagggc tccgccttca atcccaccccg ctaaagtact gggagcggtc | 2340 |
| tctccctccc tcatcagccc accaaaccaa acctagcctc caagagtggg aagaaattaa | 2400 |
| agcaagatag gctattaagt gcagagggag agaaaatgcc tccaacatgt gaggaagtaa | 2460 |
| tgagagaaat catagaattt cttccgcttc ctcgctcact gactcgctgc gctcggtcgt | 2520 |
| tcggctgcgg cgagcggtat cagctcactc aaaggcggta atacggttat ccacagaatc | 2580 |
| agggataac gcaggaaaga acatgtgagc aaaaggccag caaaaggcca ggaaccgtaa | 2640 |
| aaaggccgcg ttgctggcgt ttttccatag gctccgcccc cctgacgagc atcacaaaaa | 2700 |
| tcgacgctca agtcagaggt ggcgaaaccc gacaggacta taaagatacc aggcgtttcc | 2760 |
| ccctggaagc tccctcgtgc gctctcctgt tccgaccctg ccgcttaccg gatacctgtc | 2820 |
| cgcctttctc ccttcgggaa gcgtggcgct ttctcaatgc tcacgctgta ggtatctcag | 2880 |
| ttcggtgtag tcgttcgct ccaagctggg ctgtgtgcac gaaccccccg ttcagcccga | 2940 |
| ccgctgcgcc ttatccggta actatcgtct tgagtccaac ccggtaagac acgacttatc | 3000 |
| gccactggca gcagccactg gtaacaggat tagcagagcg aggtatgtag gcggtgctac | 3060 |
| agagttcttg aagtggtggc ctaactacgg ctacactaga aggacagtat ttggtatctg | 3120 |
| cgctctgctg aagccagtta ccttcggaaa aagagttggt agctcttgat ccggcaaaca | 3180 |

```
aaccaccgct ggtagcggtg gttttttttgt ttgcaagcag cagattacgc gcagaaaaaa      3240
aggatctcaa gaagatcctt tgatgttttc taccggggtc tgacgctcag tggaacgaaa      3300
actcacgtta agggattttg gtcatgagat tatcaaaaag gatcttcacc tagatccttt      3360
taaattaaaa atgaagtttt aaatcaatct aaagtatata tgagtaaact tggtctgaca      3420
gttaccaatg cttaatcagt gaggcaccta tctcagcgat ctgtctattt cgttcatcca      3480
tagttgcctg actccggggg ggggggggcgc tgaggtctgc ctcgtgaaga aggtgttgct      3540
gactcatacc aggcctgaat cgccccatca tccagccaga aagtgaggga gccacggttg      3600
atgagagctt tgttgtaggt ggaccagttg gtgattttga acttttgctt tgccacggaa      3660
cggtctgcgt tgtcgggaag atgcgtgatc tgatccttca actcagcaaa agttcgattt      3720
attcaacaaa gccgccgtcc cgtcaagtca gcgtaatgct ctgccagtgt tacaaccaat      3780
taaccaattc tgattagaaa aactcatcga gcatcaaatg aaactgcaat ttattcatat      3840
caggattatc aataccatat ttttgaaaaa gccgtttctg taatgaagga gaaaactcac      3900
cgaggcagtt ccataggatg gcaagatcct ggtatcggtc tgcgattccg actcgtccaa      3960
catcaataca acctattaat ttcccctcgt caaaaataag gttatcaagt gagaaatcac      4020
catgagtgac gactgaatcc ggtgagaatg gcaaaagctt atgcatttct ttccagactt      4080
gttcaacagg ccagccatta cgctcgtcat caaaatcact cgcatcaacc aaaccgttat      4140
tcattcgtgc attgcgcctg agcgagacga aatacgcgat cgctgttaaa aggacaatta      4200
caaacaggaa tcgaatgcaa ccggcgcagg aacactgcca gcgcatcaac aatattttca      4260
cctgaatcag gatattcttc taatacctgg aatgctgttt tcccggggat cgcagtggtg      4320
agtaaccatg catcatcagg agtacggata aaatgcttga tggtcggaag aggcataaat      4380
tccgtcagcc agtttagtct gaccatctca tctgtaacat cattggcaac gctacctttg      4440
ccatgtttca gaaacaactc tggcgcatcg ggcttcccat acaatcgata gattgtcgca      4500
cctgattgcc cgacattatc gcgagcccat ttatacccat ataaatcagc atccatgttg      4560
gaatttaatc gcggcctcga gcaagacgtt tcccgttgaa tatggctcat aacacccctt      4620
gtattactgt ttatgtaagc agacagtttt attgttcatg atgatatatt tttatcttgt      4680
gcaatgtaac atcagagatt tgagacacaa acgtggcttt cccccccccc ccattattga      4740
agcatttatc agggttattg tctcatgagc ggatacatat ttgaatgtat ttagaaaaat      4800
aaacaaatag gggttccgcg cacatttccc cgaaaagtgc cacctgacgt ctaagaaacc      4860
attattatca tgacattaac ctataaaaat aggcgtatca cgaggccctt tcgtc           4915
```

<210> SEQ ID NO 8
<211> LENGTH: 5215
<212> TYPE: DNA
<213> ORGANISM: Borrelia burgdorferi

<400> SEQUENCE: 8

```
aagcttttt tgcaaaagcc taggcctcca aaaaagcctc ctcactactt ctggaatagc        60
tcagaggccg aggcggcctc ggcctctgca taaataaaaa aaattagtca gccatggggc      120
ggagaatggg cggaactggg cgaagttagg ggcgggatgg gcggagtgaa ttattggcta      180
ttggccattg catacgttgt atctatatca taatatgtac atttatattg gctcatgtcc      240
aatatgaccg ccatgttgac attgattatt gactagttat taatagtaat caattacggg      300
gtcattagtt catagcccat atatggagtt ccgcgttaca taacttacgg taattggccc      360
```

-continued

| | | | | |
|---|---|---|---|---|
| gcctgctgac | cgcccaacga | cccccgccca | ttgacgtcaa | taatgacgta tgttcccata | 420 |
| gtaacgccaa | tagggacttt | ccattgacgt | caatgggtgg | agtatttacg gtaaactgcc | 480 |
| cacttggcag | tacatcaagt | gtatcatatg | ccaagtccgg | cccctattg acgtcaatga | 540 |
| cggtaaatgg | cccgcctggc | attatgccca | gtacatgacc | ttacgggact ttggtacttg | 600 |
| gcagtacatc | tacgtattag | tcatcgctat | taccatggtg | atgcggtttt ggcagtacac | 660 |
| caatgggcgt | ggatagcggt | ttgactcacg | ggatttcca | agtctccacc ccattgacgt | 720 |
| caatgggagt | ttgttttggc | accaaaatca | acgggacttt | ccaaaatgtc gtaataaccc | 780 |
| cgccccgttg | acgcaaatgg | gcggtaggcg | tgtacggtgg | gaggtctata taagcagagc | 840 |
| tcgtttagtg | aaccgtcaga | tcgcctggag | acgccatcca | cgctgttttg acctccatag | 900 |
| aagacaccgg | gaccgatcca | gcctccgcgg | ccgggaacgg | tgcattggaa cgcggattcc | 960 |
| ccgtgccaag | agtgacgtaa | gtaccgccta | tagactctat | aggcacaccc ctttggctct | 1020 |
| tatgcatgct | atactgtttt | tggcttgggg | cctatacacc | cccgctcctt atgctatagg | 1080 |
| tgatggtata | gcttagccta | taggtgtggg | ttattgacca | ttattgacca ctcccctatt | 1140 |
| ggtgacgata | ctttccatta | cttaatccat | aacatggctc | tttgccacaa ctatctctat | 1200 |
| tggctatatg | ccaatactct | gtccttcaga | gactgacacg | gactctgtat ttttacagga | 1260 |
| tggggtccca | tttattattt | acaaattcac | atatacaaca | acgccgtccc ccgtgccgc | 1320 |
| agttttatt | aaacatagcg | tgggatctcc | acgcgaatct | cgggtacgtg ttccggacat | 1380 |
| gggctcttct | ccggtagcgg | cggagcttcc | acatccgagc | cctggtccca tgcctccagc | 1440 |
| ggctcatggt | cgctcggcag | ctccttgctc | ctaacagtgg | aggccagact taggcacagc | 1500 |
| acaatgccca | ccaccaccag | tgtgccgcac | aaggccgtgg | cggtagggta tgtgtctgaa | 1560 |
| aatgagctcg | gagattgggc | tcgcaccgtg | acgcagatgg | aagacttaag gcagcggcag | 1620 |
| aagaagatgc | aggcagctga | gttgttgtat | tctgataaga | gtcagaggta actcccgttg | 1680 |
| cggttctgtt | aacggtggag | ggcagtgtag | tctgagcagt | actcgttgct gccgcgcgcg | 1740 |
| ccaccagaca | taatagctga | cagactaaca | gactgttcct | ttccatgggt cttttctgca | 1800 |
| gtcaccgtcg | tcgaccagag | ctgagatcct | acaggagtcc | agggctggag agaaaacctc | 1860 |
| tgcgaggaaa | gggaaggagc | aagccgtgaa | tttaagggac | gctgtgaagc aatcatggat | 1920 |
| gcaatgaaga | gagggctctg | ctgtgtgctg | ctgctgtgtg | gagcagtctt cgtttcgccc | 1980 |
| agcgctagag | gatccagatc | tctcgacatg | ggcaaatatt | atacgcaagg cgacaaggtg | 2040 |
| ctgatgccgc | tggcgattca | ggttcatcat | gccgtctgtg | atggcttcca tgtcggcaga | 2100 |
| atgcttaatg | aattacaaca | gtactgcgat | gagtggcagg | gcggggcgta atttttttaa | 2160 |
| ggcagttatt | ggtgccctta | aacgcctggt | gctacgcctg | aataagtgat aataagcgga | 2220 |
| tgaatggcag | aaattcgccg | gatctttgtg | aaggaacctt | acttctgtgg tgtgacataa | 2280 |
| ttggacaaac | tacctacaga | gatttaaagc | tctaaggtaa | atataaaatt tttaagtgta | 2340 |
| taatgtgtta | aactactgat | tctaattgtt | tgtgtatttt | agattccaac ctatggaact | 2400 |
| gatgaatggg | agcagtggtg | gaatgccttt | aatgaggaaa | acctgttttg ctcagaagaa | 2460 |
| atgccatcta | gtgatgatga | ggctactgct | gactctcaac | atttctactc ctccaaaaaa | 2520 |
| gaagagaaag | gtagaagacc | ccaaggactt | tccttcagaa | ttgctaagtt ttttgagtca | 2580 |
| tgctgtgttt | agtaatagaa | ctcttgcttg | ctttgctatt | tacaccacaa aggaaaaagc | 2640 |
| tgcactgcta | tacaagaaaa | ttatggaaaa | atattctgta | acctttataa gtaggcataa | 2700 |
| cagttataat | cataacatac | tgttttttct | tactccacac | aggcatagag tgtctgctat | 2760 |

```
taataactat gctcaaaaat tgtgtacttt agcttttttaa tttgtaaagg ggttaataag    2820
gaatatttga tgtatagtgc cttgactaga gatcataatc agccatacca catttgtaga    2880
ggttttactt gctttaaaaa acctcccaca cctcccctg aacctgaaac ataaaatgaa     2940
tgcaattgtt gttgttaact tgtttattgc agcttataat ggttacaaat aaagcaatag    3000
catcacaaat ttcacaaata aagcatttt ttcactgcat tctagttgtg gtttgtccaa     3060
actcatcaat gtatcttatc atgtctggat cgatccccgg gtaccgagct cgaattcgta    3120
atcatggtca tagctgtttc ctgtgtgaaa ttgttatccg ctcacaattc cacacaacat    3180
acgagccgga agcataaagt gtaaagcctg gggtgcctaa tgagtgagct aactcacatt    3240
aattgcgttg cgctcactgc ccgctttcca gtcgggaaac ctgtcgtgcc agctgcatta    3300
atgaatcggc caacgcgcgg ggagaggcgg tttgcgtatt gggcgctctt ccgcttcctc    3360
gctcactgac tcgctgcgct cggtcgttcg gctgcggcga gcggtatcag ctcactcaaa    3420
ggcggtaata cggttatcca cagaatcagg ggataacgca ggaaagaaca tgtgagcaaa    3480
aggccagcaa aaggccagga accgtaaaaa ggccgcgttg ctggcgtttt tccataggct    3540
ccgcccccct gacgagcatc acaaaaatcg acgctcaagt cagaggtggc gaaacccgac    3600
aggactataa agataccagg cgtttccccc tggaagctcc ctcgtgcgct ctcctgttcc    3660
gaccctgccg cttaccggat acctgtccgc ctttctccct tcgggaagcg tggcgctttc    3720
tcatagctca cgctgtaggt atctcagttc ggtgtaggtc gttcgctcca agctgggctg    3780
tgtgcacgaa ccccccgttc agcccgaccg ctgcgcctta tccggtaact atcgtcttga    3840
gtccaacccg gtaagacacg acttatcgcc actggcagca gccactggta acaggattag    3900
cagagcgagg tatgtaggcg gtgctacaga gttcttgaag tggtggccta actacggcta    3960
cactagaagg acagtatttg gtatctgcgc tctgctgaag ccagttacct tcggaaaaag    4020
agttggtagc tcttgatccg gcaaacaaac caccgctggt agcggtggtt tttttgtttg    4080
caagcagcag attacgcgca gaaaaaaagg atctcaagaa gatcctttga tcttttctac    4140
ggggtctgac gctcagtgga acgaaaactc acgttaaggg attttggtca tgaacaataa    4200
aactgtctgc ttacataaac agtaatacaa ggggtgttat gagccatatt caacgggaaa    4260
cgtcttgctc gaggccgcga ttaaattcca acatggatgc tgattatatg ggtataaatg    4320
ggctcgcgat aatgtcgggc aatcaggtgc gacaatctat cgattgtatg ggaagcccgat   4380 gcgccagagt tgtttctgaa acatggcaaa ggtagcgttg ccaatgatgt tacagatgag    4440
atggtcagac taaactggct gacggaattt atgcctcttc cgaccatcaa gcatttatcc    4500
gtactcctga tgatgcatgg ttactcacca ctgcgatccc cgggaaaaca gcattccagg    4560
tattagaaga atatcctgat tcaggtgaaa atattgttga tgcgctggca gtgttcctgc    4620
gccggttgca ttcgattcct gtttgtaatt gtccttttaa cagcgatcgc gtatttcgtc    4680
tcgctcaggc gcaatcacga atgaataacg gtttggttga tgcgagtgat tttgatgacg    4740
agcgtaatgg ctggcctgtt gaacaagtct ggaaagaaat gcataagctt ttccattctc    4800
accggattca gtcgtcactc atggtgattt ctcacttgat aaccttattt ttgacgaggg    4860
gaaattaata ggttgtattg atgttggacg agtcggaatc gcagaccgat accaggatct    4920
tgccatccta tggaactgcc tcggtgagtt ttctccttca tacagaaacg gctttttcaa    4980
aaatatggta ttgataatcc tgatatgaat aaattgcagt ttcattgatg ctcgatgagt    5040
ttttctaaga attcgccatt cgccattcag gctgcgcaac tgttgggaag ggcgatcggt    5100
```

```
gcgggcctct tcgctattac gccagctggc gaaaggggga tgtgctgcaa ggcgattaag    5160
ttgggtaacg ccagggtttt cccagtcacg acgttgtaaa acgacggcca gtgcc         5215
```

<210> SEQ ID NO 9
<211> LENGTH: 211
<212> TYPE: DNA
<213> ORGANISM: Borrelia burgdorferi

<400> SEQUENCE: 9

```
ctgcagtcac cgtcgtcgac cagagctgag atcctacagg agtccagggc tggagagaaa      60
acctctgcga ggaaagggaa ggagcaagcc gtgaatttaa gggacgctgt gaagcaatca     120
tggatgcaat gaagagaggg ctctgctgtg tgctgctgct gtgtggagca gtcttcgttt     180
cgcccagcgc tagaggatcc agatctctcg a                                    211
```

<210> SEQ ID NO 10
<211> LENGTH: 30
<212> TYPE: DNA
<213> ORGANISM: Borrelia burgdorferi

<400> SEQUENCE: 10

```
gccttaggta cctgtaagca aaatgttagc                                       30
```

<210> SEQ ID NO 11
<211> LENGTH: 42
<212> TYPE: DNA
<213> ORGANISM: Borrelia burgdorferi

<400> SEQUENCE: 11

```
taataatcta gaaaattctc cttacttaag agcgttttta at                         42
```

<210> SEQ ID NO 12
<211> LENGTH: 30
<212> TYPE: DNA
<213> ORGANISM: Borrelia burgdorferi

<400> SEQUENCE: 12

```
gctttaggta cctgtgcaca aaaaggtgct                                       30
```

<210> SEQ ID NO 13
<211> LENGTH: 30
<212> TYPE: DNA
<213> ORGANISM: Borrelia burgdorferi

<400> SEQUENCE: 13

```
aggggggat cctatatatt attttaaagc                                        30
```

<210> SEQ ID NO 14
<211> LENGTH: 21
<212> TYPE: DNA
<213> ORGANISM: Borrelia burgdorferi

<400> SEQUENCE: 14

```
tcttttctgc agtcaccgtc g                                                21
```

<210> SEQ ID NO 15
<211> LENGTH: 36
<212> TYPE: DNA
<213> ORGANISM: Borrelia burgdorferi

<400> SEQUENCE: 15

```
gagagatctg gatccggtac cgctgggcga aacgaa                                36
```

<210> SEQ ID NO 16
<211> LENGTH: 839
<212> TYPE: DNA
<213> ORGANISM: Borrelia burgdorferi

<400> SEQUENCE: 16

| | | | | | |
|---|---|---|---|---|---|
| tagctgacag | actaacagac | tgttcctttc | catgggtctt | ttctgcagtc | accgtcgtcg | 60 |
| atcgactgtc | tgattgtctg | acaaggaaag | gtacccagaa | agacgtcag | tggcagcagc | 120 |
| accagagctg | agatcctaca | ggagtccagg | gctggagaga | aaacctctgc | gaggaaaggg | 180 |
| tggtctcgac | tctaggatgt | cctcaggtcc | cgacctctct | tttggagacg | ctcctttccc | 240 |
| aaggagcaag | ccgtgaattt | aagggacgct | gtgaagcaat | catggatgca | atgaagagag | 300 |
| ttcctcgttc | ggcacttaaa | ttccctgcga | cacttcgtta | gtacctacgt | tacttctctc | 360 |
| ggctctgctg | tgtgctgctg | ctgtgtggag | cagtcttcgt | ttcgcccagc | ggtacctgta | 420 |
| ccgagacgac | acacgacgac | gacacacctc | gtcagaagca | aagcgggtcg | ccatggacat | 480 |
| agcaaaatgt | tagcagcctt | gacgagaaaa | acagcgtttc | agtagatttg | cctggtgaaa | 540 |
| tcgttttaca | atcgtcggaa | ctgctctttt | tgtcgcaaag | tcatctaaac | ggaccacttt | 600 |
| tgaaagttct | tgtaagcaaa | gaaaaaaaca | agacggcaa | gtacgatcta | attgcaacag | 660 |
| actttcaaga | acattcgttt | ctttttttgt | ttctgccgtt | catgctagtt | aacgttgtct | 720 |
| agacaagctt | gagcttaaag | gaacttctga | taaaaacaat | ggatctggag | tacttgaaga | 780 |
| tctgttcgaa | ctcgaatttc | cttgaagact | attttttgtta | cctagacctc | atgaacttc | 839 |

<210> SEQ ID NO 17
<211> LENGTH: 840
<212> TYPE: DNA
<213> ORGANISM: Borrelia burgdorferi

<400> SEQUENCE: 17

| | | | | | |
|---|---|---|---|---|---|
| gtactcgttg | ctgccgcgcg | cgccaccaga | cataatagct | gacagactaa | cagactgttc | 60 |
| catgagcaac | gacggcgcgc | gcggtggtct | gtattatcga | ctgtctgatt | gtctgacaag | 120 |
| ctttccatgg | gtcttttctg | cagtcaccgt | cgtcgaccag | agctgagatc | ctacaggagt | 180 |
| gaaaggtacc | cagaaaagac | gtcagtggca | gcagctggtc | tcgactctag | gatgtcctca | 240 |
| ccagggctgg | agagaaaacc | tctgcgagga | aagggaagga | gcaagccgtg | aatttaaggg | 300 |
| ggtcccgacc | tctctttttgg | agacgctcct | ttcccttcct | cgttcggcac | ttaaattccc | 360 |
| acgctgtgaa | gcaatcatgg | atgcaatgaa | gagagggctc | tgctgtgtgc | tgctgctgtg | 420 |
| tgcgacactt | cgttagtacc | tacgttactt | ctctcccgag | acgacacacg | acgacgacac | 480 |
| tggagcagtc | ttcgtttcgc | ccagcggtac | ctgtgcacaa | aaaggtgctg | agtcaattgg | 540 |
| acctcgtcag | aagcaaagcg | ggtcgccatg | gacacgtgtt | tttccacgac | tcagttaacc | 600 |
| ttctcaaaaa | gaaatgatc | taaaccttga | agactctagt | aaaaaatcac | atcaaaacgc | 660 |
| aagagttttt | ctttttactag | atttggaact | tctgagatca | ttttttagtg | tagttttgcg | 720 |
| taaacaagac | cttcctgcgg | tgacagaaga | ctcagtgtct | ttgtttaatg | gtaataaaat | 780 |
| atttgttctg | gaaggacgcc | actgtcttct | gagtcacaga | aacaaattac | cattattta | 840 |

<210> SEQ ID NO 18
<211> LENGTH: 569
<212> TYPE: PRT
<213> ORGANISM: Borrelia burgdorferi -continued

<400> SEQUENCE: 18

```
Met Lys Lys Tyr Leu Gly Ile Gly Leu Ile Leu Ala Leu Ile Ala
 1               5                  10                  15

Cys Lys Gln Asn Val Ser Ser Leu Asp Glu Lys Asn Ser Val Ser Val
                20                  25                  30

Asp Leu Pro Gly Glu Met Lys Val Leu Val Ser Lys Glu Lys Asn Lys
            35                  40                  45

Asp Gly Lys Tyr Asp Leu Ile Ala Thr Val Asp Lys Leu Glu Leu Lys
        50                  55                  60

Gly Thr Ser Asp Lys Asn Asn Gly Ser Gly Val Leu Glu Gly Val Lys
 65                 70                  75                  80

Ala Asp Lys Ser Lys Val Lys Leu Thr Ile Ser Asp Asp Leu Gly Gln
                85                  90                  95

Thr Thr Leu Glu Val Phe Lys Glu Asp Gly Lys Thr Leu Val Ser Lys
            100                 105                 110

Lys Val Thr Ser Lys Asp Lys Ser Ser Thr Glu Glu Lys Phe Asn Glu
        115                 120                 125

Lys Gly Glu Val Ser Glu Lys Ile Ile Thr Arg Ala Asp Gly Thr Arg
130                 135                 140

Leu Glu Tyr Thr Gly Ile Lys Ser Asp Gly Ser Gly Lys Ala Lys Glu
145                 150                 155                 160

Val Leu Lys Gly Tyr Val Leu Glu Gly Thr Leu Thr Ala Glu Lys Thr
                165                 170                 175

Thr Leu Val Val Lys Glu Gly Thr Val Thr Leu Ser Lys Asn Ile Ser
            180                 185                 190

Lys Ser Gly Glu Val Ser Val Glu Leu Asn Asp Thr Asp Ser Ser Ala
        195                 200                 205

Ala Thr Lys Lys Thr Ala Ala Trp Asn Ser Gly Thr Ser Thr Leu Thr
210                 215                 220

Ile Thr Val Asn Ser Lys Lys Thr Lys Asp Leu Val Phe Thr Lys Glu
225                 230                 235                 240

Asn Thr Ile Thr Val Gln Gln Tyr Asp Ser Asn Gly Thr Lys Leu Glu
                245                 250                 255

Gly Ser Ala Val Glu Ile Thr Lys Leu Asp Glu Ile Lys Asn Ala Leu
            260                 265                 270

Lys Met Arg Leu Leu Ile Gly Phe Ala Leu Ala Leu Ala Leu Ile Gly
        275                 280                 285

Cys Ala Gln Lys Gly Ala Glu Ser Ile Gly Ser Gln Lys Glu Asn Asp
290                 295                 300

Leu Asn Leu Glu Asp Ser Ser Lys Lys Ser His Gln Asn Ala Lys Gln
305                 310                 315                 320

Asp Leu Pro Ala Val Thr Glu Asp Ser Val Ser Leu Phe Asn Gly Asn
                325                 330                 335

Lys Ile Phe Val Ser Lys Glu Lys Asn Ser Ser Gly Lys Tyr Asp Leu
            340                 345                 350

Arg Ala Thr Ile Asp Gln Val Glu Leu Lys Gly Thr Ser Asp Lys Asn
        355                 360                 365

Asn Gly Ser Gly Thr Leu Glu Gly Ser Lys Pro Asp Lys Ser Lys Val
370                 375                 380

Lys Leu Thr Val Ser Ala Asp Leu Asn Thr Val Thr Leu Glu Ala Phe
385                 390                 395                 400

Asp Ala Ser Asn Gln Lys Ile Ser Ser Lys Val Thr Lys Lys Gln Gly
                405                 410                 415
```

-continued

```
Ser Ile Thr Glu Glu Thr Leu Lys Ala Asn Lys Leu Asp Ser Lys Lys
            420                 425                 430

Leu Thr Arg Ser Asn Gly Thr Thr Leu Glu Tyr Ser Gln Ile Thr Asp
        435                 440                 445

Ala Asp Asn Ala Thr Lys Ala Val Glu Thr Leu Lys Asn Ser Ile Lys
    450                 455                 460

Leu Glu Gly Ser Leu Val Val Gly Lys Thr Thr Val Glu Ile Lys Glu
465                 470                 475                 480

Gly Thr Val Thr Leu Lys Arg Glu Ile Glu Lys Asp Gly Lys Val Lys
                485                 490                 495

Val Phe Leu Asn Asp Thr Ala Gly Ser Asn Lys Lys Thr Gly Lys Trp
            500                 505                 510

Glu Asp Ser Thr Ser Thr Leu Thr Ile Ser Ala Asp Ser Lys Lys Thr
        515                 520                 525

Lys Asp Leu Val Phe Leu Thr Asp Gly Thr Ile Thr Val Gln Gln Tyr
    530                 535                 540

Asn Thr Ala Gly Thr Ser Leu Glu Gly Ser Ala Ser Glu Ile Lys Asn
545                 550                 555                 560

Leu Ser Glu Leu Lys Asn Ala Leu Lys
                565
```

COMPOSITIONS AND METHODS FOR ADMINISTERING BORRELIA DNA

RELATED APPLICATIONS

This application is a continuation-in-part of allowed application Ser. No. 08/663,998, filed Jun. 14, 1996, now U.S. Pat. No. 5,846,946, incorporated herein by reference.

Reference is made to U.S. or PCT applications Ser. No. 08/320,416, filed Oct. 3, 1994 (allowed, now U.S. Pat. No. 5,582,990), Ser. No. 08/137,175, filed Oct. 26, 1993 (allowed, now U.S. Pat. No. 5,777,095), Ser. No. 08/262,220, filed Jun. 20, 1994, PCT/US95/07665, Ser. No. 08/373,455, filed Jan. 17, 1995, Ser. No. 08/373,993, filed Jan. 20, 1995 (allowed, now U.S. Pat. No. 5,688,512), PCT/US92/08697, WO 90/04411, Ser. No. 08/470,672, filed Jun. 6, 1995 and Ser. No. 08/479,017 filed Jun. 6, 1995, each of which (including any patents issued therefrom) is hereby incorporated herein by reference.

Several documents are cited in this application, with full citation thereof where cited, or in the listing headed "References" before the claims; and, each document cited herein, as well as all documents cited in documents cited herein, are hereby incorporated herein by reference.

STATEMENT OF GOVERNMENT SUPPORT

Some work in this application may have been supported by NIH grant RO1 37248, and, without any admission or prejudice to asserting otherwise, the U.S. Government may have certain rights.

FIELD OF THE INVENTION

This invention relates to compositions and methods for administering Borrelia genospecies DNA encoding antigen (s) in vivo or in vitro. More particularly, this invention relates to compositions and methods for administering Borrelia genospecies DNA encoding an antigen or antigens, e.g., OspA (outer surface protein A) and/or OspB (outer surface protein B), and/or OspC (outer surface protein C), or fragments thereof such as fragments thereof containing at least one epitope of interest, for expression thereof, in vivo, ex vivo or in vitro.

BACKGROUND OF THE INVENTION

Lyme disease is a multisystem illness, transmitted by ticks of the *Ixodes ricinus* complex. The spirochaete *Borrelia burgdorferi* sensu lato is the etiologic agent of Lyme disease, which is now the most common arthropod borne disease in the United States, and is endemic in Central Europe (Barbour and Fish 1993). More particularly, there are three genospecies of Borrelia associated with Lyme disease: *Borrelia burgdorferi*, *Borrelia afzelii* and *Borrelia garinii*. *Borrelia burgdorferi* is the etiologic agent of Lyme disease in North America, and some European Lyme disease is considered to be *Borrelia burgdorferi* sensu stricto. *Borrelia afzelii* and *Borrelia garinii* are the major cause of European Lyme disease and are considered *Borrelia burgdorferi* sensu lato.

Although Lyme disease is curable by antibiotic therapy in its early stages, if Lyme disease is allowed to progress, cardiac, neurological and joint abnormalities can arise. Investigations into the development of a human vaccine for Lyme disease are under way. The outer surface lipoprotein OspA of *Borrelia burgdorferi* is the current major candidate molecule for development of such a vaccine.

Recombinant OspA lipoprotein (rOspA) is known to elicit a protective immune response in mice against challenge by infectious *B. burgdorferi* (Fikrig et al., 1990; Erdile et al., 1993; U.S. Ser. No. 08/373,455). OspA is currently undergoing human field trials as a subcutaneously administered vaccine in the United States (Keller et al., 1994). Above-cited U.S. Pat. No. 5,688,512 relates to substantially pure OspA, vaccines including substantially pure OspA, and methods for inducing a protective immunological response against *B. burgdorferi* employing such vaccines, inter alia.

Above-cited applications Ser. No. 08/373,455 and PCT/US92/08697 relate to rOspA vaccines, especially lipidated rospA, and methods for expressing DNA encoding OspA. Above-cited applications Ser. No. 08/320,416 (now U.S. Pat. No. 5,582,990) and WO 90/04411 relate to DNA encoding OspA, the amino acid sequence of OspA, synthetic OspA, compositions containing OspA or synthetic OspA, and methods of using such compositions. Above cited application Ser. No. 08/137,175, filed Oct. 26, 1993 (now U.S. Pat. No. 5,777,095) relates to DNA coding for various OspAs and OspBs, OspAs and OspBs encoded by such DNA (including amino acid sequences therefor), and immunologically interesting fragments of OspAs and OspBs and DNA coding therefor.

In approximately half of the European isolates of *B. burgdorferi*, outer surface protein C (OspC) is the major surface antigen found on these spirochetes. Immunization of gerbils and mice with purified recombinant OspC produces protective immunity to *B. burgdorferi* strains expressing the homologous OspC protein (Preac-Mursic et al., INFECTION (1992) 20:342–349; Probert et al., INFECTION AND IMMUNITY (1994) 62:1920–1926). Published international patent application WO 91/09870 (Mikrogen Molekularbiologische Entwicklungs-GmbH) describes the DNA sequence of the ospC gene of *B. burgdorferi* strain Pko and the OspC protein encoded thereby of 22 kDa molecular weight (termed "pC" therein). This sequence reveals that OspC is a lipoprotein that employs a signal sequence similar to that used for OspA. As to DNA encoding OspC or recombinant OspC, reference is also made to WO96/05313 (Max-Planck Institute); Leuba-Garcia et al., Zentralbl Bakteriol. 287(4):475–84, 1998; Rauer et al., J. Clin. Microbiol. 36(4):857–61, 1998; Masuzawa et al., Clin. Diagn. Lab. Immunol. 4(1):60–63, 1997; Fukunaga et al. J. Clin. Microbiol. 33(9):2415–2420, 1995; Jauris-Heipke et al., J. Clin. Microbiol. 33(7):1860–66, 1995; Theisen et al., J. Bacteriol. 177(11):3036–3044, 1995; Stevenson et al. FEMS Microbiol. Lett. 124(3):367–72, 1994; and Padula et al., Infect. Immun. 61(12):5097–5105, 1993.

The other above-cited applications relate to DNA encoding other Borrelia antigens or other Osps, or to DNA encoding useful fragments of OspA or of other Osps, amino acid sequences thereof, compositions containing such fragments or other Osps, and methods for using such compositions; and, such DNA that can be used in the methods of Ser. No. 08/373,455 or PCT/US92/08697 to produce OspA, other Borrelia antigens or outer surface proteins (Osps), or fragments thereof, can be used in this invention. In regard to DNA useful in this invention, reference again made to V. Preac-Mursic et al., supra, W. S. Probert et al., supra, WO 91/09870, supra, as well as to all of the documents cited herein and also to Molecular Microbiology (1989), 3(4), 479–486, and PCT publications WO 93/04175, and WO 96/06165.

Alternative vaccination strategies are desirable as such provide alternative routes to administration or alternative routes to responses.

In particular, it is believed that heretofore the art has not taught or suggested administration to a eukaryotic cell in vitro or ex vivo, or to a mammalian host—domesticated or wild or human—susceptible to Lyme disease, of Borrelia genospecies DNA e.g., DNA encoding OspA and/or OspB, and/or OspC or expression thereof in vivo, especially as herein disclosed.

OBJECTS AND SUMMARY OF THE INVENTION

It is an object of the invention to provide methods and compositions for administering to a host, such as a mammalian host susceptible to Lyme Disease, Borrelia genospecies isolated and/or purified DNA encoding an antigen or antigens or a fragment or fragments thereof such as fragment or fragments containing at least one epitope of interest, e.g., isolated and/or purified DNA encoding an antigen or antigens or a fragment or fragments thereof such as fragment or fragments containing at least one epitope of interest from *Borrelia burgdorferi, Borrelia afzelii, Borrelia garinii* or combinations thereof, such as isolated and/or purified DNA encoding OspA, and/or OspB and/or OspC, or isolated and/or purified DNA encoding at least one epitope of OspA and/or OspB and/or OspC; for instance, DNA encoding *Borrelia burgdorferi* OspA and/or OspB and/or OspC. The compositions can include a carrier or diluent. The DNA is administered in a form to be expressed by the host, and preferably in an amount sufficient to induce a response such as a protective immune response; and, the DNA can be administered without any necessity of adding any immunogenicity-enhancing adjuvant.

Accordingly, the present invention provides Borrelia genospecies antigen or epitope DNA plasmids for expression by eukaryotic cells, compositions containing the plasmids, and methods for using the compositions and for using the products from the compositions.

The plasmid of the invention can comprise from upstream to downstream (5' to 3'): DNA encoding a promoter for driving expression in eukaryotic cells, DNA encoding a leader peptide for enabling secretion of a prokaryotic protein sequence from a mammalian cell, Borrelia genospecies antigen or epitope DNA, and DNA encoding a terminator.

The DNA encoding a promoter for driving expression in eukaryotic cells can be a eukaryotic, e.g., mammalian, viral promoter, such as a herpes virus promoter. A human cytomegalovirus promoter is presently preferred. The human cytomegalovirus promoter can be an immediate early human cytomegalovirus promoter such as HCMV-IE. The plasmid can contain the HCMV-IE gene 5' untranslated region (UTR) which includes Intron A. This sequence can be 3' to the HCMV-IE promoter and 5' to the portion of the chimeric 5' UTR sequence and leader peptide (the UTR and leader peptide coding sequence can be derived from the DNA encoding the human tissue plasminogen activator, as discussed below).

The DNA encoding a leader peptide is for facilitating secretion of a prokaryotic protein sequence from a mammalian cell. This DNA can be any DNA encoding a suitable or similar leader peptide for the purpose of secretion from a mammalian cell, e.g., DNA encoding a eukaryotic leader peptide. For instance, the DNA encoding a leader peptide can be from DNA encoding a peptide hormone, i.e., a peptide hormone leader peptide, such as from a mammal, e.g., a human peptide hormone leader peptide. Specific examples of DNA encoding leader peptides suitable use in the invention include the DNA encoding the leader peptide of insulin (human, bovine, porcine, etc.), renin, Factor VIII, and tissue plasminogen activator.

DNA encoding human tissue plasminogen activator (TPA) leader is presently preferred. The DNA encoding TPA is derived from the TPA gene and encodes a portion of the 5' UTR and leader peptide from the gene. TPA DNA having a portion of the 5' UTR and leader peptide can even increase eukaryotic cell expression. Without wishing to necessarily be bound by any one particular theory, increased expression can be due to the 5' UTR.

The Borrelia genospecies antigen or epitope DNA is preferably without the natural leader sequence. The Borrelia genospecies antigen or epitope DNA can preferably encode at least one antigen selected from OspA, OspB, OspC, OspD, other Osps, and other antigens (see documents cited herein). Similarly, the Borrelia genospecies antigen or epitope DNA can preferably encode at least one epitope of interest from an antigen selected from OspA, OspB, OspC, OspD, other osps, and other antigens. DNA without the natural leader sequence encoding OspA and/or OspB and/or OspC and/or an epitope of interest from OspA and/or OspB and/or OspC is presently preferred. The DNA can be from *Borrelia burgdorferi, Borrelia afzelii, Borrelia garinii* or from any combination thereof; with *Borrelia burdorferi* presently preferred.

The terminator can be any suitable terminator sequence for use in eukaryotic cells; for instance, a terminator sequence from a mammalian peptide hormone. The Bovine Growth Hormone (BGH) terminator is presently preferred.

The plasmid of the invention can contain genes for a fusion protein of the activator (e.g., TPA) and the Borrelia antigen (e.g., OspA, OspB, OspC) or at least an epitope thereof.

The invention comprehends compositions comprising the plasmid and a carrier. The carrier can be any suitable carrier which does not disrupt the DNA or the function of the plasmid. Saline is a presently preferred carrier.

The invention further comprehends methods of using the compositions, e.g., administering the composition to a host susceptible to Lyme disease to elicit a response or express an antigen. The response can be protective. The response can be simply an antibody response, and the method can further include recovering antibodies and/or antibody-producing cells (with the cells further useful for producing hybridoma cells and monoclonal antibodies, e.g., by fusing the antibody-producing cells to produce hybridoma cells, and then obtaining monoclonal antibodies from expression by the hybridoma cells). The host can be a mammal, such as a human.

Still further, the invention provides methods for expressing an antigen or epitope or preparing an antigen or epitope in vitro comprising transfecting eukaryotic cells with an inventive plasmid. The method can further comprise recovering the antigen or epitope from the cells.

Methods for preparing the plasmid by ligating the respective pieces of DNA (DNA molecules) from which it is comprised, and methods for using the antibodies and antigens or epitopes, as well as the antigens or epitopes and antibodies themselves, are contemplated by the present invention.

Other objects and embodiments are disclosed or are obvious from the following Detailed Description.

BRIEF DESCRIPTION OF DRAWINGS

In the following Detailed Description, reference is made to the accompanying Figures, incorporated herein by reference, wherein:

FIG. 1 shows a diagram of VR2210 with a few characteristic restriction sites;

Figure 2B:
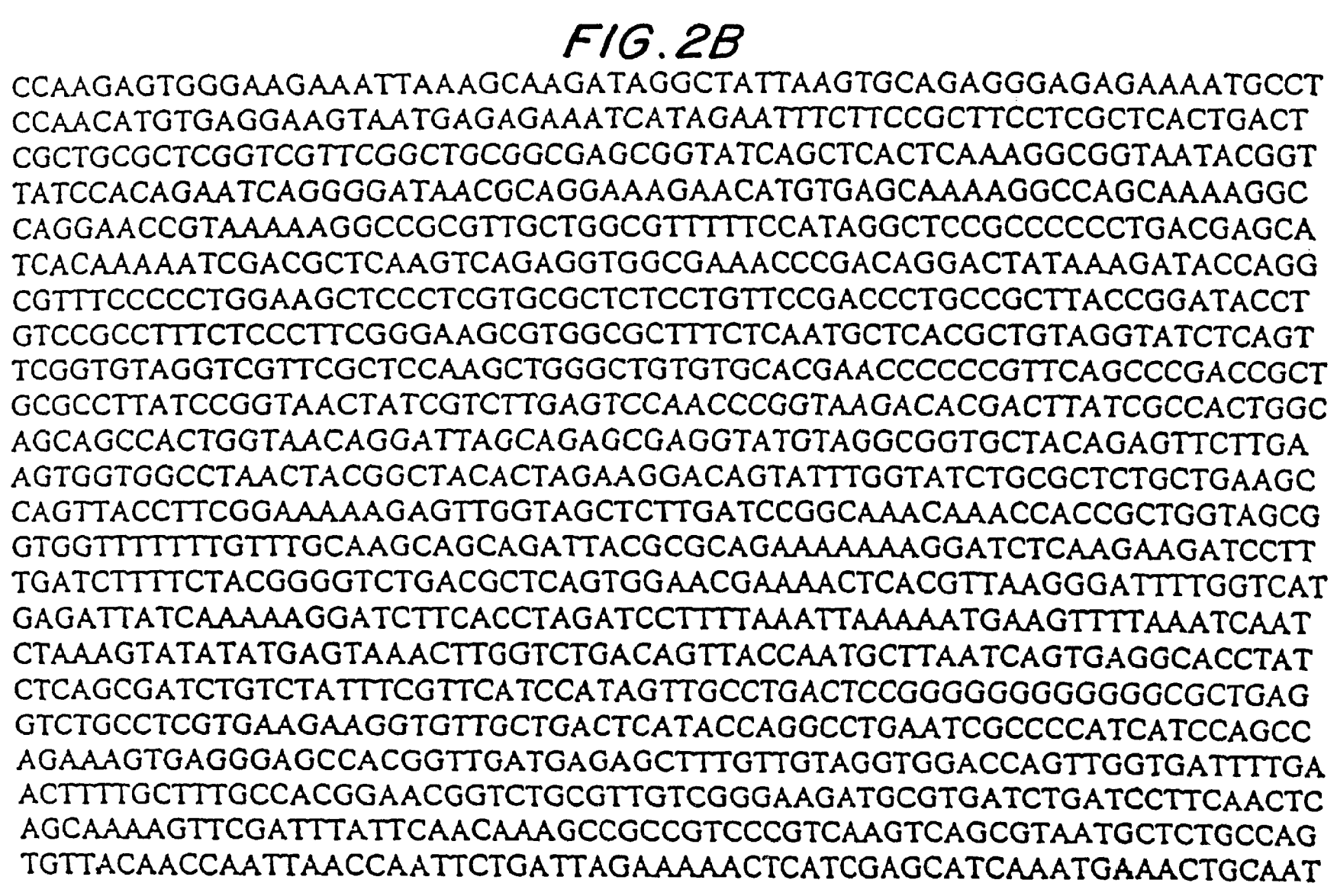

FIGS. 2A, 2B, 2C, and 2D show the nucleotide sequence of VR2210 (SEQ ID NO:1) with the location of primer, used to amplify and insert the OspA coding sequence, underlined and overlined;

FIG. 3 shows a diagram of VR2211 with a few characteristic restriction sites;

FIGS. 4A, 4B, 4C and 4D show the nucleotide sequence of VR2211 (SEQ ID NO:2) with the location of primer, used to amplify and insert the OspB coding sequence, underlined and overlined;

FIGS. 5A, 5B, and 5C show the nucleotide sequence of OspA (TRH43; *B. burgdorferi* strain 31) (SEQ ID NO:3);

FIGS. 6A, 6B, and 6C show the nucleotide sequence of OspB (TRH46; *B. burgdorferi strain* B31) (SEQ ID NO:4);

FIGS. 7A, 7B, 7C, 7D, 7E, 7F, 7G, and 7H show a nucleotide sequence of ospA and ospB (SEQ ID NO:5) and a predicted amino acid sequence therefor (SEQ ID NO:18);

FIG. 9 shows the multiple cloning site sequence of VR1012 from nucleotides 1841 to 2001 (SEQ ID NO:6);

FIGS. 10A and 10B show the nucleotide sequence of VR1012 (SEQ ID NO:7);

FIGS. 11A and 11B show the nucleotide sequence of nkCMVintBL (SEQ ID NO:8);

FIG. 12 shows the nucleotide sequence of the nkCMVintBL cloning site with the TPA signal peptide sequence (SEQ ID NO:9);

FIG. 13 shows PCR primers for amplifying ospA (SEQ ID NO:10, 11);

FIG. 14 shows PCR primers for amplifying ospB (SEQ ID NO:12, 13);

FIG. 15 shows a partial nucleotide sequence of VR2210 (SEQ ID NO:16);

FIG. 16 shows a partial nucleotide sequence of VR2211 (SEQ ID NO:17);

FIG. 21 shows the nucleotide sequence of VR2212 (SEQ ID NO:19) (5626 bps DNA circular; B31 ospC with human TPA leader sequence; the region of bps 1–1621 is named CMVprom/enh/int" which is CMVpromoter/enhancer/intron; the gene of bps 1631–1804 is named TPA signal which is 5' UT and TPA signal; the gene of bps 1805–2390 is named B31 without its endogenous leader peptide ospC which is coding for the outer surface protein C from *B. burgdorferi* B31; the region of bps 2397–2944 is named BGH term. and is the BGH terminator; the gene of bps 5077–4262 is named Kan and is coding for Kanamycin resistance (as a selectable marker));

FIG. 23 shows the nucleotide sequence of VR2214 (SEQ ID NO:20) (5632 bps DNA circular; Pko ospC with human TPA leader sequence; the region of bps 1–1621 is named CMVprom/enh/int" which is CMVpromoter/enhancer/intron; the gene of bps 1631–1804 is named TPA signal which is 5' UT and TPA signal and 5' UT; the gene of bps 180–2396 is named PkoospC which is coding for the outer surface protein C from *B. burgdorferi* Pko with out its leader peptide; the region of bps 2403–2950 is named BGH term. and is the BGH terminator; the gene of bps 5083–4268 is named Kan and is coding for Kanamycin resistance [as a selectable marker]);

FIG. 26 shows the nucleotide sequence of VR1027 (SEQ ID NO:23) (5046 bps circular DNA); and FIG. 27 shows a graph of ELISA GMT vs. days for Group 1 (diamonds: C3H/He mice that received B31 ospC DNA in plasmid form, i.e., VR2212), Group 2 (squares: ICR mice that received B31 ospC DNA in plasmid form, i.e., VR2212), Group 3 (triangles: C3H/He mice that received Pko ospC DNA in plasmid form, i.e., VR2214), and Group 4 (X's: ICR mice that received Pko ospC DNA in plasmid form, i.e., VR2214).

DETAILED DESCRIPTION

Direct injection of plasmid DNA has become a simple and effective method of vaccination against a variety of infectious diseases (see, e.g., Science, 259:1745–49, 1993; U.S. Pat. Nos. 5,703,055, 5,693,622, 5,589,466 and 5,580,859; Robinson et al., seminars in IMMUNOLOGY, 9:271–83, 1997; Luke et al., J. Infect. Dis., 175(1):91–97, 1997; Norman et al., Vaccine, 15(8):801–803, 1997; (Bourne al., The Journal of Infectious Disease, 173:800–7, 1996;) as well as allowed U.S. application Ser. No. 08/663,998; each of which, and the documents cited therein, are hereby incorporated herein by reference). It is potentially more potent and longer lasting than recombinant protein vaccination because it elicits both a humoral as well as a cellular immune response.

The present invention provides a DNA-based vaccine or immunological composition against Lyme disease (e.g., *Borrelia burgdorferi, afzelii*, or *garinii*) and can elicit an immunological response, which can confer protection, even up to 100%, in mice against challenge with an infectious strain of *Borrelia burgdorferi*. Exemplary plasmids of the invention contain the human cytomegalovirus immediate early promoter driving expression of the B31 outer surface protein A (OspA), or outer surface protein B (OspB), or outer surface protein C (OspC). To facilitate expression in eukaryotic cells, the natural leader sequence of the gene encoding these Osps, e.g., OspA, OspB, OspC has been replaced with the human tissue plasminogen activator leader sequence.

Figure 17:
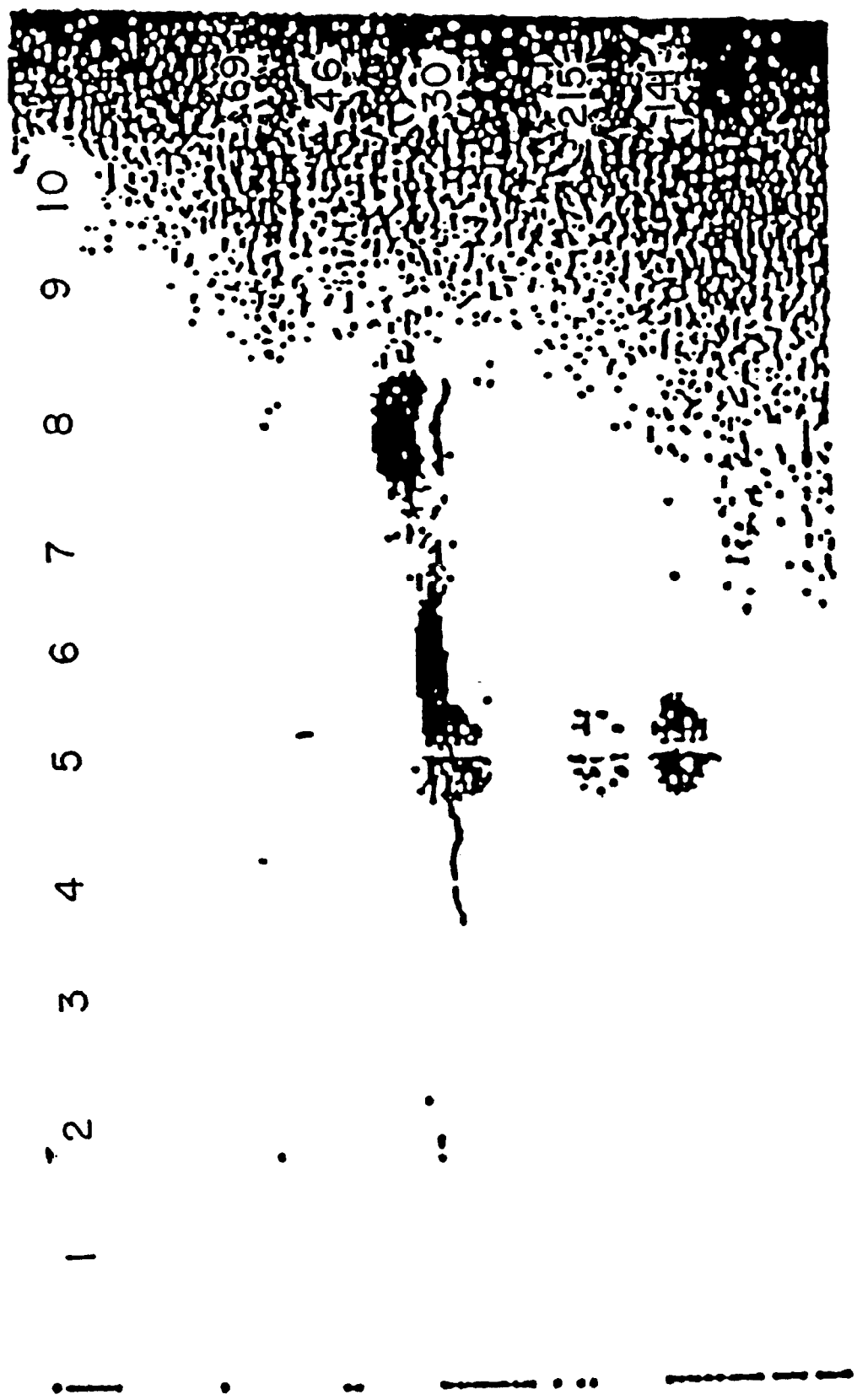
FIGS. 17, 18A and 18B show immunoblots.
Figure 18B:
Figure 18A:

Expression and secretion was demonstrated in transiently transfected UM449 and BHK cells by Western blot (See, e.g., FIGS. 17, 18A, 18B).

Protection was demonstrated in C3H/HeN by injecting, intramuscularly, naked plasmid DNA and subsequently challenging with Sh2 spirochetes. Sera taken following vaccination contained high titers of antibody to OspA which inhibited spirochete growth in vitro. Immunized animals showed no sign of Lyme disease at 14 days after challenge. Moreover, all tissues examined were completely free of spirochetes.

Thus, a DNA vaccine or immunological composition, expressing a Borrelia antigen or epitope of interest, for instance a *Borrelia burgdorferi, Borrelia afzelii, Borrelia garinii* antigen or epitope of interest or combinations thereof, e.g., OspA, OspB, OspC protein or epitopes therefrom or any combination thereof, can protect mice against infection by a Borrelia genospecies, the etiologic agent of Lyme disease. The composition is thus useful for eliciting a protective response in a host susceptible to Lyme Disease, as well as for eliciting antigens, epitopes, and antibodies, which also are useful in and of themselves.

Therefore, as discussed above, the invention in a general sense preferably provides methods for immunizing, or vaccinating, or eliciting an immunological response in a host, such as a host susceptible to Lyme disease, e.g., a mammalian host, against Borrelia and accordingly Lyme Disease, by administering DNA encoding a Borrelia antigen or epitope, for instance DNA encoding a *Borrelia burgdorferi, Borrelia afzelii, Borrelia garinii* antigen or epitope of interest or combinations thereof, e.g., OspA and/or OspB, and/or OspC, preferably OspA, in a suitable carrier or diluent, such as saline; and, the invention provides plasmids and compositions for performing the method, as well as methods for making the plasmids, and uses for the expression products of the plasmids, as well as for antibodies elicited thereby.

From present dog and human trials based on efficacy studies with mice (Erdile et al., 1993; U.S. Ser. No. 08/373,455), it is clear that mice are now a suitable animal model with respect to Borrelia and Lyme disease for extrapolation to domestic animals, humans, and other animals susceptible to Lyme disease or Borrelia infection (e.g., wild animals such as deer).

In view of the broad nature of the invention, i.e., that the invention is applicable to Borrelia genospecies other than burgdorferi (i.e., the invention is also applicable to genospecies *afzelii* and *garinii*, and broadly to any Borrelia genospecies antigen or antigens or epitope or epitopes or immunologically active fragments of antigen or antigens), discussion herein directed to OspA is intended toward the broad nature of the invention, i.e., "OspA" is exemplary and can be read in this specification to include any Borrelia genospecies antigen or an immunological fragment thereof, including without limitation, OspA, OspB, OspC and epitopes or immunologically active fragments thereof.

In the present invention, the DNA encoding OspA, or broadly, the Borrelia genospecies antigen or epitope or immunologically active fragment thereof, can be administered in dosages and by techniques well known to those skilled in the medical or veterinary arts taking into consideration such factors as the age, sex, weight, species and condition of the particular patient, and the route of administration. DNA encoding OspA, or broadly the Borrelia genospecies antigen or epitope or immunologically active fragment thereof, can be administered alone, or can be co-administered or sequentially administered with other Borrelia antigens or epitopes, or with DNA encoding other Borrelia genospecies antigens or epitopes; and, the DNA encoding OspA or broadly the Borrelia genospecies antigen or epitope or immunologically active fragment thereof, can be sequentially administered, e.g., each Spring as the "Lyme Disease season" is about to begin.

As broadly discussed above, the invention comprehends plasmids comprising DNA including Borrelia genospecies antigen or epitope DNA for expression by eukaryotic cells. The DNA, from upstream to downstream (5' to 3'), can comprise: DNA encoding a promoter for driving expression in eukaryotic cells, DNA encoding a leader peptide which enables secretion of a prokaryotic protein sequence from a mammalian cell, DNA encoding a Borrelia genospecies antigen (or antigens or epitope or epitopes), and DNA encoding a terminator.

For instance, the promoter can be a eukaryotic viral promoter such as a herpes virus promoter, e.g., human cytomegalovirus promoter DNA.

The DNA encoding a leader peptide which enables secretion of a prokaryotic protein sequence from a mammalian cell is any DNA encoding any suitable leader for this purpose such as DNA encoding a eukaryotic, preferably mammalian, leader sequence; for instance, DNA encoding a leader peptide of a peptide hormone, or, for example, of insulin, renin, Factor VIII, TPA, and the like, with DNA encoding human tissue plasminogen activator (TPA) leader peptide presently preferred.

The human cytomegalovirus promoter can be an immediate early human cytomegalovirus promoter such as HCMV-IE. As to HCMV promoter, reference is made to U.S. Pat. Nos. 5,168,062 and 5,385,839. The plasmid of the invention can contain the HCMV-IE gene 5' untranslated region (UTR) which includes Intron A. This sequence can be 3' to the HCMV-IE promoter and 5' to the activator portion of the 5' UTR sequence and leader peptide.

The TPA sequence can be derived from the TPA gene and can encode a portion of the 5' UTR and leader peptide from that gene. The 5' UTR of TPA may increase eukaryotic cell expression.

The Borrelia genospecies DNA can be from *B. burgdorferi, afzelii, garinii* or combinations thereof, e.g., *B. burgdorferi*; and, can encode an antigen such as OspA, OspB, OspC, OspD, other outer surface proteins or an epitope or epitopes therefrom or a combination of antigens, e.g., OspA and/or OspB and/or OspC; preferably without the natural leader sequence.

The transcriptional terminator sequence can be any suitable terminator, such as a eukaryotic terminator, for instance, DNA encoding a terminator for a mammalian peptide, with the BGH terminator presently preferred.

The plasmid can be in admixture with any suitable carrier, diluent or excipient such as sterile water, physiological saline, and the like. Of course, the carrier, diluent or excipient should not disrupt or damage the plasmid DNA.

The plasmid can be administered in any suitable manner. The plasmid can be in a composition suitable for the manner of administration. The compositions can include: liquid preparations for orifice, e.g., oral, nasal, anal, vaginal, peroral, intragastric administration and the like, such as solutions, suspensions, syrups, elixirs; and liquid preparations for parenteral, subcutaneous, intradermal, intramuscular, intravenous administration, and the like, such as sterile solutions, suspensions or emulsions, e.g., for administration by injection. Intramuscular administration and compositions therefor are presently preferred.

The plasmids of the invention can be used for in vitro expression of antigens by eukaryotic cells. Recovery of such antigens can be by any suitable techniques; for instance, techniques analogous to the recovery techniques employed in the documents cited herein (such as the applications cited under Related Applications and the documents cited therein).

The thus expressed antigens or epitopes can be used in immunological, antigenic or vaccine compositions, with or without an immunogenicity-enhancing adjuvant ("expressed antigen compositions"). Such compositions can be administered in dosages and by techniques well known to those skilled in the medical or veterinary arts taking into consideration such factors as age, sex, weight, species, condition of the particular patient, and the route of administration. These compositions can be administered alone or with other compositions, and can be sequentially administered, e.g., each Spring as the "Lyme Disease season" is about to begin.

The route of administration for the expressed antigen compositions can be oral, nasal, anal, vaginal, peroral, intragastric, parenteral, subcutaneous, intradermal, intramuscular, intravenous, and the like.

The expressed antigen compositions can be solutions, suspensions, emulsions, syrups, elixirs, capsules (including "gelcaps"—gelatin capsule containing a liquid antigen or fragment thereof preparation), tablets, hard-candy-like preparations, and the like. The expressed antigen compositions may contain a suitable carrier, diluent, or excipient such as sterile water, physiological saline, glucose or the like. The compositions can also be lyophilized. The compositions can contain auxiliary substances such as wetting or emulsifying agents, pH buffering agents, adjuvants, gelling or viscosity enhancing additives, preservatives, flavoring agents, colors, and the like, depending upon the route of administration and the preparation desired. Standard texts, such as "REMINGTON'S PHARMACEUTICAL SCIENCE", 17th edition, 1985, incorporated herein by reference, may be consulted to prepare suitable preparations, without undue experimentation.

Suitable dosages for plasmid compositions and for expressed antigen compositions can also be based upon the examples below, and upon the documents herein cited. For example, suitable dosages can be 0.5–500 µg antigen, preferably 0.5 to 50 µg antigen, for instance, 1–10 µg antigen in expressed antigen compositions. In plasmid compositions, the dosage should be a sufficient amount of plasmid to elicit a response analogous to the expressed antigen compositions; or expression analogous to dosages in expressed antigen compositions. For instance, suitable quantities of plasmid DNA in plasmid compositions can be 0.1 µg to 2 mg, preferably 1–10 µg. Dosages can also be varied by one skilled in the art, depending on typical factors, such as the age, sex, weight, general health, and species of the patient, without undue experimentation.

Thus, in a broad sense, the invention further provides a method comprising administering a composition containing plasmid DNA including DNA encoding a Borrelia genospecies antigen or antigens or epitope or epitopes: for expression of the antigen or antigens or epitope or epitopes in vivo for eliciting an immunological, antigenic or vaccine (protective) response by a eukaryotic cell; or, for ex vivo or in vitro expression (That is, the cell can be a cell of a host susceptible to Lyme Disease, i.e., the administering can be to a host susceptible to Lyme Disease such as a mammal, e.g., a human; or, the cell can be an ex vivo or in vitro cell). The invention further provides a composition containing a Borrelia genospecies antigen or antigens or epitope or epitopes from expression of the plasmid DNA by a eukaryotic cell, in vitro or ex vivo, and methods for administering such compositions to a host mammal susceptible to Lyme disease to elicit a response.

Since the methods can stimulate an immune or immunological response, the inventive methods can be used for merely stimulating an immune response (as opposed to also being a protective response) because the resultant antibodies (without protection) are nonetheless useful. From eliciting antibodies, by techniques well-known in the art, monoclonal antibodies can be prepared and, those monoclonal antibodies, can be employed in well known antibody binding assays, diagnostic kits or tests to determine the presence or absence of a Borrelia genospecies or to determine whether an immune response to the bacteria has simply been stimulated. Those monoclonal antibodies can also be employed in recovery or testing procedures, for instance, in immunoadsorption chromatography to recover or isolate a Borrelia genospecies antigen such as OspA, OspB, or OspC or epitope therefrom.

Monoclonal antibodies are immunoglobulins produced by hybridoma cells. A monoclonal antibody reacts with a single antigenic determinant and provides greater specificity than a conventional, serum-derived antibody. Furthermore, screening a large number of monoclonal antibodies makes it possible to select an individual antibody with desired specificity, avidity and isotype. Hybridoma cell lines provide a constant, inexpensive source of chemically identical antibodies and preparations of such antibodies can be easily standardized. Methods for producing monoclonal antibodies are well known to those of ordinary skill in the art, e.g., Koprowski, H. et al., U.S. Pat. No. 4,196,265, issued Apr. 1, 1989, incorporated herein by reference.

Uses of monoclonal antibodies are known. One such use is in diagnostic methods, e.g., David, G. and Greene, H. U.S. Pat. No. 4,376,110, issued Mar. 8, 1983; incorporated herein by reference. Monoclonal antibodies have also been used to recover materials by immunoadsorption chromatography, e.g., Milstein, C. 1980, Scientific American 243:66, 70, incorporated herein by reference.

Returning now to the preparation of the inventive plasmids, the DNA therein is preferably ligated together to form a plasmid. For instance, the promoter, leader sequence, antigen and terminator DNA is preferably isolated, purified and ligated together in a 5' to 3' upstream to downstream orientation. A three-way ligation, or a two-way ligation, as exemplified below, is presently preferred.

Accordingly, the inventive methods and products therefrom have several hereinstated utilities. Other utilities also exist for embodiments of the invention.

As to an epitope of interest from a Borrelia genospecies antigen, reference is made to the following discussion, and generally to Kendrew, *The Encyclopedia Of Molecular Biology*, Blackwell Science Ltd., 1995 and Sambrook, Fritsch and Maniatis, *Molecular Cloning, A Laboratory Manual,* 2nd Ed., Cold Spring Harbor Laboratory Press, 1982 ("Maniatis et al., 1982"), U.S. Pat. Nos. 5,582,990, 5,688,512 and 5,777,095, and WO 91/09870, inter alia.

For instance, U.S. Pat. Nos. 5,582,990 and 5,688,512 provide the nucleotide and amino acid sequences of ospA and OspA, the hydropathic index of OspA (location of hydrophobic and hydrophilic amino acids in OspA), the hydrophilicity profile of OspA and the most hydrophilic region of the protein, a curve of the charge of OspA as a function of pH, the amino acid composition of OspA and the secondary structure of OspA, inter alia. U.S. Pat. No. 5,777,095 relates to DNA coding for various OspAs and OspBs, OspAs and OspBs encoded by such DNA (including amino acid sequences therefor), and immunologically interesting fragments of OspAs and OspBs and DNA coding therefor, inter alia. And, WO 91/09870 describes the DNA sequence of the ospC gene of *B. burgdorferi* strain Pko and the OspC protein encoded thereby of 22 kDa molecular weight (termed "pC" therein), inter alia.

More generally, one skilled in the art can determine an epitope or immunodominant region of a peptide or polypeptide, e.g., a Borrelia genospecies antigen such as OspA, OspB or OspC, and ergo the coding DNA therefor, from the knowledge of the amino acid and corresponding DNA sequences of the peptide or polypeptide, as well as from the nature of particular amino acids (e.g., size, charge, etc.) and the codon dictionary, without undue experimentation.

A general method for determining which portions of a protein, e.g., a Borrelia genospecies antigen such as OspA, OspB or OspC, to use in an immunological composition focuses on the size and sequence of the antigen of interest. "In general, large proteins, because they have more potential determinants are better antigens than small ones. The more foreign an antigen, that is the less similar to self configurations which induce tolerance, the more effective it is in provoking an immune response." Ivan Roitt, *Essential Immunology* (Blackwell Scientific Publications, Oxford, 1988).

As to size: the skilled artisan can maximize the size of the protein, e.g., an epitope from a Borrelia genospecies antigen such as OspA, OspB or OspC, encoded by the DNA sequence to be inserted into the vector (keeping in mind the packaging limitations of the vector).

At a minimum, the DNA sequence can code for a peptide at least 8 or 9 amino acids long, i.e., at a minimum an epitope from a Borrelia genospecies antigen such as OspA, OspB or OspC, can be at least 8 or 9 amino acids long. This is the minimum length that a peptide needs to be in order to stimulate a CD8+T cell response (which recognizes virus infected cells or cancerous cells). A minimum peptide length of 13 to 25 amino acids is useful to stimulate a CD4+T cell response (which recognizes special antigen presenting cells which have engulfed the pathogen). See Kendrew, supra. However, as these are minimum lengths, these peptides are likely to generate an immunological response, i.e., an antibody or T cell response; but, for a protective response (as from a vaccine composition), an epitope from a Borrelia genospecies antigen such as OspA, OspB or OspC, is preferably a peptide having a greater length.

With respect to the sequence, the DNA sequence preferably encodes at least regions of the peptide, e.g., a Borrelia genospecies antigen such as OspA, OspB or OspC, that generate an antibody response or a T cell response. One method to determine T and B cell epitopes involves epitope mapping. The protein of interest is fragmented into overlapping peptides with proteolytic enzymes. The individual peptides are then tested for their ability to bind to an antibody elicited by the native protein or to induce T cell or B cell activation. This approach has been particularly useful in mapping T-cell epitopes since the T cell recognizes short linear peptides complexed with MHC molecules. Note that B-cell epitopes are often not linear amino acid sequence but rather result from the tertiary structure of the folded three-dimensional protein. Janis Kuby, *Immunology*, pp. 79–80 (W. H. Freeman, July 1992).

Another method for determining an epitope of interest is to choose the regions of the protein that are hydrophilic. Hydrophilic residues are often on the surface of the protein and are therefore often the regions of the protein which are accessible to the antibody. Janis Kuby, *Immunology*, p. 81 (W. H. Freeman, July 1992).

Yet another method for determining an epitope of interest is to perform an X-ray crystallographic analysis of the antigen (full length)-antibody complex. Janis Kuby, *Immunology*, p.80 (W. H. Freeman, July 1992).

Still another method for choosing an epitope of interest which can generate a T cell response is to identify from the protein sequence potential HLA anchor binding motifs (peptide sequences which are known to be likely to bind to the MHC molecule).

The peptide which is a putative epitope of interest, to generate a T cell response, should be presented in a MHC complex. The peptide preferably contains appropriate anchor motifs for binding to the MHC molecules, and should bind with high enough affinity to generate an immune response. Factors which can be considered are: the HLA type of the patient (vertebrate, animal or human) expected to be immunized, the sequence of the protein, the presence of appropriate anchor motifs and the occurrence of the peptide sequence in other vital cells.

An immune response is generated, in general, as follows: T cells recognize proteins only when the protein has been cleaved into smaller peptides and is presented in a complex called the "major histocompatability complex MHC" located on another cell's surface. There are two classes of MHC complexes—class I and class II, and each class is made up of many different alleles. Different patients have different types of MHC complex alleles; they are said to have a 'different HLA type.'

Class I MHC complexes are found on virtually every cell and present peptides from proteins produced inside the cell. Thus, Class I MHC complexes are useful for killing cells when infected. T cells which have a protein called CD8 on their surface, bind specifically to the MHC class I/peptide complexes via the T cell receptor. This leads to cytolytic effector activities.

Class II MHC complexes are found only on antigen-presenting cells and are used to present peptides from circulating pathogens which have been endocytosed by the antigen-presenting cells. T cells which have a protein called CD4 bind to the MHC class II/peptide complexes via the T cell receptor. This leads to the synthesis of specific cytokines which stimulate an immune response.

An epitope from a Borrelia genospecies antigen such as OspA, OspB or OspC, is preferably a peptide having a length greater than 8 or 9 or 13 to 25 amino acids because cells may cut the expressed peptides. The peptide preferably contains an appropriate anchor motif which will enable it to bind to the various class I or class II molecules with high enough specificity to generate an immune response (See Bocchia, M. et al, *Specific Binding of Leukemia Oncogene Fusion Protein Peptides to HLA Class I Molecules*, Blood 85 (10):2680–2684, May 15, 1995; Englehard, VH, *Structure of peptides associated with class I and class II MHC molecules*, Ann. Rev. Immunol. 12:181 (1994)). This can be done, without undue experimentation, by comparing the sequence of the protein of interest with published structures of peptides associated with the MHC molecules. Protein epitopes recognized by T cell receptors are peptides generated by enzymatic degradation of the protein molecule and are presented on the cell surface in association with class I or class II MHC molecules.

Further, the skilled artisan can ascertain an epitope of interest by comparing the protein sequence with sequences listed in the protein data base.

Even further, another method is simply to generate or express portions of a protein of interest, generate monoclonal antibodies to those portions of the protein of interest, and then ascertain whether those antibodies inhibit growth in vitro. The skilled artisan can use the other guidelines set forth in this disclosure and in the art for generating or expressing portions of a protein of interest, e.g., a Borrelia genospecies antigen such as OspA, OspB or OspC, for analysis as to whether antibodies thereto inhibit growth in vitro. For example, the skilled artisan can generate portions of a protein of interest, e.g., a Borrelia genospecies antigen such as OspA, OspB or OspC, by: selecting 8 to 9 or 13 to 25 amino acid length portions of the protein, selecting hydrophylic regions, selecting portions shown to bind from X-ray data of the antigen (full length)-antibody complex, selecting regions which differ in sequence from other proteins, selecting potential HLA anchor binding motifs, or any combination of these methods or other methods known in the art.

Epitopes recognized by antibodies are expressed on the surface of a protein. To determine the regions of a protein most likely to stimulate an antibody response, e.g., regions of a Borrelia genospecies antigen such as OspA, OspB or OspC most likely to stimulate an antibody response, one skilled in the art can preferably perform an epitope map, using the general methods described above, or other mapping methods known in the art.

As can be seen from the foregoing, without undue experimentation, from this disclosure and the knowledge in the art, the skilled artisan can ascertain the amino acid and corresponding DNA sequence of an epitope of interest of a Borrelia genospecies antigen such as OspA, OspB or OspC, for obtaining a T cell, B cell and/or antibody response. Thus, without undue experimentation, one skilled in the art can make and use plasmids containing and expressing in vivo an immunologically active fragment or fragments or an epitope or epitopes of a Borrelia genospecies antigen, from this disclosure and the knowledge in the art.

A better understanding of the present invention and of its many advantages will be had from the following examples given by way of illustration.

EXAMPLES

Example 1 Plasmid Construction

DNA plasmids VR2210 (FIGS. 1 and 2) (SEQ ID NO:1) and VR2211 (FIGS. 3 and 4) (SEQ ID NO:2) containing, respectively, genes coding for OspA (FIG. 5) (SEQ ID NO:3) and OspB (FIG. 6) (SEQ ID NO:4) from *Borrelia burgdorferi* (see FIG. 7) (SEQ ID NO:5) were constructed by isolating, individually, three DNA molecules: (1) a first DNA molecule having a DNA sequence from restriction endonuclease (PstI and XbaI) digested VR1012 plasmid (FIGS. 8, 9, 10) (SEQ ID NOS:6, 7); (2) a second DNA molecule having a DNA sequence from PCR amplified TPA 5' UTR and leader peptide coding sequence (from nkCM-VintBL; see Manthorpe et al. (1993) Human Gene Therapy 4, 419–431; see also Chapman et al. (1991) Nucleic Acids Research 19, 3979–86), PstI and KpnI digested (subsequent to PCR amplification) (FIGS. 11, 12) (SEQ ID NOS:8, 9); and (3) a third DNA molecule having a DNA sequence from PCR amplified Borrelia antigen coding sequence, KpnI and XbaI digested, e.g., PCR amplified DNA encoding OspA (FIG. 5; SEQ ID NO:3) (PCR primers: FIG. 13; SEQ ID NOS:10, 11) or OspB (FIG. 6; SEQ ID NO:5) (PCR primers: FIG. 14; SEQ ID NOS:12, 13) (see also FIG. 7; SEQ ID NO:5; and Howe et al., 1986, Infection and Immunity 54:207–212 ("Howe et al. 1986"); Bergstrom et al., 1989, Molecular Microbiology, 3(4), 479–486). The natural leader sequences of the DNA encoding the Borrelia antigen is not present so as to facilitate expression and secretion in mammalian cells. The constructs (VR2210, VR2211) express secreted proteins in vitro and elicit a specific antibody response in vivo.

In particular, the construct VR2210 contains DNA encoding OspA and was made by ligating three aforementioned DNA molecules (fragments) together (wherein the third DNA molecule or sequence in the foregoing paragraph is DNA encoding OspA, from a plasmid as in Howe et al. 1986, e.g., pTRH43); and, the construct VR2211 contains DNA encoding OspB and was made by ligating the three aforementioned DNA fragments together (wherein the third DNA molecule or sequence in the foregoing paragraph is DNA encoding OspB from a plasmid as in Howe et al., 1986, e.g., pTRH46).

More specifically, the DNA for encoding TPA 5' UTR and leader peptide, ospA and ospB were PCR amplified. The TPA signal was PCR amplified from plasmid nKCMVintBL using the following primers:

(SEQ ID NO:14)

```
                    PstI
TPA5'-TCT|TTT|CTG|CAG|TCA|CCG|TCG
```

(SEQ ID NO:15)

```
         XbaI    BamHI    KpnI
TPA3'-GAG|AGA|TCT|GGA|TCC|GGT|ACC|GCT|GGG|CGA|AAC|GAA
```

The ospA gene was PCR amplified from pTRH43 using the primers shown in FIG. 13 (SEQ ID NOS:10, 11) ("Forward" is ospA 5' primer and "Reverse" is ospA 3' primer). The ospb gene was PCR amplified from pTRH46 using the primers shown in FIG. 14 (SEQ ID NOS:12, 13) ("Forward" is ospB 5' primer and "Reverse" is ospB 3' primer).

PCR program:

1st—Anneal primer and template
  1. 94° C., 2 minutes
  2. Ramp slowly, 10 minutes, down to 45° C.
  3. 45° C., 5 minutes 2nd—Cycle program
  1. 72° C., 3'
  2. 93° C., 1'30"
  3. Go to 1 32 cycles
  4. 54° C., 2'30"
  5. 72° C. 10'
  6. 4° C. 1–24 hours

PCR REACTIONS

| H$_2$O | BUFFER | dNTPS | 5' PRIMER | 3' PRIMER | DNA | 10x Taq Buffer |
|---|---|---|---|---|---|---|
| 82 µL | 10 µL 10x Taq Buffer | 3 µL (25 mM) | TPA-5' 2 µL (25 mM) pico-mole/µL) | TPA-3' 2 µL (25 pico mole/mM) | ∅ | 1 µL |

PCR REACTIONS -continued

| H₂O | BUFFER | dNTPS | 5' PRIMER | 3' PRIMER | DNA | 10x Taq Buffer |
|---|---|---|---|---|---|---|
| 80 μL | 10 μL 10x Taq Buffer | 3 μL (25 mM) | 2 μL (25 pico mole/μL) | 2 μL (25 pico mole/mM) | 2 μL (5 nano-grams/μL) | 1 μL |
| | 10 μL 10x Taq Buffer | 3 μL (25 mM) | 2 μL (25 pico mole/μL) | 2 μL (25 pico mole/mM) | 2 μL (5 nano-grams/μL) | 1 μL |
| | 10 μL 10x Taq Buffer | 3 μL (25 mM) | 2 μL (25 pico mole/μL) | 2 μL (25 pico mole/mM) | 2 μL (5 nano-grams/μL) | 1 μL |
| 82 μL | 10 μL 10x Taq Buffer | 3 μL (25 mM) | ospA-5' 2 μL (25 pico mole/μL) | ospA-3' 2 μL (25 pico mole/μL) | ø | 1 μL |
| 80 μL | 10 μL 10x Taq Buffer | 3 μL (25 mM) | ospA-5' 2 μL (25 pico mole/μL) | ospA-3' 2 μL (25 pico mole/μL) | 2 μL (5 nano-grams/μL) | 1 μL |
| 72 μL | 10 μL 10x Taq Buffer | 3 μL (25 mM) | ospA-5' 2 μL (25 pico mole/μL) | ospA-3' 2 μL (25 pico mole/μL) | 10 μL (1 nano-grams/μL) | 1 μL |
| 82 μL | 10 μL 10x Taq Buffer | 3 μL (25 mM) | ospB-5' 2 μL (25 pico mole/μL) | ospB-3' 2 μL (25 pico mole/μL) | 1 μL | |
| 80 μL | 10 μL 10x Taq Buffer | 3 μL (25 mM) | ospB-5' 2 μL (25 pico mole/μL) | ospB-3' 2 μL (25 pico mole/μL) | 2 μL (5 nano-grams/μL) | 1 μL |
| 72 μL | 10 μL 10x Taq Buffer | 3 μL (25 mM) | ospB-5' 2 μL (25 pico mole/μL) | ospB-3' 2 μL (25 pico mole/μL) | 10 μL (1 nano-grams/μL) | 1 μL |

The ospA PCR fragments were digested with KpnI/XbaI as follows:

| A. Mixed: | 72 μL | ospA DNA |
|---|---|---|
| | 10 μL | New England Biolabs (NEB) Buffer #1 |
| | 10 μL | 10x Bovine serum albumin (BSA) |
| | 8 μL | KDnI (10 units/μL) |
| | 100 μL | total. |

The mixture was allowed to sit for 2 hrs at 37° C. and then subjected to phenol/chloroform extraction and spin column (G-50 Sephadex) for purification.

| B. Mixed: | 100 μL | DNA (5 μg) (from A.) |
|---|---|---|
| | 11.5 μL | NEB Buffer #2 (New England Biobbs ("NEB") Buffer #2) |
| | 1 μL | BSA 100x |
| | 4 μL | XbaI (20 units/μL) |
| | 115 μL | total. |

The mixture was incubated for 2 hrs at 37° C.
QIAquick (Qiagen) columns were used to purify the fragments (Final volume=50 μL in 10 mM Tris, pH 8.5).
The TPA fragments were digested with PstI/KpnI as follows:

| A. Mixed: | 20 μL | TPA DNA (in Tris pH 8.5) |
|---|---|---|
| | 10 μL | NEB Buffer #1 |
| | 1 μL | 100x BSA |
| | 64 μL | TE (10 mM Tris, 1 mM EDTA, pH 8.0) |
| | 5 μL | KpnI (10 units/μL) |
| | 100 μL | total. |

The mixture was incubated for 2 hrs at 37° C. and then purified by a QIAquick DNA spin column; and eluted with 50 μL H₂O (and then subject to B).

| B. Mixed: | 50 μL | TPA DNA (from A.) |
|---|---|---|
| | 6 μL | NEB Buffer #3 |
| | 2 μL | PstI (10 units/μL) |
| | 2 μL | TE |
| | 60 μL | total. |

The mixture was incubated for 2 hrs at 37° C. Thereafter 40 μL TE was added; and then purified by phenol/chloroform extraction followed by G-50 spin column.

The ospb PCR reaction products that were uncut were consolidated and ethanol precipitated to concentrate them. Then, the ospB products were loaded on a 1% TBE—agarose gel and gel purified using QIAEXII gel extraction (Qiagen) as follows:
1. Excise bands and weigh.
2. Add 3 μL QX1/mg of gel slice.
3. Vortex QIAEX 1' to completely resuspend.
4. Add 10 uL QIAEX for every 5 μg DNA or less Vortex.
5. Incubate at 50° C. for 10' mix every 2 minutes.
6. Centrifuge for 30".
7. Wash 2X in QX2; 500 μL wash. Resuspend by vortex-ing. Spin 30" full speed.

8. Wash 2X in QX3; 500 μL wash.
9. Remove all traces of supernatant after last wash.
10. Allow to air dry 15 minutes.
11. Elute with 20 μL TE. Resuspend. Incubate 5' at room temperature and spin down QIAEX. Remove supernatant.

The ospB fragments were digested with KpnI/BamHI as follows:

| | | |
|---|---|---|
| A. | Mixed: | 5 μL TE |
| | | 33 μL ospB (1.3 μg) |
| | | 5 μL NEB Buffer #1 |
| | | 5 μL 10x BSA |
| | | 2 μL KpnI (10 units/μL) |
| | | 50 μL total. |

The mixture was incubated for 2 hrs at 37° C. Thereafter the mixture was purified with a Qiaquick column and eluted in 30 μl H$_2$O.

| | | |
|---|---|---|
| B. | Mixed: | 30 μL DNA (1.3 mg; from A.) |
| | | 4 μL BamHI Buffer (New England Biolabs) |
| | | 1 μL BamHI (20 μg/μL) (20 units/μL) |
| | | 5 μL TE |
| | | 40 μL total. |

The mixture was incubated for 2 hrs at 37° C. Thereafter the mixture was purified with a QIAquick column, and eluted in 3 μL H$_2$O.

| | | |
|---|---|---|
| A. | Mixed: | 5 μL DNA (5 μg) VR1012 |
| | | 3 μL 10X BSA |
| | | 3 μL NEB Buffer #2 |
| | | 18 μL TE |
| | | 1 μL XbaI (20 units/λ |
| | | 30 μL total. |

The mixture was incubated for 2 hrs at 37° C. 1 μL was then removed for gel analysis which confirmed digestion.

| |
|---|
| B. Added to product of A: |
| 1.5 μL 1M Tris |
| 3.5 μL NaCl (500 mM) |
| 1 μL PstI (10 μ/λ) |
| 35 μL Total |

The mixture in B. incubated sit for 2 hours at 37° C. Thereafter, 1 μL of EcoRV was added and the resultant mixture incubated at 37° C. for an additional hour (this cuts the small restriction fragment in half and can increase efficiency of removal by the spin column). The mixture was then subjected to a G50 spin column to remove the small insert.

To then construct VR2210, a mixture containing 1 μL of the PstI/XbaI digested VR1012 DNA (25 ng), 1 μL of the KpnI/XbaI digested ospA DNA (200 ng), 6 μL of the PstI/KpnI digested TPA DNA (50 ng), 2 μL Rapid DNA Ligation Buffer #2, 10 μL Rapid DNA Ligation Buffer #1, and 1 μL Rapid DNA ligase (Boehringer Mannheim) was prepared. To construct VR2211, a mixture containing 1 μL of the PstI/XbaI digested VR1012 DNA (25 ng), 5 μL of the KpnI/XbaI digested ospB DNA (150 ng), 3 μL of the PstI/KpnI digested TPA DNA, 2 μL Rapid DNA Ligation Buffer #2, 10 μL Rapid DNA Ligation Buffer #1, and 1 μL Rapid DNA ligase (Boehringer Mannheim) was prepared. Rapid, 3-way ligations occurred in each of the mixtures, with VR2210 and VR2211 resulting, respectively. Control mixtures without (i) the ospA and TPA DNA and (ii) the ospb and TPA were also prepared. The control mixtures were set up to test for the number of background clones due to uncut vector. A very low number (less than one-tenth) of clones were generated as a result of these control ligations clearly indicating that the three-way ligations worked efficiently.

FIG. 15 provides a partial sequence of VR2210 extending from a position 5' to PstI site to an arbitrary point 3' to the KpnI site (KpnI, 231) (through the PstI site, the TPA leader, the KpnI site, and into the ospA DNA) (SEQ ID NO: 16). FIG. 16 provides a partial sequence of VR2211 extending from a position 5' to PstI site to an arbitrary point 3' to the KpnI site (KpnI, 266) (through the PstI site, the TPA leader, the KpnI site and into the ospB DNA) (SEQ ID NO: 17).

| ANALYTICAL RESTRICTION DIGEST: | |
|---|---|
| Enzyme(s) | Number and size of fragments |
| VR2210 | |
| 1. KpnI | 2 fragments: 1042/4804 |
| 2. HindIII | 2 fragments: 2803/3043 |
| 3. PstI | 2 fragments: 783/5063 |
| VR2211 | |
| 1. KpnI | 2 fragments: 1091/4803 |
| 2. HindIII | 2 fragments: 2460/3439 |
| 3. PstI | 2 fragments: 834/5065 |

Figure 7A:
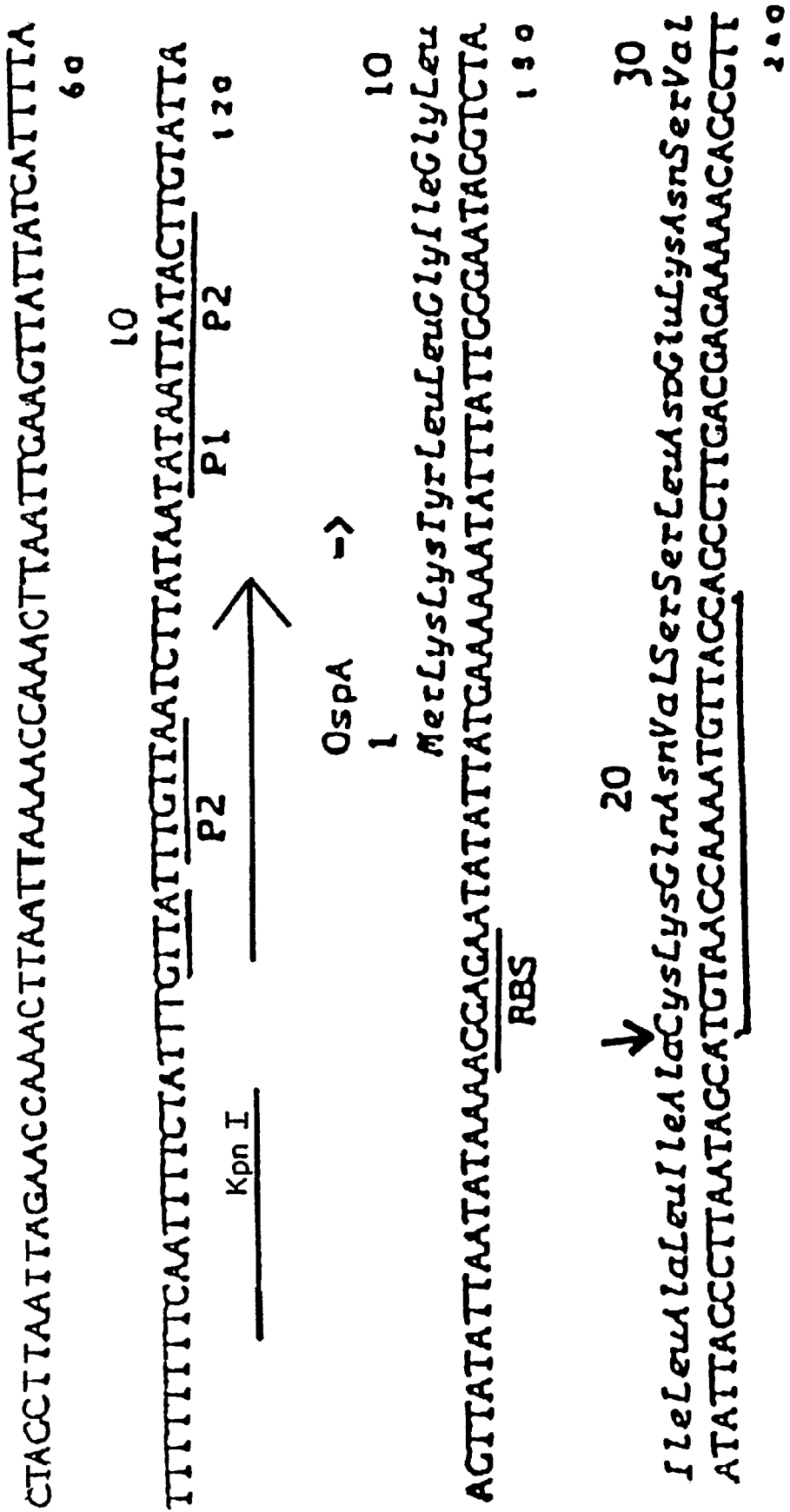
Figure 8:
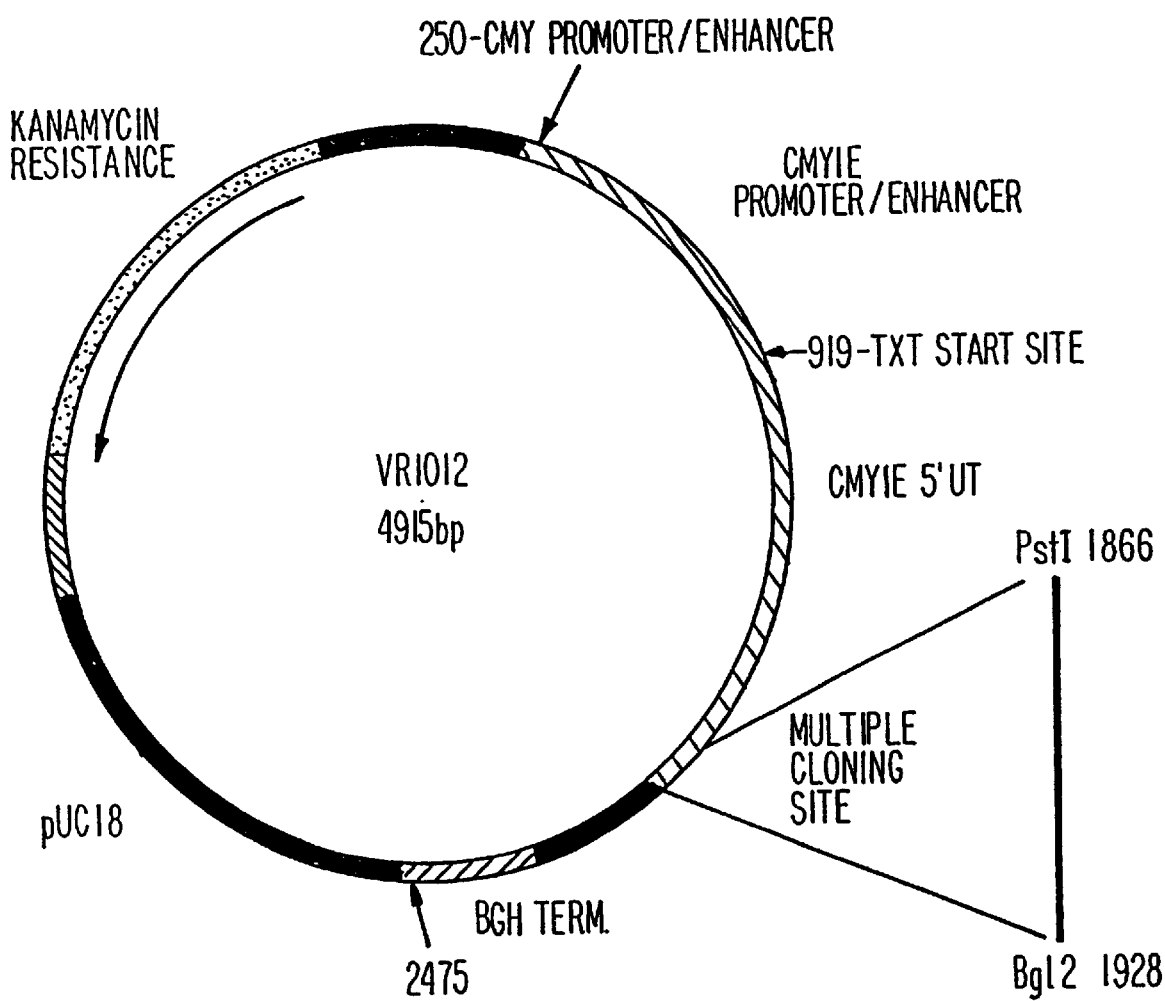
FIG. 8 shows a diagram of VR1012.

FIG. 7 provides the nucleotide sequence (SEQ ID NO: 5) of the ospA and ospB genes and the predicted amino acid sequences (SEQ ID NO: 18) of OspA and OspB. Numbers above each line refer to amino acid positions, whereas numbers below the sequence refer to nucleotide positions. The promoter regions P1 and P2 are indicated by horizontal lines. The respective -35 and -10 regions are also shown. The ribosomal binding sites (RBS) are shown by a horizontal line and bold lettering. A possible stem and loop structure at the end of the ospB sequence is indicated by horizontal broken arrows. Start codons of respective OspA and OspB proteins are indicated and stop codons are marked by asterisks. FIG. 7 also shows the location of the KpnI, XbaI and BamHI sites, with arrows indicating direction (first KpnI to XbaI for OspA DNA, second KpnI to BamHI for OspB DNA are also indicated).

Example 2

Transfections

5μg of VR2210 was transfected into both baby hamster kidney (BHK) and UM449 human melanoma cells (from Mark Cameron, Univ. Mich.) according to the protocol of Felgner et al. (1994), J. Biol. Chem. 269, 2550–2561. The resultant supernatant and cell extract were analyzed for expression of OspA by Western blot, using two anti-OspA antibodies, 3TS at 1:100 dilution and H5332 at 1:10 dilution in 5% milk/BBS (as to the antibodies, reference is made to Barbour, A. G. et al., J. Infect. Dis. 1985, 152, 478–84; Barbour et al., Infect Immun. 1983, 41, 795–804).

As the Western blot (FIG. 17) shows, UM449 cells give a higher level of expression of OspA than BHK cells. Also, there is more OspA in the culture supernatant than in the cell lysate. Therefore, the prokaryotic protein is efficiently transported out of the mammalian cells by a eukaryotic signal peptide sequence (TPA). A summary of the results shown in FIG. 17 is provided by the following tabulation.

| Gel lane | Sample | Cells | sup/ extract | DNA Conc. | DNA/ lipid | Amt. loaded |
|---|---|---|---|---|---|---|
| 1 | VR2211 | UM449 | extract | 5 µg | 1/1 | 40 µl |
| 2 | VR2210 | UM449 | extract | 5 µg | 1/1 | 40 µl |
| 3 | VR2211 | BHK | extract | 5 µg | 1/1 | 40 µl |
| 4 | VR2210 | BHK | extract | 5 µg | 1/1 | 40 µl |
| 5 | MW marker | | | | | 15 µl |
| 6 | pos control | | B31 lysate | | | 1 µl |
| 7 | VR2211 | UM449 | sup | 5 µg | 1/1 | 20 µl |
| 8 | VR2210 | UM449 | sup | 5 µg | 1/1 | 20 µl |
| 9 | VR2211 | BHK | sup | 5 µg | 1/1 | 20 µl |
| 10 | VR2210 | BHK | sup | 5 µg | 1/1 | 20 µl |

*VR2211 is a plasmid containing the OspB gene and is used as a negative control on the Western.

This Example also demonstrates that the inventive Borrelia antigen DNA plasmid compositions are additionally useful for in vitro expression of antigen(s) or epitope(s) (which by themselves are useful, e.g., for preparing antigenic, immunological or vaccine compositions, or for diagnostic, detection or assay purposes).

Example 3

Transfections

5 µg of VR2211 was transfected into UM449 human melanoma cells according to the protocol of Felgner et al. (1994), J. Biol Chem. 269, 2550–2561. Supernatants and cell extracts were analyzed for expression of OspB by Western blot using a monoclonal anti-OspB called H68 and by a monoclonal anti-OspB H6831 (as to the antibodies, reference is made to Barbour et al., Infect. Immun. 1984, 45, 94–100) (FIGS. 18A and 18B) with the ti-OspB H68 and H6831 at 1:10 in Blotto. These antibodies detect OspB in both supernatants and cell extracts. The monoclonal anti-OspB designated H6831 binds to spirochete OspB strain B31 and to unmodified OspB (in vitro translated) but not to modified OspB (i.e., glycosylated and/or phosphorylated by mammalian cellular machinery). Possibly the epitope for H6831 is blocked by eukaryotic post-translational modifications.

A summary of the results shown in FIG. 18A is provided following tabulation.

| Lane | Sample | Cells | sup/ extract | DNA Conc. | DNA/ lipid | Amt. loaded |
|---|---|---|---|---|---|---|
| 1 | B31 | spirochete | lysate | | | 1 µl |
| 2 | MW markers | | | | | 15 µl |
| 3 | VR2211 clone #16 | UM449 | extract | 5 µg | 1/1 | 40 µl |
| 4 | no DNA | UM449 | extract | | all lipid | 40 µl |
| 5 | VR2210 | UM449 | extract | 5 µg | 1/1 | 40 µl |
| 6 | VR2211 clone #1 | UM449 | extract | 5 µg | 1/1 | 40 µl |
| 7 | VR2211 clone #2 | UM449 | extract | 5 µg | 1/1 | 40 µl |
| 8 | VR2211 clone #3 | UM449 | extract | 5 µg | 1/1 | 40 µl |
| 9 | VR2211 clone #4 | UM449 | extract | 5 µg | 1/1 | 40 µl |
| 10 | VR2211 clone #5 | UM449 | extract | 5 µg | 1/1 | 40 µl |

A summary of the results shown in FIG. 18B is provided following tabulation.

| Lane | Sample | Cells | Supernatant | DNA Conc. | DNA/lipid | Amt loaded |
|---|---|---|---|---|---|---|
| 1 | B31 | spirochete | lysate | | | 1 µl |
| 2 | MW markers | | | | | 15 µl |
| 3 | VR2211 #16 | UM449 | sup. | 5 µg | 1/1 | 20 µl |
| 4 | no DNA | UM449 | sup. | | all lipid | 20 µl |
| 5 | VR2210 | UM449 | sup | 5 µg | 1/1 | 20 µl |
| 6 | VR2211 #1 | UM449 | sup. | 5 µg | 1/1 | 20 µl |
| 7 | VR2211 #2 | UM449 | sup. | 5 µg | 1/1 | 20 µl |
| 8 | VR2211 #3 | UM449 | sup. | 5 µg | 1/1 | 20 µl |
| 9 | VR2211 #4 | UM449 | sup. | 5 µg | 1/1 | 20 µl |
| 10 | VR2211 #5 | UM449 | sup. | 5 µg | 1/1 | 20 µl |

This Example further demonstrates that the inventive Borrelia antigen DNA plasmid compositions are additionally useful for in vitro expression of antigen(s) (which by themselves are useful, e.g., for preparing antigenic, immunological or vaccine compositions or for diagnostic, detection, or assay purposes).

Example 4

Animal Study With VR2210

Two groups of five mice were injected with VR2210 (i.e., ten mice; mice A1–A5, B1–B5), and two groups of five mice (i.e., ten mice) were injected with plasmid VR1020 negative control DNA. VR1020 does not contain a coding sequence for a Borrelia antigen. The plasmid and control DNA were diluted in standard saline. Three bilateral injections of DNA were given at two week intervals at a dosage of 50 µg/leg into the rectus femoris muscle. Sera were collected 12 days after each injection and analyzed by 1) Antibody ELISA and 2) Growth Inhibition of Spirochetes. Titers after the first and third injections (Titer #1, Titer #3) are set forth below.

Two weeks after the last injection, mice were challenged with $10^4$Sh2 spirochetes (same OspA serogroup as B31) injected intradermally in the tail. Sh2 is a virulent isolate of the same serogroup as B31. Mice were sacrificed 11 days following the challenge. Bladder, heart, plasma, and cross-cuttings of the tibiotarsal joints were cultured for 15 days at 34° C. in growth medium. Cultures were examined for the presence of spirochetes by phase-contrast microscopy and scored as negative if no spirochetes were seen in 50 high-power fields.

The antibody ELISA titers for the ten mice administered VR2210 are shown in the following Table. The titers were low after one injection and the group showed considerable variability in their immune response. After the third injection, however, the humoral immune response was uni formly high in 8 out of 10 mice with titers of greater than 1:40,000.

ANTIBODY ELISA TITERS
High passage B31 was the antigen used in the ELISA's.

| Mouse | Immunogen | Titer #1 | Titer #3 |
|---|---|---|---|
| A1 | ospA | 640 | 10240 |
| A2 | ospA | 640 | 10240 |
| A3 | ospA | 40 | >40,960 |
| A4 | ospA | 1280 | >40,960 |
| A5 | ospA | 1280 | >40,960 |
| B1 | ospA | <20 | >40,960 |
| B2 | ospA | <20 | >40,960 |
| B3 | ospA | 2560 | >40,960 |
| B4 | ospA | 5120–10,240 | >40,960 |
| B5 | ospA | 1280 | >40,960 |

No antibody binding to B31 (or immune response to B31) was observed for the mice administered the negative control DNA.

The following Table shows the Spirochete Growth Inhibition titers. The numbers indicate the maximal dilution of serum which inhibits spirochete growth in vitro. After the first injection of VR2210, growth inhibition was seen at serum dilutions of 32 to 128. After the third injection, however, inhibition of growth was detected at higher dilutions (up to 512), which is consistent with the antibody titer data.

Growth Inhibitory Titers

Method: Strain B31 spirochetes were mixed with an 8-fold dilution of serum and two-fold serially diluted in a 96-well plate. Guinea pig complement was added to each well to lyse the spirochetes which have bound antibody. The plates were covered with plastic seals and incubated for 72 hours at 34° C. Growth in each well was determined by observation of the phenol red indicator in the medium from red to yellow as well as by phase-contrast microscopy. The numbers were the maximal dilution of serum which inhibits spirochete growth in the well.

| Mouse | Immunogen | Titer #1 | Titer #3 |
|---|---|---|---|
| A1 | ospA | not determined | 256-512 |
| A2 | ospA | not determined | 128-256 |
| A3 | ospA | not determined | 256 |
| A4 | ospA | not determined | 64 |
| A5 | ospA | not determined | 64 |
| B1 | ospA | 32 | not determined |
| B2 | ospA | 64–128 | not determined |
| B3 | ospA | 64 | not determined |
| B4 | ospA | 64–128 | not determined |
| B5 | ospA | 64 | not determined |

No inhibition was observed with the sera of the mice administered the negative control DNA. The organ culture data shown in the following Table indicates that all ten VR2210 vaccinated mice were completely free of spirochetes in all tissues examined whereas all ten negative control mice had spirochetes in their bladder and joints. Therefore, vaccination with three doses of VR2210 gives 100% protection against spirochete challenge in vivo.

PRESENCE OF SPIROCHETES IN CULTURED ORGANS
Combined culture data for all groups. # Positive cultures/Total

| Immunogen | Plasma | Heart | Bladder | Joint |
|---|---|---|---|---|
| ospA | 0/10 | 0/10 | 0/10 | 0/10 |
| control | 3/10 | 7/10 | 10/10 | 10/10 |

This is a demonstration that the Borrelia DNA plasmid is effective against bacterial pathogenic targets. Immunization with VR2210 encoding OspA protects mice completely against intradermal challenge with $10^4$ virulent spirochetes. This in vivo protection correlates with the serum IgG response measured both by antibody ELISA and by an in vitro spirochete growth inhibition assay.

The ability of the inventive composition to elicit a protective response capable of inhibiting spirochete growth demonstrates that the critical immunogenic epitopes on the bacterial protein are conserved when genes encoding these proteins are expressed in mammalian cells. This is particularly interesting and surprising because native OspA contains a lipid moiety on its N-terminus which has been shown to be a crucial determinant for the immunogenicity of the recombinant protein vaccine made from E. coli. In contrast, in the DNA and expression product of the invention, the natural OspA leader sequence which contains the lipidation signal has been replaced by the human TPA leader sequence in VR2210. Since this lipidation event is part of a post-translational processing step found uniquely in prokaryotic cells, it is unlikely that the lipid moiety is present on the VR2210 protein product. And thus, the results obtained by the present invention are indeed surprising and unexpected.

This Example also demonstrates that plasmids encoding OspB, such as VR2211, or another Borrelia antigen, e.g., OspC, or encoding multiple Borrelia antigens, e.g., OspA and OspB and/or OspC, is within the scope of the invention, and are useful. For instance, this Example demonstrates that the inventive Borrelia burgdorferi antigen DNA composition of the invention is useful for eliciting antibodies which have in vivo and in vitro uses (e.g., protective response; diagnostic, detection or assay purposes).

Example 5

Nucleic Acid Immunization

Immunization of mice

6–10 week old female C3H/HeN mice (Harlan Laboratories, IN) were immunized with plasmid VR2210 or VR1020 (control) diluted in sterile standard saline using a collared 28 G ½"(12.7mm) needle. 50 μg of plasmid was administered intra-muscularly into the rectus femoris muscle of each leg in a volume of 0.05 ml composition. Mice were boosted with identical composition on day 14 and day 28.

Challenge with Infectious Borrelia burgdorferi 13 days following the second boost, mice were challenged with Borrelia burgdorferi Sh-2-82 (Erdile et al., 1993). $10^4$ B. burgdorferi Sh-2-82 in 10% v/v BSKII in PBS (pH 7.4) were injected intra-dermally at the base of the tail. This inoculum is 100 times the $ID_{50}$ for this strain of B. burdorferi (Erdile et al., 1993). Mice were sacrificed 10 days following challenge. Bladder, heart and cross-cuttings of tibiotarsal joints were aseptically removed and were placed in 6 ml BSKII containing antibiotics. Cultures were incubated at 34° C. After 15 days, organ cultures were examined by phase contrast microscopy for the presence of spirochaetes. Cultures were considered negative if no spirochaetes were seen in 20 high power fields.

ELISA

Wet, whole cell ELISAs were carried out as previously described (Sadziene et al., 1991) using high passage *B. burgdorferi* B31, strain B311 (Sadziene et al., 1995) as the antigen. Serial dilutions of mouse sera were made in 1% w/v dried non-fat milk in PBS (pH 7.4). Secondary antibody was goat anti-mouse IgG+IgM+IgA (H+L) conjugated to alkaline phosphatase (Zymed Laboratories, Calif.) used at a dilution of 1:1000 in PBS/1% milk. Plates were developed as previously described (Sadziene et al., 1991). Absorbance was read at 490 nm on a Dynatech 580 plate reader. Samples were considered positive if the absorbance value was greater than the mean +3 standard deviations of the mean of that for non-immune and control sera (Burkot et al., 1994).

In vitro Growth Inhibition Assays

Growth inhibitory titers (GI titers) of the sera from the immunized mice were determined as previously described by Sadziene et al., 1993). Two (2) hemolytic units of unheated guinea pig complement (Calbiochem, Calif.) was added to each of the wells of the microtiter plate to give a final concentration of $10HU.ml^{-1}$ of medium after the addition of antibody. Wells were monitored visually for changes in the color of the phenol red indicator in the medium and by phase contrast microscopy of set mounts of well contents. The GI titer was defined as the lowest dilution of antiserum that resulted in pink instead of yellow wells and represented at least 20-fold fewer cells than in wells with no serum added.

PAGE and Immunoblotting

PAGE and immunoblot were carried out as described previously (Sadziene et al., 1995). Twenty four micrograms of recombinant lipidated OspA (see Erdile et al., 1993, U.S. Ser. No. 08/373,455) or *B. burgdorferi* B31 were run on preparative polyacrylamide gels and were then transferred onto nitrocellulose membranes. Immunoblots were dried and stored at 4° C. until needed.

Immunization of Mice with VR2210 Resulted in an OspA-specific Antibody Response

Figure 19:
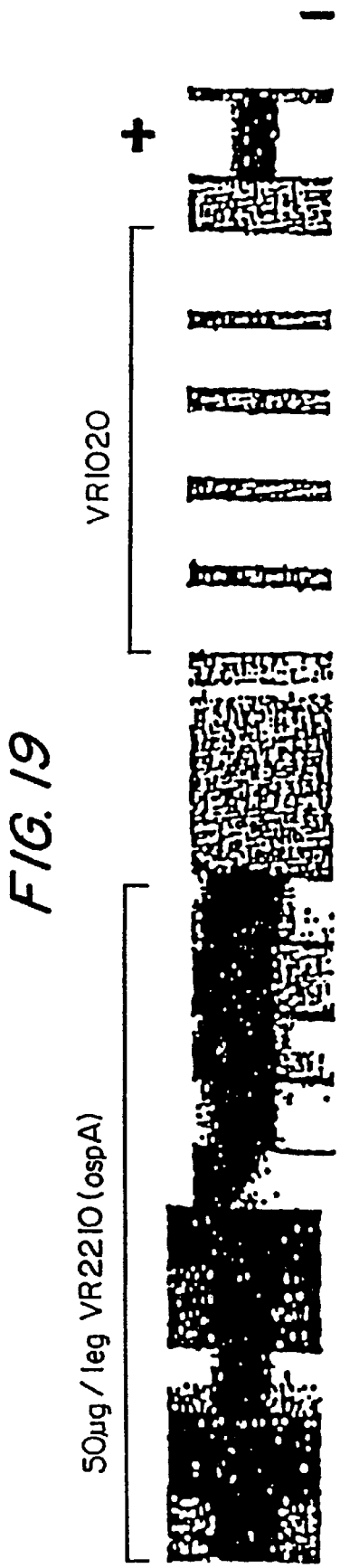
FIG. 19 shows an immunoblot.

Immunoblot of sera from the mice showed that those that received the plasmid bearing the *B. burgdorferi* B31 ospA gene, VR2210, developed an OspA-specific antibody response (FIG. 19). ELISA of the sera also showed that these mice had mounted a significant antibody response against B31. The geometric mean reciprocal ELISA titers are given in the following Table. The sera from the mice that received the plasmid with no Borrelia gene inserted, VR 1020, did not demonstrate an antibody response to *B. burgdorferi*. The sera from the VR2210-immunized mice were found to inhibit growth of *B. burgdorferi* in vitro, to the same level as sera known to be protective. The geometric mean reciprocal GI titers of the sera are also given in the following Table.

The Table shows the reciprocal geometric mean ELISA titers of the sera from the VR2210-immunized mice when IP-90 (B. garinii) and ACA-I (B. afzelii) were used as antigen (sera are from the bleed taken 2 days before challenge).

Challenge with Infectious *B. burgdorferi*

The results of the challenge of the DNA-immunized mice with *B. burgdorferi* Sh-2-82 are shown in the following Table. All mice which received VR2210 were protected against challenge, whereas Borrelias were recovered from all the mice that received the VR1020 plasmid, indicating no protection in these animals.

Table

Reciprocal geometric mean ELISA titers and GI titers and results of infectious challenge of mice immunized with DNA constructs VR2210 and VR1020.

| Immunogen | ELISA TITER | | | GI TITER | CULTURE POSITIVE* |
|---|---|---|---|---|---|
| | B31 | IP-90 | ACA-I | | |
| VR2210 (ospA) | 54,696 | 2941 | 2389 | 388 | 0/10 |
| VR1020 (no insert) | ≤20 | ≤20 | ≤20 | ≤8 | 10/10 |

*Culture positive at one or more sites.

The results in this Table show that the invention is applicable to genospecies *burgdorferi*, *garinii* and *afzelii*; and need not be limited to *burgdorferi* or B31.

FIG. 19 is an immunoblot of *Borrelia burgdorferi* rospA probed with sera from mice immunized with either plasmid VR2210 (ospA) or VR1020. Sera were diluted 1:100. The positive control (+) was H5332 (anti-OspA) monoclonal hybridoma supernatant, diluted 1:10.

The immunization was repeated with the plasmid construct VR2211, containing the ospB of *Borrelia burgdorferi* B31. An additional boost of this plasmid was given two weeks after the second boost. The 5 mice that received this construct, along with three mice that received VR1020, were challenged, and are sacrificed later. OspB-specific antibodies in sera from the VR2211 (ospB) immunized mice were detected on Western blots.

Also, the VR2210 immunization was repeated, along with rOspA lipoprotein controls (immunized subcutaneously or intra-muscularly with 1 μg) (5 mice per group) and the mice are bled every 2 weeks to assess the duration of the immune response to OspA by ELISA and growth inhibition assay. The results parallel those provided above.

This Example demonstrates that Borrelia antigen or epitope DNA compositions of the invention are useful for eliciting an in vivo response, which can be protective against infection (and ergo against Lyme Disease); and, that the compositions of the invention are useful for merely eliciting antibodies, which by themselves are useful (e.g., for diagnostic, detection or assay purposes).

Example 6

Figure 20:
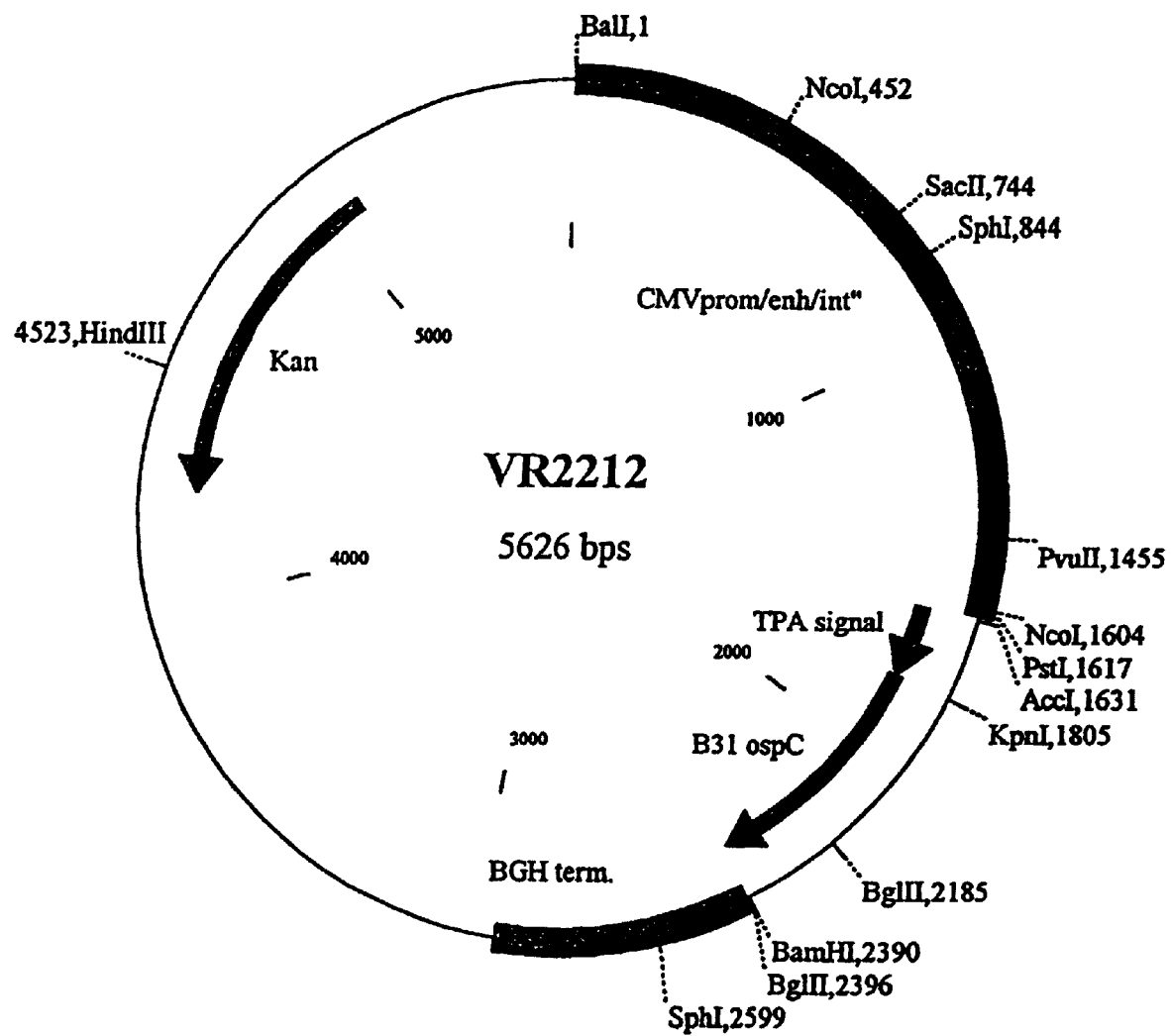
FIG. 20 shows a diagram of VR2212 with a few characteristic restriction sites.
Figure 22:
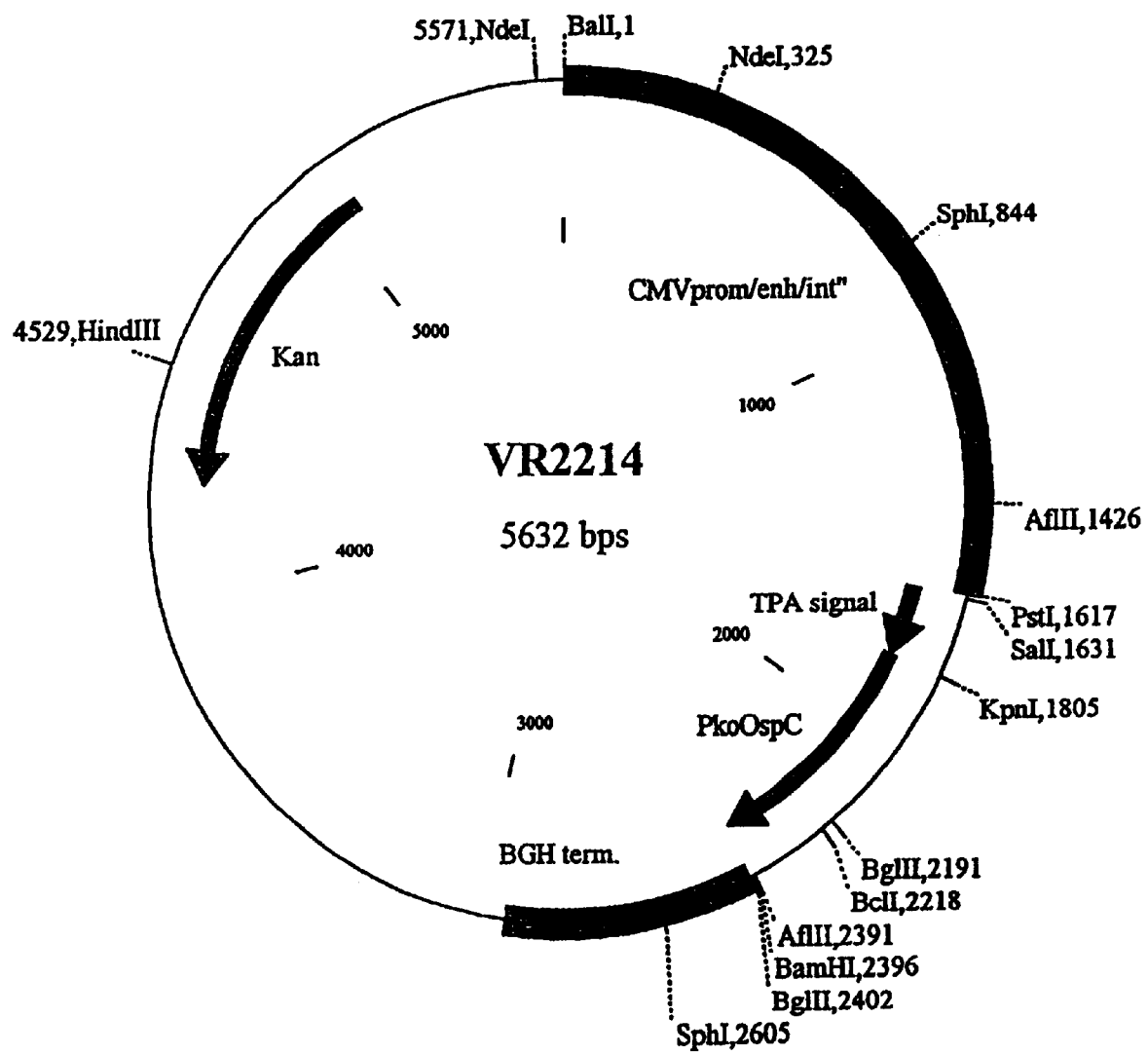
FIG. 22 shows a diagram of VR2214 with a few characteristic restriction sites.

OspC Plasmids and Nucleic Acid Immunization Therewith
OspC Cloning and Plasmid Constructions DNA plasmids VR2212 (FIGS. 20 and 21) (SEQ ID NO:19) and VR2214 (FIGS. 22 and 23) (SEQ ID NO:20) containing genes coding for OspC from *Borrelia burgdorferi* strains B31 and Pko, respectively. These plasmids were constructed by isolating the DNA encoding OspC (i.e., the coding region for OspC, or the DNA coding for only the mature protein, without the leader sequence), and ligating that DNA with DNA for plasmid VR1027 by methods analogous to those in the foregoing examples (plasmid VR1027 is analogous to plasmid VR1020, discussed supra, insofar as VR1027 is VR1020 with KpnI site in the BGH term mutated to a PpuMI site; plasmid VR1020 is plasmid VR2210 without the *B. burgdorferi* DNA which is present in VR2210).

More specifically, plasmids pB319a4 and pPko9a were provided by Pasteur Merieux Connaught, Swiftwater Pa. These plasmids contained isolated nucleic acid molecules encoding OspC-lipidated proteins from *B. burgdorferi* B31 and Pko, respectively, with the ACA OspA signal. DNA sequences for OspC from *B. burgdorferi* strains are also known from the literature (see, e.g., V. Preac-Mursic et al., Infection 20:342–349, 1992; W. S. Probert et al., Infection and Immunity 62:1920–1926, 1994; published international patent application WO 91/09870 (Mikrogen Molekularbiologische Entwicklungs-GmbH); Leuba-Garcia et al., Zentralbl Bakteriol. 287(4):475–84, 1998; Rauer et al., J. Clin. Microbiol. 36(4):857–61, 1998; Masuzawa et al., Clin. Diagn. Lab. Immunol. 4(1):60–63, 1997; Fukunaga et al. J. Clin. Microbiol. 33(9):2415–2420, 1995; Jauris-Heipke et al., J. Clin. Microbiol. 33(7):1860–66, 1995; Theisen et al., J. Bacteriol. 177(11):3036–3044, 1995; Stevenson et al. FEMS Microbiol. Lett. 124(3):367–72, 1994; and Padula et al., Infect. Immun. 61(12):5097–5105, 1993).

The DNA encoding OspC was amplified by PCR reactions using the following primers:

(SEQ ID NO:21)

ospC 5'-KpnI

GGGGGGTACCTGTAATAATTCAGGG (SEQ ID NO:22)

ospC 3'-BamHI

GGGGGGATCCTTAAGGTTTTTTGG

The PCR reactions were performed in a manner analogous to that specified in the foregoing examples. The PCR reactions contained: 10 ng of plasmid DNA (pB319a4), 10 μL of Taq Buffer, 3 μL dNTPs, 50 picomoles of each primer, and 1 μL Taq; and 10 ng of plasmid DNA (pPko9a), 10 μL of Taq Buffer, 3 μL dNTPs, 50 picomoles of each primer, and 1 μL Taq.

The amplification products were separated by gel electrophoresis such that bands were obtained for a B31 ospC KpnI/BamHI fragment ("B31 ospC K/B"), and a Pko ospC KpnI/BamHI fragment ("Pko ospC K/B"). These bands were excised from the gel and purified using a QIAEX procedure, analogous to that described above in foregoing examples. Each band was eluted with TE to a total volume of 35 μL.

Restriction BamHI digestions were as follows:

| | | |
|---|---|---|
| a. | Mixed: | 35.00 μL of B31 ospC K/B |
| | | 4.50 μL of NEB #2 |
| | | 4.50 μL of NaCl (1M) |
| | | 0.50 μL of 100X BSA |
| | | 1.00 μL of BamHI (10 units/μL) |
| | Total: | 45.50 μL |
| b. | Mixed: | 35.00 μL of Pko ospc K/B |
| | | 4.50 μL of NEB #2 |
| | | 4.50 μL of NaCl (1M) |
| | | 0.50 μL of 100X BSA |
| | | 1.00 μL of BamHI (10 units/μL) |
| | Total: | 45.50 μL |

Each of mixtures a. and b. was allowed to incubate for 2 hours at 37° C. to digest. The digests were extracted with phenol/chloroform and were then put through a spin column (G-50 Sephadex) to obtain B31 and Pko ospC products. These products were then subjected to KpnI digestion as follows:

| | | |
|---|---|---|
| a. | Mixed: | 50.00 μL of B31 ospC product |
| | | 2.40 μL TE |
| | | 5.00 μL of New England Biolabs (NEB) #1 |
| | | 0.60 μL of 100X Bovine Serum Albumin (BSA) |
| | | 2.00 μL of KpnI (10 units/μL) |
| | Total: | 60.00 μL |
| b. | Mixed: | 50.00 μL of Pko ospC product |
| | | 2.40 μL TE |
| | | 5.00 μL of NEB #1 |
| | | 0.60 μL of 100X BSA |
| | | 2.00 μL of KpnI (10 units/μL) |
| | Total: | 60.00 μL |

Each of mixtures a. and b. was allowed to incubate for 2 hours at 37° C. to digest. The digests were extracted with phenol/chloroform and were then put through a spin column (G-50 Sephadex) to obtain B31 and Pko ospC (coding region, i.e., coding for only the mature OspC protein without the leader sequence).

Figure 24:
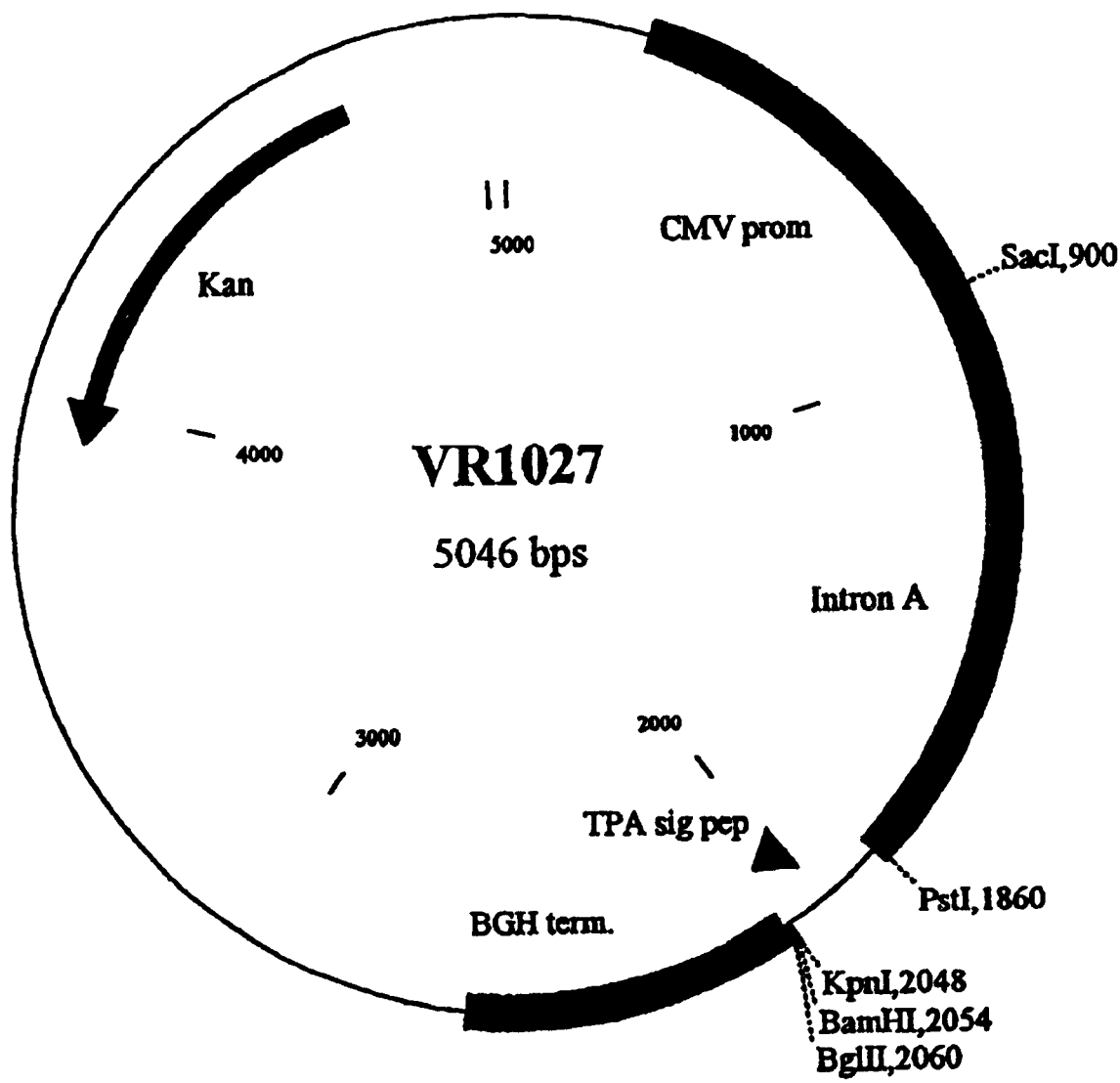
FIG. 24 shows a diagram of VR1020 with a few characteristic restriction sites.
Figure 25:
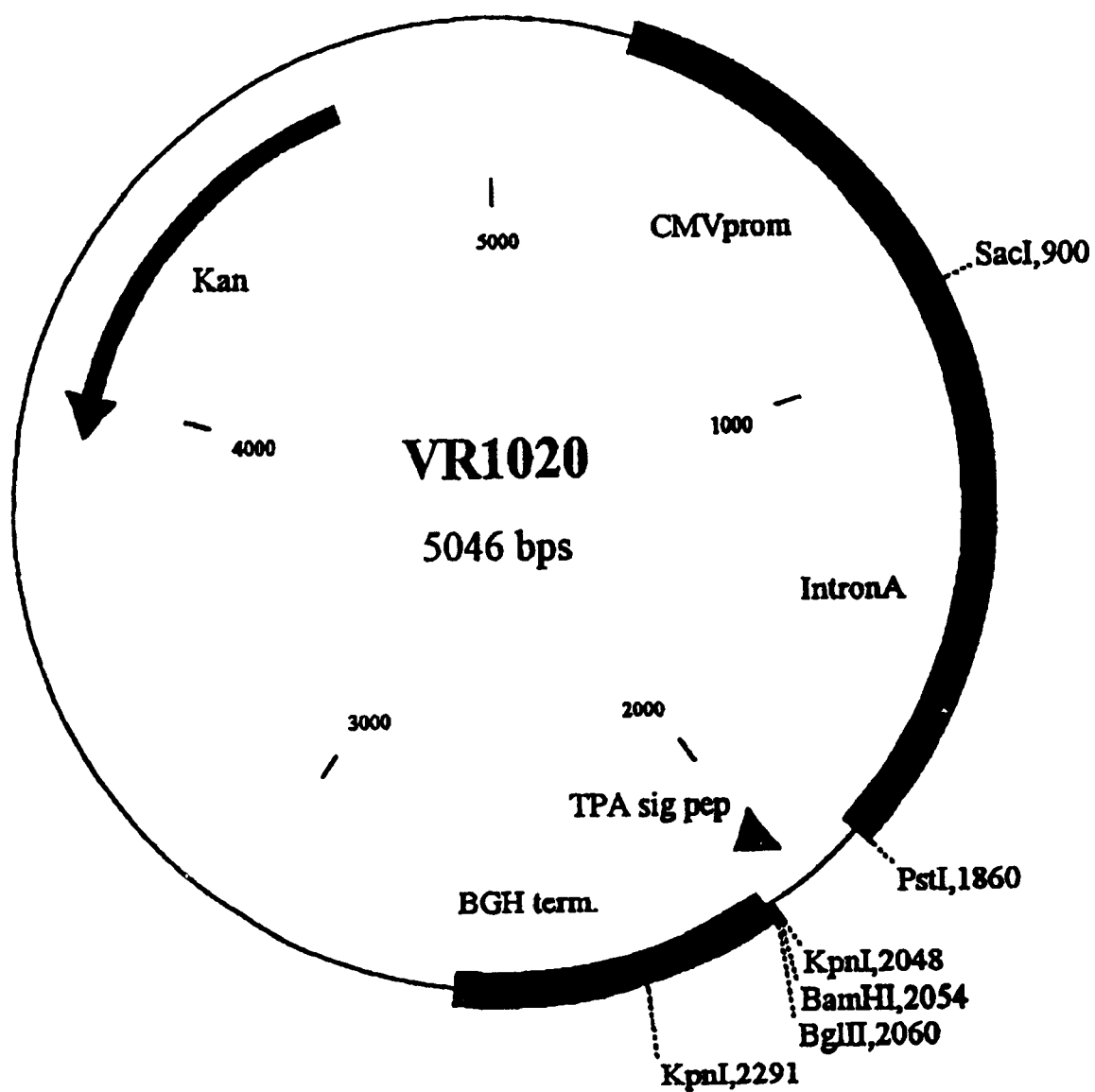
FIG. 25 shows a diagram of VR1027 with a few characteristic restriction sites.

As discussed above, VR1027 is analogous to VR1020. A diagram of VR1020 is provided in FIG. 24. A diagram of VR1027 is provided in FIG. 25 and the nucleotide sequence for VR1027 (SEQ ID NO:23) is provided in FIG. 26.

| | | |
|---|---|---|
| a. | Mixed: | 28.00 μL of TE |
| | | 2.00 μL of VR1027 (5 μg) |
| | | 5.00 μL of NEB #2 |
| | | 5.00 μL of NaCl (1M) |
| | | 5.00 μL of 10X BSA |
| | | 5.00 μL of BamHI (10 units/μL) |
| | Total: | 50.00 μL |

Mixture a. was allowed to incubate for 2 hours at 37° C. to digest. The digest was extracted with phenol/chloroform and was then put through a spin column (G-50 Sephadex) to obtain a BamHI cut VR1027 product. This product was then subjected to KpnI digestion as follows:

| | | |
|---|---|---|
| b. | Mixed: | 50.00 μL of DNA (BamHI cut VR1027 product) |
| | | 6.00 μL of NEB #1 |
| | | 0.60 μL of 100X BSA |
| | | 4.00 μL of KpnI (10 units/μL) |
| | Total: | 60.60 μL |

The volume of the digest was brought to approximately 100 μL with TE by the addition of 40 μL TE. 1 μL calf intestine alkaline phosphatase (CIAP) was then added, and the resultant mixture was incubated for 10 min at 37° C. Thereafter the enzyme was heat-killed by bringing the mixture to 65° C. for 10 min. The digest was then extracted with phenol/chloroform and was then put through a spin column (G-50 Sephadex) to obtain a BamHI and KpnI cut VR1027 product.

The BamHI and KpnI cut VR1027 product was then used in ligations with the B31 and Pko ospc (coding region, i.e., coding for only the mature OspC protein without the leader sequence).

More in particular, to then construct VR2212, a mixture containing 1 μL of the BamHI and KpnI cut VR1027 product, 1 μL of the BamHI/KpnI cut B31 ospC DNA, 2 μL Rapid DNA Ligation Buffer (RDLB) #2, 10 μL Rapid DNA Ligation Buffer #1, 6 μL of TE, and 1 μL ligase (Boehringer Mannheim) was prepared. To construct VR2214, a mixture containing 1 μL of the BamHI and KDnI cut VR1027 product, 1 μL of the BamHI/KpnI cut Pko ospC DNA, 2 μL RDLB #2, 10 μL RPLB #1, 6 μL of TE, and 1 μL Rapid DNA ligase (Boehringer Mannheim) was prepared. Rapid ligations occurred in each of the mixtures, with VR2212 and VR2214 resulting, respectively. Restriction Endonuclease analysis confirmed that B31 ospC had been inserted into VR1027 to form VR2212 and that Pko ospC had been inserted into VR1027 to form VR2214.

Confirmation of OspC Expression by VR2212 and VR2214

Mice were immunized with lipidated OspC from both Pko and B31 *B. Burgdorferi* strains (1 μg/antigen) on days 0, 21 and 42. At day 63 the mice were bled to obtain an antisera pool.

UM449 cells were transfected with plasmid VR2212 in duplicate wells of a 6-well dish. UM449 cells were also transfected with plasmid VR2214 in duplicate wells of a 6-well dish. The mouse antisera pool as described above was diluted to a 1/300 dilution. The transfected UM449 cells were subjected to Western blot analysis using the diluted mouse antisera. The Western blot analyses confirmed that VR2212 and VR2214 each express OspC.

In Vivo Study using VR2212 and VR2214

Formulation A: VR2212 @ 1000 μg/ml:

1.6 ml VR2212@6240 μg/ml+8.4 ml PBS.

Formulation B: VR2214 @ 1000 μg/ml:

2.05 ml VR2214@4870 μg/ml+7.95 ml PBS.

Formulation C: VR1027 @ 1000 μg/ml:

1.02 ml VR1027@9760 μg/ml+8.98 ml PBS (control).

Group 1: 8 C3H/He mice were each intramuscularly injected with 0.1 ml of Formulation A.

Group 2: 8 ICR mice were each intramuscularly injected with 0.1 ml of Formulation A.

Group 3: 8 C3H/He mice were each intramuscularly injected with 0.1 ml of Formulation B.

Group 4: 8 ICR mice were each intramuscularly injected with 0.1 ml of Formulation B.

Group 5: 8 C3H/He mice were each intramuscularly injected with 0.1 ml of Formulation C.

Group 6: 8 ICR mice were each intramuscularly injected with 0.1 ml of Formulation C.

Group 7: All three groups of C3H/He mice were bled on day 0 and their sera pooled.

Group 8: All three groups of ICR mice were bled on day 0 and their sera pooled.

The mice of Groups 1 to 6 were bled on days 21, 42, 63, 91 and 119 from the tail vein. Enough blood was removed from each mouse to generate 50 μL of serum, and each serum sample was kept separate.

The sera were tested for the presence of OspC using ELISA. The antigens used to assess the anti-OspC response were obtained as follows: Non-lipidated B31 OspC was used to assess the B31 OspC response and non-lipidated Pko OspC was used to assess the Pko OspC response. These non-lipidated versions of B31 and Pko OspC were purified using the method described in published international patent application WO 91/09870 (Mikrogen Molekularbiologische Entwicklungs-GmbH), with one modification; namely, the material eluted from the DEAE column was dialyzed into phosphate buffer instead of diluted into the buffer. The results of the ELISA are shown in FIG. 27 and are described below.

More in particular, the sera collected from Groups 1 to 8 were tested by ELISA for the presence of OspC. The sera from Groups 5 to 8 showed no OspC. Groups 1 to 4 tested positively for expression of OspC in vivo.

More specifically, FIG. 27 shows a graph of ELISA GMT vs. days for Group 1 (diamonds: C3H/He mice that received B31 ospC DNA in plasmid form, i.e., VR2212), Group 2 (squares: ICR mice that received B31 ospC DNA in plasmid form, i.e., VR2212), Group 3 (triangles: C3H/He mice that received Pko ospC DNA in plasmid form, i.e., VR2214), and Group 4 (X's: ICR mice that received Pko ospC DNA in plasmid form, i.e., VR2214).

As can be seen from FIG. 27, VR2212 and VR2214 each resulted in expression in vivo of OspC and the resultant generation of antibodies to OspC.

For instance, VR2214 in ICR mice (Group 4) resulted in ELISA GMT of about 66.67 on all days tested; VR2212 in ICR mice (Group 2) resulted in ELISA GMT of about 66.67 on day 21, about 150 on day 42, about 700 on day 63, about 1466.67 on day 91, about 1200 on day 119, and about 1000 beyond day 140; VR2214 in C3H/He mice resulted in ELISA GMT of about 66.67 on days 21 and 42, about 100 on day 63, about 300 on day 82, about 190 on day 119 and about 66.67 beyond day 140; and, VR2212 in C3H/He mice resulted in ELISA GMT of about 66.67 on day 21, about 290 on day 42, about 250 on day 63, about 700 on day 82, about 400 on day 119 and about 250 beyond day 140.

Thus, VR2212 and 2214 are capable of having OspC expressed in vivo; and that the expressed OspC is capable of eliciting OspC specific antibodies. It is therefore expected that VR2212 and VR2214 will provide protection against Lyme disease in the same fashion that immunizations with OspC protein provide protection against Lyme disease.

Accordingly, this Example demonstrates that Borrelia antigen or epitope DNA compositions of the invention, especially such compositions wherein the DNA codes for OspC or an epitope of OspC, are useful for eliciting an in vivo response, which response may be protective against infection (and ergo against Lyme Disease); and, that the compositions of the invention are useful for merely eliciting antibodies, which by themselves are useful (e.g., for diagnostic, detection or assay purposes).

Having thus described in detail preferred embodiments of the present invention, it is to be understood that the invention defined by the appended claims is not to be limited by particular details set forth in the above description as many apparent variations thereof are possible without departing from the spirit or scope thereof.

REFERENCES

1. Barbour et al., Infect Immun., 41, 795–804 (1983).
2. Barbour, A. G. and Fish, D., The biological and social phenomenon of Lyme Disease, *Science* 260, 1610–1616 (1993).
3. Barbour, A. G. et al., J. Infect. Dis., 152, 478–84 (1985).
4. Barbour et al., Infect. Immun. 45, 94–100 (1984).
5. Bergstrom, S., Bundoc V. G., and Barbour, A. G., Molecular analysis of linear plasmid-encoded major surface proteins OspA and OspB, of the Lyme disease spirochaete *Borrelia burgdorferi*, Mol. Microbiol. 3:479–486 (1989).
6. Bocchia, M. et al., *Specific Binding of Leukemia Oncogene Fusion Protein Peptides to HLA Class I Molecules*, Blood 85(10):2680–2684, May 15 (1995).
7. Bourne al., The Journal of Infectious Disease, 173:800–7, (1996).
8. Burkot, T. R., Piesman, J., and Wirtz, R. A. Quantitation of the *Borrelia burgdorferi* outer surface protein A in Ixodes scapularis: fluctuations during the tick life cycle, doubling times, and loss while feeding. *J. Infect. Dis.,* 170, 883–889 (1994).
9. Chapman et al., Nucleic Acids Research 19, 3979–86 (1991).

10. Englehard, VH, *Structure of peptides associated with class I and class II MHC molecules*, Ann. Rev. Immunol. 12:181 (1994).
11. Erdile, L. f., Brandt, M., Warakomski, D. J., Westrack, G. J., Sadziene, A., Barbour, A. G. and Mays, J. P. Role of attached lipid in immunogenicity of *Borrelia burgdorferi* OspA. *Infect. Immun.* 61, 81–90 (1993).
12. Felgner et al., J. Biol. Chem. 269, 2550–2561 (1994).
13. Fikrig, E., Barthold, S. W., Kantor, F. S. and Flavell, R. A. Protection of mice against the Lyme disease agent by immunizing with recombinant OspA. *Science*, 250, 553–556 (1990). 14. Fukunaga et al. J. Clin. Microbiol. 33(9):2415–2420 (1995).
15. Howe et al., Infection and Immunity 54:207–212 (1986).
16. Jauris-Heipke et al., J. Clin. Microbiol. 33(7):1860–66, (1995).
17. Keller, D., Kister, F. T., Marks, D. H., Hosback, P., Erdile, L. F. and Mays, J. P. Safety and immunogenicity of a recombinant outer surface protein A Lyme vaccine, *J. Am. Med. Assoc.* 271, 1764 (1994).
18. Kendrew, The Encyclopedia Of Molecular Biology, Blackwell Science Ltd. (1995).
19. Kuby, Immunology, pp. 79–80, W. H. Freeman, July (1992).
20. Leuba-Garcia et al., Zentralbl Bakteriol. 287(4):475–84 (1998).
21. Luke et al., J. Infect. Dis., 175(1):91–97 (1997).
22. Manthorpe et al., Human Gene Therapy 4, 419–431 (1993).
23. Masuzawa et al., Clin. Diagn. Lab. Immunol. 4(1): 60–63, (1997).
24. Milstein, C., Scientific American 243:66, 70 (1980).
25. Norman et al., Vaccine, 15(8):801–803 (1997).
26. Padula et al., Infect. Immun. 61(12):5097–5105 (1993).
27. Preac-Mursic et al., INFECTION 20:342–349 (1992).
28. Probert et al., INFECTION AND IMMUNITY 62:1920–1926 (1994).
29. Rauer et al., J. Clin. Microbiol. 36(4):857–61 (1998).
30. Robinson et al., seminars in IMMUNOLOGY, 9:271–83 (1997).
31. Roitt, Essential Immunology, Blackwell Scientific Publications, Oxford (1988).
32. Sadziene, A., Thompson, P. A., and Barbour, A. G. In vitro inhibition of *Borrelia burgdorferi* growth by antibodies, J. Infect. Dis. 167, 165–172 (1993).
33. Sadziene, A., Thomas, D. D., and Barbour, A. G. *Borrelia burgdorferi* mutant lacing Osp: biological and immunological characterization, *Infect. Immun.* 63, 1573–1580 (1995).
34. Sadziene, A., Thomas, D. D., Bundoc, V. G., Holt, S. H., and Barbour, A. G. A flagella-less mutant of *Borrelia burgdorferi*. J. Clin. Invest. 88, 82–92 (1991).
35. Sambrook, Fritsch and Maniatis, Molecular Cloning, A Laboratory Manual, 2nd Ed., Cold Spring Harbor Laboratory Press (1982).
36. Stevenson et al. FEMS Microbiol. Lett. 124(3):367–72 (1994).
37. Theisen et al., J. Bacteriol. 177(11):3036–3044 (1995).

What is claimed is:

1. A vaccine against Lyme Disease or its causative agent *Borrelia burgdorferi* (sensu stricto or sensu lato) comprising plasmid a comprising a DNA encoding a promoter for driving expression in a mammalian cell, DNA encoding a leader peptide for facilitating secretion/release of a prokaryotic protein sequence from a mammalian cell, a DNA encoding a Borrelia antigen or epitope comprising OspA, and a DNA encoding a terminator.

2. A vaccine against Lyme Disease or its causative agent *Borrelia burgdorferi* (sensu stricto or sensu lato) comprising a plasmid comprising a DNA encoding a promoter for driving expression in a mammalian cell, DNA encoding a leader peptide for facilitating secretion/release of a prokaryotic protein sequence from a mammalian cell, a DNA encoding a Borrelia antigen or epitope comprising OspB, and a DNA encoding a terminator.

3. The vaccine of claim 1 or 2 or the immunogenic composition of claim 1 wherein the promoter is a mammalian virus promoter.

4. The vaccine or the immunogenic composition of claim 3 wherein the promoter is a herpes virus promoter.

5. The vaccine or the immunogenic composition of claim 4 wherein the promoter is a human cytomegalovirus promoter.

6. The vaccine or the immunogenic composition of claim 5 wherein the DNA encoding a leader peptide is from DNA encoding human tissue plasminogen activator.

7. The vaccine or the immunogenic composition of claim 6 wherein the DNA encoding a terminator is the 3' UTR transcriptional terminator from the gene encoding Bovine Growth Hormone.

8. The vaccine according to claim 1 or 2 or the immunogenic composition according to claim 1 comprises an epitope of *Borrelia burgdorferi, garini, afzelii* or mixtures thereof.

9. A vaccine according to claim 1 or 2 or the immunogenic composition according to claim 1 including a carrier or diluent.

10. A method for vaccinating or inducing an immunological response against Lyme Disease or it causitive agent agent *Borrelia burgdorferi* (sensu stricto or sensu lato) comprising intramuscularly administering the vaccine claimed in claim 1 or 2.

11. An immunogenic composition against Lyme Disease or its causative agent *Borrelia burgdorferi* (sensu stricto or sensu lato) comprising a plasmid comprising a DNA encoding a promoter for driving expression in a mammalian cell, DNA encoding a leader peptide for facilitating secretion/release of a prokaryotic protein sequence from a mammalian cell, a DNA encoding a Borrelia antigen or epitope comprising OspC, and a DNA encoding a terminator.

12. A method for inducing an immunological response against Lyme Disease or it causitive agent agent *Borrelia burgdorferi* (sensu stricto or sensu lato) comprising intramuscularly administering the immunogenic composition of claim 1.

* * * * *

UNITED STATES PATENT AND TRADEMARK OFFICE
CERTIFICATE OF CORRECTION

PATENT NO.     : 6,451,769 B1
DATED          : September 17, 2002
INVENTOR(S)    : Robert C. Huebner et al.

It is certified that error appears in the above-identified patent and that said Letters Patent is hereby corrected as shown below:

Title page,
Item [73], Assignees: change "Lyons" to -- Lyon --.

Column 65,
Lines 2-3, change "comprising plasmid a comprising"
to -- comprising a plasmid comprising --.

Column 66,
Lines 40-41, change "Lyme Disease or it causitive agent agent Borrelia" to
-- Lyme Disease or its causative agent Borrelia --.
Line 53, change "Lyme Disease or it causitive agent agent Borrelia" to
-- Lyme Disease or its causative agent Borrelia --.

Signed and Sealed this

Twenty-eighth Day of January, 2003

JAMES E. ROGAN
*Director of the United States Patent and Trademark Office*